(12) United States Patent
Gross et al.

(10) Patent No.: US 8,852,272 B2
(45) Date of Patent: Oct. 7, 2014

(54) TECHNIQUES FOR PERCUTANEOUS MITRAL VALVE REPLACEMENT AND SEALING

(75) Inventors: Yossi Gross, Moshav Mazor (IL); Gil Hacohen, Raanana (IL); Eran Miller, Moshav Beit Elazari (IL); Yuval Zipory, Modi'in (IL); Tal Reich, Binyamina (IL); Meir Kutzik, Ramat Gan (IL)

(73) Assignee: Mitraltech Ltd., Or Yehuda (IL)

( * ) Notice: Subject to any disclaimer, the term of this patent is extended or adjusted under 35 U.S.C. 154(b) by 0 days.

(21) Appl. No.: 13/412,814

(22) Filed: Mar. 6, 2012

(65) Prior Publication Data
US 2013/0035759 A1 Feb. 7, 2013

Related U.S. Application Data

(60) Provisional application No. 61/515,372, filed on Aug. 5, 2011, provisional application No. 61/525,281, filed on Aug. 19, 2011, provisional application No. 61/537,276, filed on Sep. 21, 2011, provisional application No. 61/555,160, filed on Nov. 3, 2011, provisional application No. 61/588,892, filed on Jan. 20, 2012.

(51) Int. Cl.
*A61F 2/24* (2006.01)
*A61F 2/06* (2013.01)
*A61F 2/848* (2013.01)

(52) U.S. Cl.
CPC ......... *A61F 2/2436* (2013.01); *A61F 2250/006* (2013.01); *A61F 2250/0071* (2013.01); *A61F 2220/0016* (2013.01); *A61F 2220/0091* (2013.01); *A61F 2/848* (2013.01); *A61F 2250/0069* (2013.01); *A61F 2220/0025* (2013.01); *A61F 2/2418* (2013.01); *A61F 2/2409* (2013.01); *A61F 2250/0015* (2013.01); *A61F 2/2439* (2013.01)
USPC ........................................ 623/2.18; 623/1.26

(58) Field of Classification Search
CPC ........................ A61F 2/2418; A61B 17/0057
USPC ............... 623/2.18, 2.14, 1.24, 1.26; 606/213
See application file for complete search history.

(56) References Cited

U.S. PATENT DOCUMENTS

| 4,261,342 A | 4/1981 | Aranguren Duo |
| 4,892,541 A | 1/1990 | Alonso |

(Continued)

FOREIGN PATENT DOCUMENTS

| EP | 1 264 582 A2 | 12/2002 |
| WO | 99/30647 A1 | 6/1999 |

(Continued)

OTHER PUBLICATIONS

Alexander S. Geha, et al; "Replacement of Degenerated Mitral and Aortic Bioprostheses Without Explanation", Ann. Thorac Surg; Jun. 2001, vol. 72, pp. 1509-1514.

(Continued)

*Primary Examiner* — Alvin Stewart
(74) *Attorney, Agent, or Firm* — Ladas & Parry LLP

(57) ABSTRACT

Apparatus is described for use with a native heart valve of a subject, the apparatus including (1) a prosthetic valve support, comprising an upstream support portion, the upstream support portion having (a) a compressed configuration and an uncompressed configuration in which the upstream support portion has an inner perimeter that defines an opening; and (2) a prosthetic valve, advanceable into the opening defined by the upstream support portion, and intracorporeally couplable to the upstream support portion by being expanded within the opening defined by the upstream support portion, the apparatus being configured such that, when the prosthetic valve is expanded within the opening defined by the upstream support portion, the expansion of the prosthetic valve is restricted by the inner perimeter of the upstream support portion, without causing the prosthetic valve support to apply a radially-expansive force to the native annulus. Other embodiments are also described.

24 Claims, 24 Drawing Sheets

(56) References Cited

U.S. PATENT DOCUMENTS

| | | | |
|---|---|---|---|
| 5,108,420 A * | 4/1992 | Marks | 606/213 |
| 5,607,444 A * | 3/1997 | Lam | 606/194 |
| 5,607,470 A | 3/1997 | Milo | |
| 5,868,777 A * | 2/1999 | Lam | 606/194 |
| 6,042,607 A | 3/2000 | Williamson, IV et al. | |
| 6,074,417 A | 6/2000 | Peredo | |
| 6,113,612 A * | 9/2000 | Swanson et al. | 623/1.15 |
| 6,120,534 A * | 9/2000 | Ruiz | 623/1.19 |
| 6,152,937 A * | 11/2000 | Peterson et al. | 606/153 |
| 6,187,020 B1 | 2/2001 | Zegdi et al. | |
| 6,287,339 B1 | 9/2001 | Vazquez et al. | |
| 6,332,893 B1 | 12/2001 | Mortier et al. | |
| 6,391,036 B1 * | 5/2002 | Berg et al. | 606/151 |
| 6,402,780 B2 | 6/2002 | Williamson, IV et al. | |
| 6,409,755 B1 * | 6/2002 | Vrba | 623/1.2 |
| 6,419,696 B1 | 7/2002 | Ortiz et al. | |
| 6,428,550 B1 * | 8/2002 | Vargas et al. | 606/153 |
| 6,440,164 B1 | 8/2002 | DiMatteo et al. | |
| 6,458,153 B1 * | 10/2002 | Bailey et al. | 623/1.24 |
| 6,511,491 B2 * | 1/2003 | Grudem et al. | 606/153 |
| 6,530,952 B2 | 3/2003 | Vesely | |
| 6,540,782 B1 | 4/2003 | Snyders | |
| 6,558,418 B2 | 5/2003 | Carpentier et al. | |
| 6,602,263 B1 * | 8/2003 | Swanson et al. | 606/153 |
| 6,616,675 B1 * | 9/2003 | Evard et al. | 606/155 |
| 6,699,256 B1 * | 3/2004 | Logan et al. | 606/153 |
| 6,716,244 B2 | 4/2004 | Klaco | |
| 6,719,781 B1 * | 4/2004 | Kim | 623/1.13 |
| 6,730,118 B2 | 5/2004 | Spenser et al. | |
| 6,767,362 B2 | 7/2004 | Schreck | |
| 6,797,002 B2 | 9/2004 | Spence et al. | |
| 6,830,585 B1 * | 12/2004 | Artof et al. | 623/2.11 |
| 6,830,638 B2 * | 12/2004 | Boylan et al. | 148/563 |
| 6,960,217 B2 | 11/2005 | Bolduc | |
| 6,964,684 B2 | 11/2005 | Ortiz et al. | |
| 7,011,681 B2 | 3/2006 | Vesely | |
| 7,018,406 B2 | 3/2006 | Seguin et al. | |
| 7,041,132 B2 * | 5/2006 | Quijano et al. | 623/2.11 |
| 7,077,861 B2 | 7/2006 | Spence | |
| 7,101,395 B2 | 9/2006 | Tremulis et al. | |
| 7,172,625 B2 | 2/2007 | Shu et al. | |
| 7,198,646 B2 | 4/2007 | Figulla et al. | |
| 7,201,772 B2 * | 4/2007 | Schwammenthal et al. | 623/2.18 |
| 7,288,111 B1 * | 10/2007 | Holloway et al. | 623/1.15 |
| 7,335,213 B1 | 2/2008 | Hyde et al. | |
| 7,404,824 B1 | 7/2008 | Webler et al. | |
| 7,422,603 B2 | 9/2008 | Lane | |
| 7,429,269 B2 * | 9/2008 | Schwammenthal et al. | 623/2.14 |
| 7,442,204 B2 * | 10/2008 | Schwammenthal et al. | 623/1.24 |
| 7,445,630 B2 | 11/2008 | Lashinski | |
| 7,455,677 B2 * | 11/2008 | Vargas et al. | 606/153 |
| 7,455,688 B2 * | 11/2008 | Furst et al. | 623/1.31 |
| 7,462,162 B2 * | 12/2008 | Phan et al. | 604/8 |
| 7,481,838 B2 | 1/2009 | Carpentier et al. | |
| 7,510,575 B2 | 3/2009 | Spenser et al. | |
| 7,513,909 B2 | 4/2009 | Lane et al. | |
| 7,527,646 B2 * | 5/2009 | Rahdert et al. | 623/2.36 |
| 7,582,111 B2 * | 9/2009 | Krolik et al. | 623/1.32 |
| 7,585,321 B2 | 9/2009 | Cribier | |
| 7,632,302 B2 * | 12/2009 | Vreeman et al. | 623/1.16 |
| 7,708,775 B2 | 5/2010 | Rowe et al. | |
| 7,717,955 B2 | 5/2010 | Lane et al. | |
| 7,731,741 B2 * | 6/2010 | Eidenschink | 623/1.11 |
| 7,753,922 B2 | 7/2010 | Starksen | |
| 7,758,595 B2 | 7/2010 | Allen et al. | |
| 7,771,467 B2 | 8/2010 | Svensson | |
| 7,771,469 B2 | 8/2010 | Liddicoat | |
| 7,776,083 B2 | 8/2010 | Vesely | |
| 7,780,726 B2 | 8/2010 | Seguin | |
| 7,799,069 B2 * | 9/2010 | Bailey et al. | 623/1.26 |
| 7,803,181 B2 * | 9/2010 | Furst et al. | 623/1.31 |
| 7,837,727 B2 * | 11/2010 | Goetz et al. | 623/2.18 |
| 7,842,081 B2 * | 11/2010 | Yadin | 623/1.35 |
| 7,850,725 B2 * | 12/2010 | Vardi et al. | 623/1.15 |
| 7,871,432 B2 | 1/2011 | Bergin | |
| 7,871,436 B2 | 1/2011 | Ryan et al. | |
| 7,887,583 B2 | 2/2011 | Macoviak | |
| 7,892,281 B2 | 2/2011 | Seguin et al. | |
| 7,896,915 B2 * | 3/2011 | Guyenot et al. | 623/2.14 |
| 7,914,544 B2 | 3/2011 | Nguyen et al. | |
| 7,914,569 B2 | 3/2011 | Nguyen et al. | |
| 7,927,370 B2 | 4/2011 | Webler | |
| 7,947,072 B2 | 5/2011 | Yang et al. | |
| 7,947,075 B2 * | 5/2011 | Goetz et al. | 623/2.18 |
| 7,955,375 B2 | 6/2011 | Agnew | |
| 7,955,384 B2 | 6/2011 | Rafiee et al. | |
| 7,967,833 B2 | 6/2011 | Sterman et al. | |
| 7,967,857 B2 | 6/2011 | Lane | |
| 7,981,151 B2 | 7/2011 | Rowe | |
| 7,981,153 B2 | 7/2011 | Fogarty et al. | |
| 7,992,567 B2 | 8/2011 | Hirotsuka et al. | |
| 7,993,393 B2 | 8/2011 | Carpentier et al. | |
| 8,002,825 B2 | 8/2011 | Letac et al. | |
| 8,016,877 B2 | 9/2011 | Seguin et al. | |
| 8,016,882 B2 * | 9/2011 | Macoviak et al. | 623/2.36 |
| 8,021,420 B2 | 9/2011 | Dolan | |
| 8,021,421 B2 | 9/2011 | Fogarty et al. | |
| 8,029,518 B2 | 10/2011 | Goldfarb | |
| 8,029,564 B2 | 10/2011 | Johnson et al. | |
| 8,034,104 B2 | 10/2011 | Carpentier et al. | |
| 8,043,360 B2 * | 10/2011 | McNamara et al. | 623/1.15 |
| 8,048,140 B2 * | 11/2011 | Purdy | 623/1.13 |
| 8,048,153 B2 * | 11/2011 | Salahieh et al. | 623/2.11 |
| 8,052,741 B2 * | 11/2011 | Bruszewski et al. | 623/1.35 |
| 8,057,493 B2 | 11/2011 | Goldfarb et al. | |
| 8,057,532 B2 * | 11/2011 | Hoffman | 623/1.24 |
| 8,057,540 B2 | 11/2011 | Letac et al. | |
| 8,062,355 B2 * | 11/2011 | Figulla et al. | 623/2.1 |
| 8,062,359 B2 | 11/2011 | Marquez et al. | |
| 8,070,708 B2 * | 12/2011 | Rottenberg et al. | 604/9 |
| 8,070,800 B2 | 12/2011 | Lock | |
| 8,070,802 B2 * | 12/2011 | Lamphere et al. | 623/2.14 |
| 8,070,804 B2 | 12/2011 | Hyde et al. | |
| 8,075,611 B2 | 12/2011 | Millwee et al. | |
| 8,080,054 B2 | 12/2011 | Rowe | |
| 8,083,793 B2 | 12/2011 | Lane et al. | |
| 8,092,518 B2 | 1/2012 | Schreck | |
| 8,092,520 B2 | 1/2012 | Quadri | |
| 8,092,521 B2 | 1/2012 | Figulla et al. | |
| 8,105,377 B2 | 1/2012 | Liddicoat | |
| 8,118,866 B2 | 2/2012 | Herrmann et al. | |
| 8,136,218 B2 | 3/2012 | Millwee et al. | |
| 8,137,398 B2 | 3/2012 | Tuval et al. | |
| 8,142,492 B2 | 3/2012 | Forster et al. | |
| 8,142,494 B2 * | 3/2012 | Rahdert et al. | 623/2.36 |
| 8,142,496 B2 | 3/2012 | Berreklouw | |
| 8,142,497 B2 | 3/2012 | Friedman | |
| 8,147,504 B2 | 4/2012 | Ino et al. | |
| 8,157,852 B2 | 4/2012 | Bloom et al. | |
| 8,157,853 B2 | 4/2012 | Laske et al. | |
| 8,157,860 B2 * | 4/2012 | McNamara et al. | 623/1.26 |
| 8,163,014 B2 | 4/2012 | Lane et al. | |
| 8,167,894 B2 * | 5/2012 | Miles et al. | 606/139 |
| 8,167,932 B2 | 5/2012 | Bourang et al. | |
| 8,167,935 B2 | 5/2012 | McGuckin, Jr. | |
| 8,172,896 B2 * | 5/2012 | McNamara et al. | 623/1.26 |
| 8,177,836 B2 | 5/2012 | Lee et al. | |
| 8,182,528 B2 * | 5/2012 | Salahieh et al. | 623/2.11 |
| 8,211,169 B2 | 7/2012 | Lane et al. | |
| 8,221,492 B2 | 7/2012 | Case et al. | |
| 8,221,493 B2 * | 7/2012 | Boyle et al. | 623/1.24 |
| 8,226,710 B2 * | 7/2012 | Nguyen et al. | 623/2.18 |
| 8,231,670 B2 * | 7/2012 | Salahieh et al. | 623/2.11 |
| 8,236,045 B2 * | 8/2012 | Benichou et al. | 623/1.26 |
| 8,236,049 B2 * | 8/2012 | Rowe et al. | 623/2.11 |
| 8,252,042 B2 * | 8/2012 | McNamara et al. | 623/1.26 |
| 8,252,051 B2 * | 8/2012 | Chau et al. | 623/2.12 |
| 8,252,052 B2 * | 8/2012 | Salahieh et al. | 623/2.18 |
| 8,257,390 B2 * | 9/2012 | Carley et al. | 606/213 |
| 8,277,501 B2 * | 10/2012 | Chalekian et al. | 623/1.35 |
| 8,287,591 B2 | 10/2012 | Keidar et al. | |
| 8,298,280 B2 * | 10/2012 | Yadin et al. | 623/1.35 |
| 8,308,798 B2 * | 11/2012 | Pintor et al. | 623/2.18 |
| 8,317,853 B2 * | 11/2012 | Agnew | 623/1.24 |

(56) References Cited

U.S. PATENT DOCUMENTS

| | | | |
|---|---|---|---|
| 8,317,855 B2* | 11/2012 | Gregorich et al. | 623/1.35 |
| 8,323,335 B2* | 12/2012 | Rowe et al. | 623/2.11 |
| 8,328,868 B2* | 12/2012 | Paul et al. | 623/2.11 |
| 8,343,174 B2* | 1/2013 | Goldfarb et al. | 606/151 |
| 8,430,934 B2* | 4/2013 | Das | 623/23.72 |
| 8,449,625 B2* | 5/2013 | Campbell et al. | 623/1.26 |
| 8,628,571 B1* | 1/2014 | Hacohen et al. | 623/2.2 |
| 8,696,742 B2* | 4/2014 | Pintor et al. | 623/2.11 |
| 2001/0021872 A1 | 9/2001 | Bailey et al. | |
| 2003/0036791 A1 | 2/2003 | Philipp et al. | |
| 2003/0074052 A1* | 4/2003 | Besselink | 623/1.15 |
| 2003/0083742 A1 | 5/2003 | Spence et al. | |
| 2003/0105519 A1 | 6/2003 | Fasol et al. | |
| 2003/0158578 A1* | 8/2003 | Pantages et al. | 606/213 |
| 2004/0010272 A1 | 1/2004 | Manetakis et al. | |
| 2004/0039414 A1* | 2/2004 | Carley et al. | 606/213 |
| 2004/0093060 A1 | 5/2004 | Seguin et al. | |
| 2004/0122514 A1 | 6/2004 | Fogarty et al. | |
| 2004/0176839 A1 | 9/2004 | Huynh et al. | |
| 2004/0186565 A1 | 9/2004 | Schreck | |
| 2004/0186566 A1 | 9/2004 | Hindrichs et al. | |
| 2004/0210244 A1* | 10/2004 | Vargas et al. | 606/153 |
| 2004/0220593 A1 | 11/2004 | Greenhalgh | |
| 2004/0225354 A1 | 11/2004 | Allen et al. | |
| 2004/0260389 A1 | 12/2004 | Case et al. | |
| 2005/0004668 A1 | 1/2005 | Aklog et al. | |
| 2005/0021056 A1 | 1/2005 | St. Goar et al. | |
| 2005/0075731 A1* | 4/2005 | Artof et al. | 623/2.18 |
| 2005/0137688 A1 | 6/2005 | Salahieh et al. | |
| 2005/0137689 A1* | 6/2005 | Salahieh et al. | 623/2.11 |
| 2005/0137690 A1* | 6/2005 | Salahieh et al. | 623/2.11 |
| 2005/0137695 A1* | 6/2005 | Salahieh et al. | 623/2.11 |
| 2005/0143809 A1* | 6/2005 | Salahieh et al. | 623/2.11 |
| 2005/0197695 A1 | 9/2005 | Stacchino et al. | |
| 2005/0203549 A1 | 9/2005 | Realyvasquez | |
| 2005/0216079 A1 | 9/2005 | MaCoviak | |
| 2005/0234508 A1* | 10/2005 | Cummins et al. | 606/213 |
| 2005/0240200 A1* | 10/2005 | Bergheim | 606/108 |
| 2005/0251251 A1 | 11/2005 | Cribier | |
| 2005/0267573 A9* | 12/2005 | Macoviak et al. | 623/2.36 |
| 2006/0047297 A1 | 3/2006 | Case | |
| 2006/0135964 A1 | 6/2006 | Vesely | |
| 2006/0178740 A1 | 8/2006 | Stacchino et al. | |
| 2006/0190036 A1* | 8/2006 | Wendel et al. | 606/213 |
| 2006/0190038 A1* | 8/2006 | Carley et al. | 606/213 |
| 2006/0195184 A1 | 8/2006 | Lane et al. | |
| 2006/0201519 A1 | 9/2006 | Frazier et al. | |
| 2006/0241656 A1 | 10/2006 | Starksen et al. | |
| 2006/0241748 A1 | 10/2006 | Lee et al. | |
| 2006/0247680 A1* | 11/2006 | Amplatz et al. | 606/213 |
| 2006/0253191 A1 | 11/2006 | Salahieh et al. | |
| 2006/0259136 A1 | 11/2006 | Nguyen et al. | |
| 2006/0271166 A1 | 11/2006 | Thill et al. | |
| 2006/0271171 A1 | 11/2006 | McQuinn et al. | |
| 2006/0287719 A1 | 12/2006 | Rowe et al. | |
| 2007/0016288 A1 | 1/2007 | Gurskis et al. | |
| 2007/0027549 A1 | 2/2007 | Godin | |
| 2007/0038295 A1 | 2/2007 | Case et al. | |
| 2007/0043435 A1 | 2/2007 | Seguin et al. | |
| 2007/0112422 A1 | 5/2007 | Dehdashtian | |
| 2007/0118151 A1 | 5/2007 | Davidson | |
| 2007/0162103 A1* | 7/2007 | Case et al. | 623/1.13 |
| 2007/0162107 A1 | 7/2007 | Haug et al. | |
| 2007/0162111 A1 | 7/2007 | Fukamachi et al. | |
| 2007/0173932 A1 | 7/2007 | Cali et al. | |
| 2007/0198097 A1* | 8/2007 | Zegdi | 623/23.68 |
| 2007/0213813 A1 | 9/2007 | Von Segesser et al. | |
| 2007/0225759 A1* | 9/2007 | Thommen et al. | 606/213 |
| 2007/0225760 A1* | 9/2007 | Moszner et al. | 606/213 |
| 2007/0233186 A1* | 10/2007 | Meng | 606/213 |
| 2007/0233237 A1* | 10/2007 | Krivoruchko | 623/2.11 |
| 2007/0239272 A1* | 10/2007 | Navia et al. | 623/2.36 |
| 2007/0255400 A1 | 11/2007 | Parravicini et al. | |
| 2008/0004688 A1 | 1/2008 | Spenser et al. | |
| 2008/0004697 A1 | 1/2008 | Lichtenstein et al. | |
| 2008/0051703 A1 | 2/2008 | Thornton et al. | |
| 2008/0071363 A1 | 3/2008 | Tuval et al. | |
| 2008/0071366 A1 | 3/2008 | Tuval et al. | |
| 2008/0071369 A1 | 3/2008 | Tuval et al. | |
| 2008/0077235 A1 | 3/2008 | Kirson | |
| 2008/0086164 A1 | 4/2008 | Rowe et al. | |
| 2008/0086204 A1 | 4/2008 | Rankin | |
| 2008/0161910 A1 | 7/2008 | Revuelta et al. | |
| 2008/0167714 A1 | 7/2008 | St. Goar et al. | |
| 2008/0188929 A1 | 8/2008 | Schreck | |
| 2008/0195200 A1 | 8/2008 | Vidlund et al. | |
| 2008/0208332 A1 | 8/2008 | Lamphere et al. | |
| 2008/0221672 A1 | 9/2008 | Lamphere et al. | |
| 2008/0243245 A1 | 10/2008 | Thambar et al. | |
| 2008/0262609 A1 | 10/2008 | Gross et al. | |
| 2008/0281411 A1 | 11/2008 | Berreklouw | |
| 2009/0005863 A1* | 1/2009 | Goetz et al. | 623/2.18 |
| 2009/0054969 A1 | 2/2009 | Salahieh et al. | |
| 2009/0099650 A1 | 4/2009 | Bolduc et al. | |
| 2009/0171363 A1 | 7/2009 | Chocron | |
| 2009/0177278 A1 | 7/2009 | Spence | |
| 2009/0210052 A1 | 8/2009 | Forster et al. | |
| 2009/0222081 A1 | 9/2009 | Linder et al. | |
| 2009/0241656 A1 | 10/2009 | Jacquemin | |
| 2009/0264994 A1 | 10/2009 | Saadat | |
| 2009/0306768 A1 | 12/2009 | Quadri | |
| 2009/0319037 A1 | 12/2009 | Rowe et al. | |
| 2010/0036479 A1* | 2/2010 | Hill et al. | 623/1.15 |
| 2010/0076548 A1 | 3/2010 | Konno | |
| 2010/0114299 A1 | 5/2010 | Ben Muvhar et al. | |
| 2010/0131054 A1 | 5/2010 | Tuval et al. | |
| 2010/0137979 A1 | 6/2010 | Tuval et al. | |
| 2010/0160958 A1* | 6/2010 | Clark | 606/213 |
| 2010/0161036 A1* | 6/2010 | Pintor et al. | 623/1.26 |
| 2010/0161042 A1 | 6/2010 | Maisano et al. | |
| 2010/0174363 A1 | 7/2010 | Castro | |
| 2010/0179643 A1 | 7/2010 | Shalev | |
| 2010/0179648 A1 | 7/2010 | Richter et al. | |
| 2010/0179649 A1 | 7/2010 | Richter et al. | |
| 2010/0217382 A1 | 8/2010 | Chau et al. | |
| 2010/0222810 A1* | 9/2010 | DeBeer et al. | 606/213 |
| 2010/0228285 A1* | 9/2010 | Miles et al. | 606/213 |
| 2010/0234940 A1 | 9/2010 | Dolan | |
| 2010/0249908 A1 | 9/2010 | Chau et al. | |
| 2010/0249917 A1 | 9/2010 | Zhang | |
| 2010/0262232 A1 | 10/2010 | Annest | |
| 2010/0280606 A1 | 11/2010 | Naor | |
| 2010/0324595 A1* | 12/2010 | Linder et al. | 606/213 |
| 2011/0004296 A1 | 1/2011 | Lutter et al. | |
| 2011/0015729 A1 | 1/2011 | Jimenez et al. | |
| 2011/0015731 A1 | 1/2011 | Carpentier | |
| 2011/0022165 A1 | 1/2011 | Oba et al. | |
| 2011/0040374 A1 | 2/2011 | Goetz et al. | |
| 2011/0040375 A1 | 2/2011 | Letac et al. | |
| 2011/0046662 A1* | 2/2011 | Moszner et al. | 606/213 |
| 2011/0054466 A1 | 3/2011 | Rothstein et al. | |
| 2011/0054494 A1 | 3/2011 | Taylor | |
| 2011/0054598 A1 | 3/2011 | Johnson | |
| 2011/0082538 A1 | 4/2011 | Dahlgren et al. | |
| 2011/0087322 A1 | 4/2011 | Letac et al. | |
| 2011/0093063 A1 | 4/2011 | Schreck | |
| 2011/0106247 A1 | 5/2011 | Miller et al. | |
| 2011/0112625 A1 | 5/2011 | Ben-Muvhar et al. | |
| 2011/0112632 A1 | 5/2011 | Chau et al. | |
| 2011/0118830 A1 | 5/2011 | Liddicoat et al. | |
| 2011/0125257 A1 | 5/2011 | Seguin et al. | |
| 2011/0125258 A1 | 5/2011 | Centola | |
| 2011/0137397 A1 | 6/2011 | Chau et al. | |
| 2011/0137409 A1 | 6/2011 | Yang et al. | |
| 2011/0137410 A1 | 6/2011 | Hacohen | |
| 2011/0166636 A1 | 7/2011 | Rowe | |
| 2011/0172784 A1 | 7/2011 | Richter et al. | |
| 2011/0178597 A9* | 7/2011 | Navia et al. | 623/2.18 |
| 2011/0184510 A1 | 7/2011 | Maisano et al. | |
| 2011/0190877 A1 | 8/2011 | Lane et al. | |
| 2011/0190879 A1 | 8/2011 | Bobo et al. | |
| 2011/0202076 A1 | 8/2011 | Richter | |
| 2011/0208283 A1 | 8/2011 | Rust | |
| 2011/0208293 A1* | 8/2011 | Tabor | 623/1.26 |

(56) References Cited

U.S. PATENT DOCUMENTS

| | | |
|---|---|---|
| 2011/0208298 A1 | 8/2011 | Tuval et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1* | 9/2011 | Hacohen .............. 623/2.18 |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282440 A1 | 11/2011 | Cao et al. |
| 2011/0283514 A1 | 11/2011 | Fogarty et al. |
| 2011/0288634 A1 | 11/2011 | Tuval et al. |
| 2011/0295363 A1 | 12/2011 | Girard et al. |
| 2011/0301688 A1 | 12/2011 | Dolan |
| 2011/0301701 A1 | 12/2011 | Padala et al. |
| 2011/0301702 A1 | 12/2011 | Rust et al. |
| 2011/0313452 A1* | 12/2011 | Carley et al. ............. 606/213 |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0078353 A1 | 3/2012 | Quadri et al. |
| 2012/0078357 A1 | 3/2012 | Conklin |
| 2012/0083832 A1* | 4/2012 | Delaloye et al. .......... 606/213 |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101572 A1 | 4/2012 | Kovalsky et al. |
| 2012/0123530 A1 | 5/2012 | Carpentier et al. |
| 2012/0136434 A1 | 5/2012 | Carpentier et al. |
| 2012/0150218 A1* | 6/2012 | Sandgren et al. .......... 606/213 |
| 2012/0197292 A1* | 8/2012 | Chin-Chen et al. ........ 606/213 |
| 2012/0283824 A1* | 11/2012 | Lutter et al. ............. 623/2.18 |
| 2012/0290062 A1* | 11/2012 | McNamara et al. ......... 623/1.2 |
| 2012/0310328 A1 | 12/2012 | Olson et al. |
| 2012/0323316 A1* | 12/2012 | Chau et al. .............. 623/2.18 |
| 2013/0035759 A1 | 2/2013 | Gross et al. |
| 2013/0261737 A1 | 10/2013 | Costello |
| 2013/0304197 A1 | 11/2013 | Buchbinder et al. |
| 2014/0005778 A1 | 1/2014 | Buchbinder et al. |
| 2014/0052237 A1 | 2/2014 | Lane et al. |
| 2014/0194983 A1 | 7/2014 | Kovalsky et al. |

FOREIGN PATENT DOCUMENTS

| | | |
|---|---|---|
| WO | 00/47139 A1 | 8/2000 |
| WO | 01/62189 A1 | 8/2001 |
| WO | 01/87190 A2 | 11/2001 |
| WO | 2006/054930 A1 | 5/2006 |
| WO | 2008/013915 A3 | 1/2008 |
| WO | 2009/033469 A1 | 3/2009 |
| WO | 2009/053497 A1 | 4/2009 |
| WO | 2010/006627 A1 | 1/2010 |
| WO | 2011/069048 A2 | 6/2011 |
| WO | 2011/106137 A1 | 9/2011 |
| WO | 2011/111047 A2 | 9/2011 |
| WO | 2011/137531 A1 | 11/2011 |
| WO | 2011/143263 A2 | 11/2011 |
| WO | 2012/011108 A2 | 1/2012 |
| WO | 2013/021374 A2 | 2/2013 |
| WO | 2013/021375 A2 | 2/2013 |
| WO | 2013/078497 A1 | 6/2013 |
| WO | 2013/128436 A1 | 9/2013 |

OTHER PUBLICATIONS

J. Jansen, et al; "Detachable Shape-Memory Sewing Ring for Heart Valves", Artificial Organs, vol. 16, Issue 3, pp. 294-297, Jun. 1992 an abstract only.

Frank Langer, et al; "Ring plus String: Papillary muscle repositioning as an adjunctive repair technique for ischemis mitral regurgitation", The Journal of Thoracic and Cardiovascular Surgery, vol. 133, pp. 247-249, Jan. 2007.

Frank Langer, et al; "Ring+String Successful Repair Technique for Ischemic Mitral Regurgitation with Severe Leaflet Tethering", Circulation 120[Suppl 1]: pp. S85-S91; Sep. 2009.

John G Webb MD, et al; "Transcatheter Valve-in-Valve Implantation for Failed Bioprosthetic Heart Valves", Circulation, Apr. 2010; vol. 121: pp. 1848-1857.

International Preliminary Report on Patentability dated Sep. 11, 2012; PCT/IL2011/000231.

ISR & Written Opinion dated Oct. 13, 2011; PCT/IL11/00231.

ISR & Written Opinion dated Dec. 5, 2011; PCT/IL11/00582.

ISR & Written Opinion dated Feb. 6, 2013; PCT/IL12/00292.

ISR & Written Opinion dated Feb. 6, 2013; PCT/IL12/00293.

U.S. Appl. No. 61/492,449, filed Jun. 2, 2011.

U.S. Appl. No. 61/515,372, filed Aug. 5, 2011.

U.S. Appl. No. 61/525,281, filed Aug. 19, 2011.

U.S. Appl. No. 61/537,276, filed Sep. 21, 2011.

U.S. Appl. No. 61/555,160, filed Nov. 3, 2011.

U.S. Appl. No. 61/588,892, filed Jan. 20, 2012.

USPTO NFOA dated May 29, 2012 in connection with U.S. Appl. No. 12/840,463.

USPTO FOA dated Feb. 15, 2013 in conncection with U.S. Appl. No. 12/840,463.

USPTO NFOA dated Nov. 28, 2012 in connection with U.S. Appl. No. 12/961,721.

USPTO NFOA dated Nov. 23, 2012 in connection with U.S. Appl. No. 13/033,852.

USPTO FOA dated Jul. 23, 2013 in connection with U.S. Appl. No. 12/961,721.

USPTO NFOA dated Aug. 2, 2013 in connection with U.S. 13/033,852.

USPTO FOA dated Jul. 18, 2013 in connection with U.S. 13/044,694.

International Preliminary Report on Patentability dated Dec. 2, 2013; PCT/IL2011/000582.

USPTO NFOA dated Jun. 17, 2014 in connection with U.S. Appl. No. 12/961,721.

USPTO NFOA dated Jul. 2, 2014 in connection with U.S. Appl. No. 13/811,308.

USPTO NFOA dated Jul. 3, 2014 in connection with U.S. Appl. No. 13/033,852.

Invitation to Pay Additional Fees; PCT/IL2014/050087.

* cited by examiner

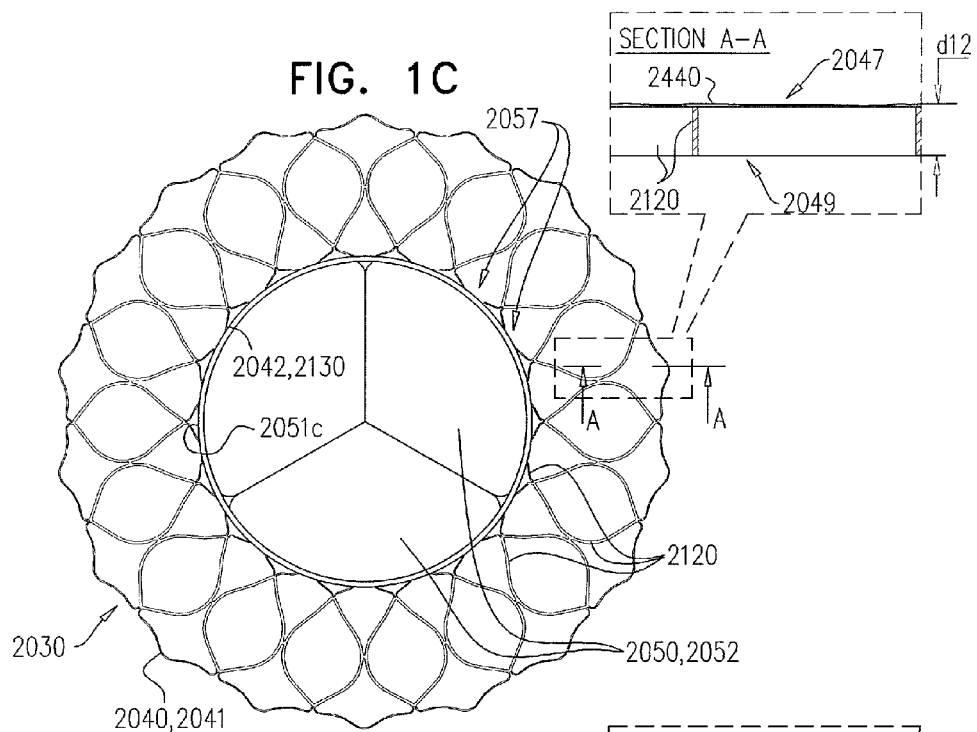
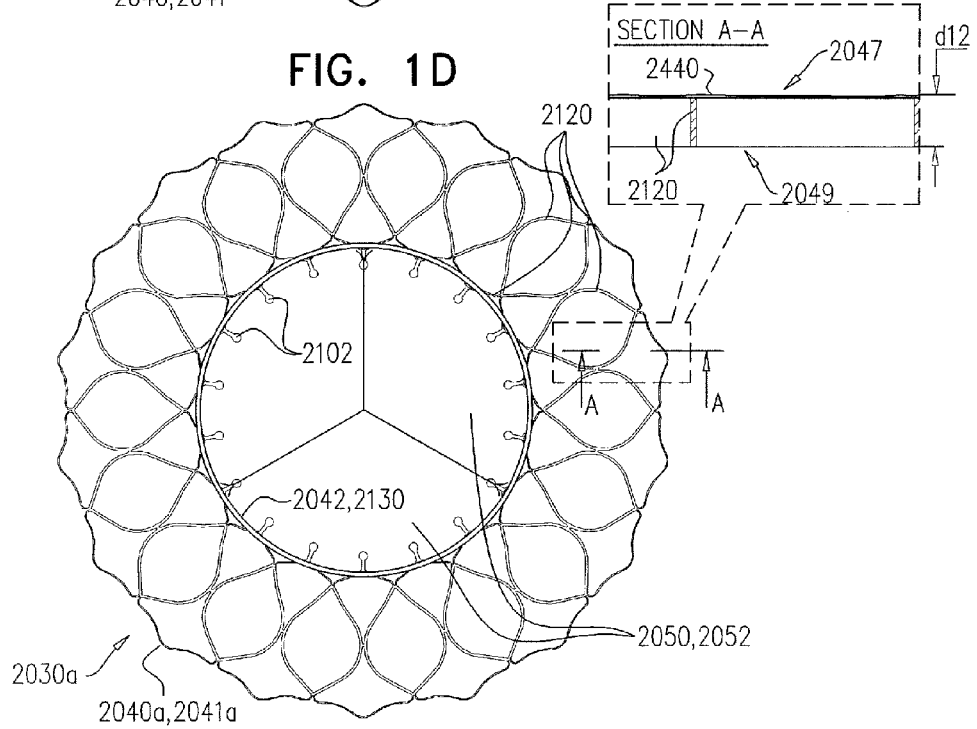

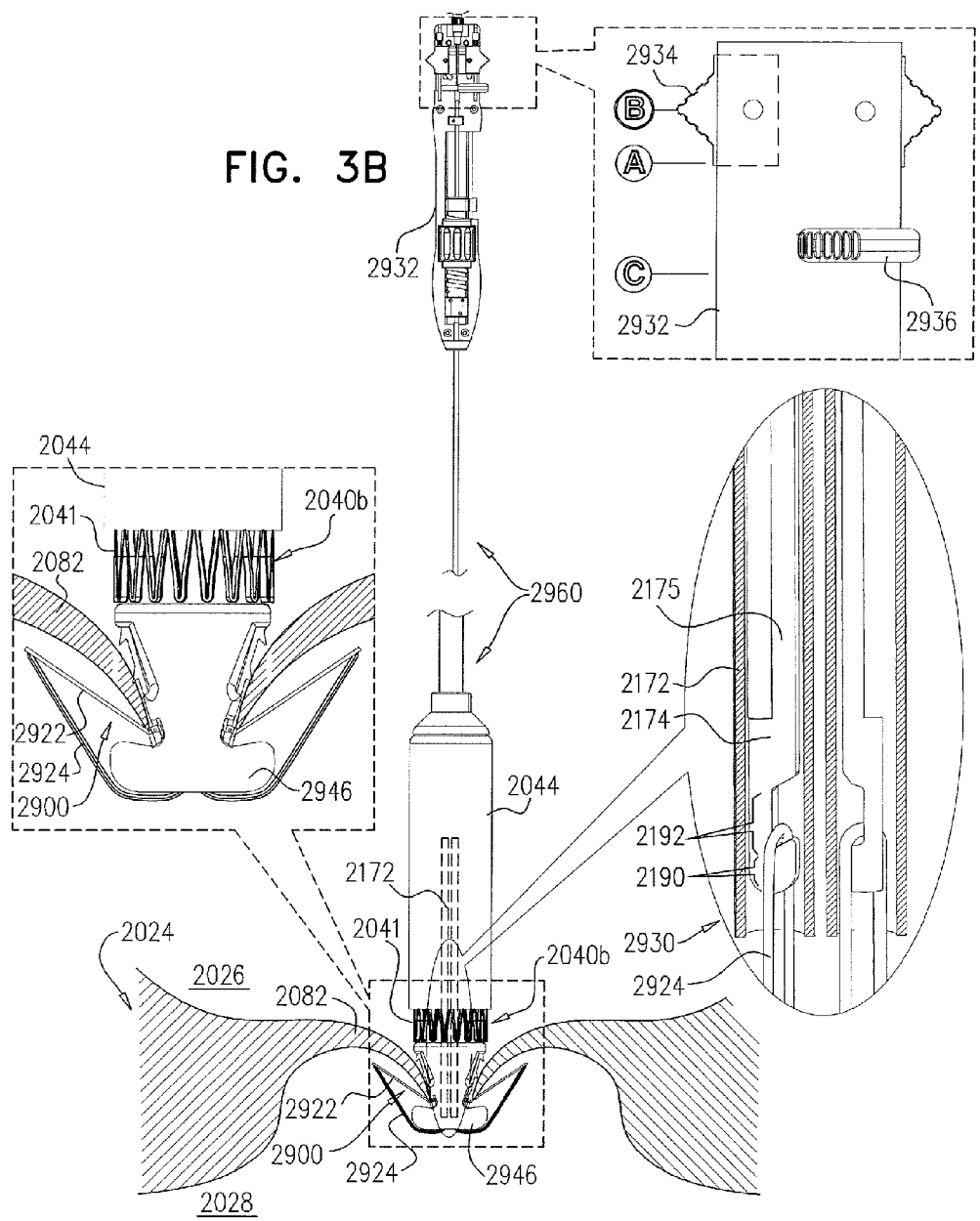

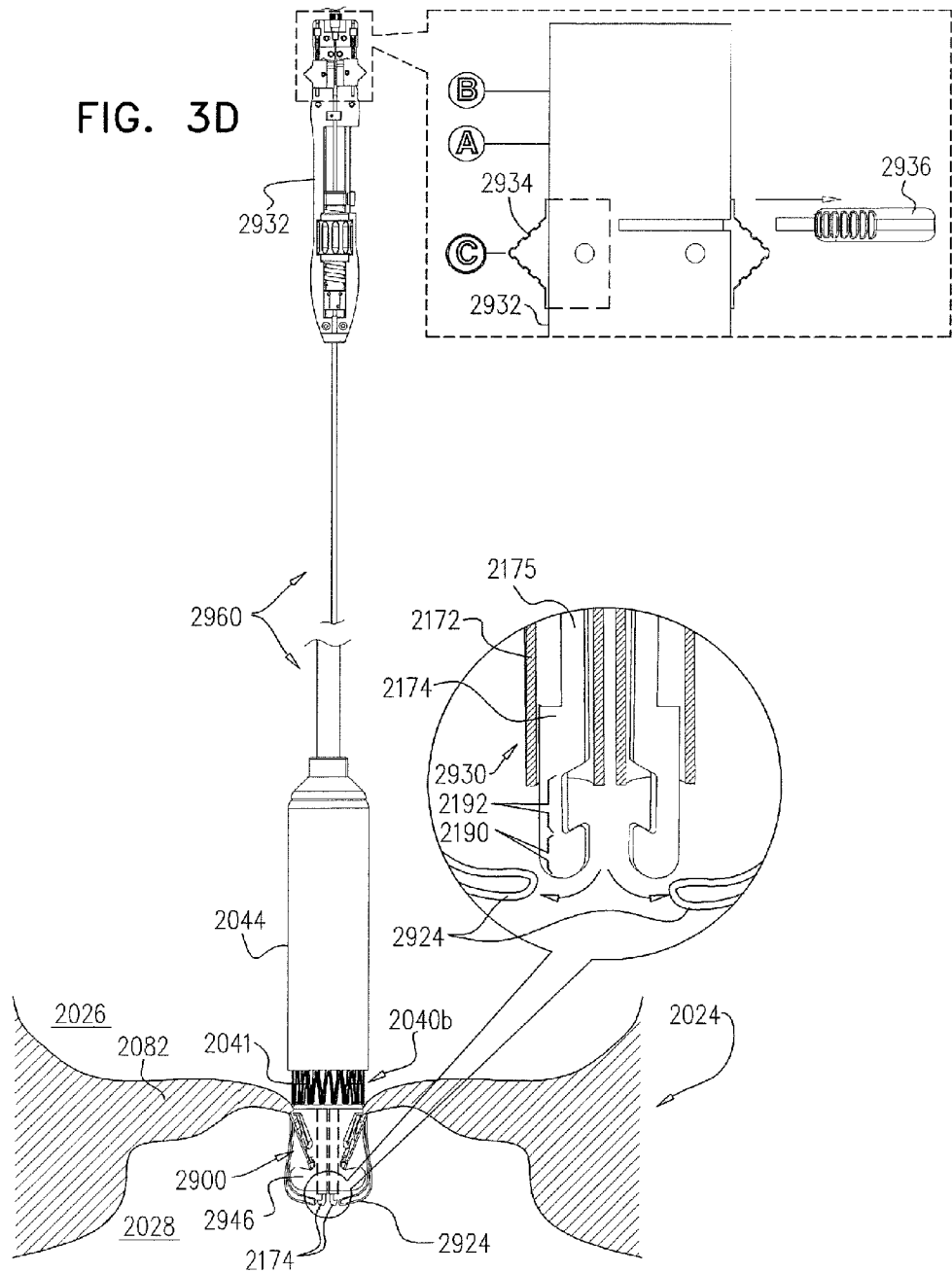

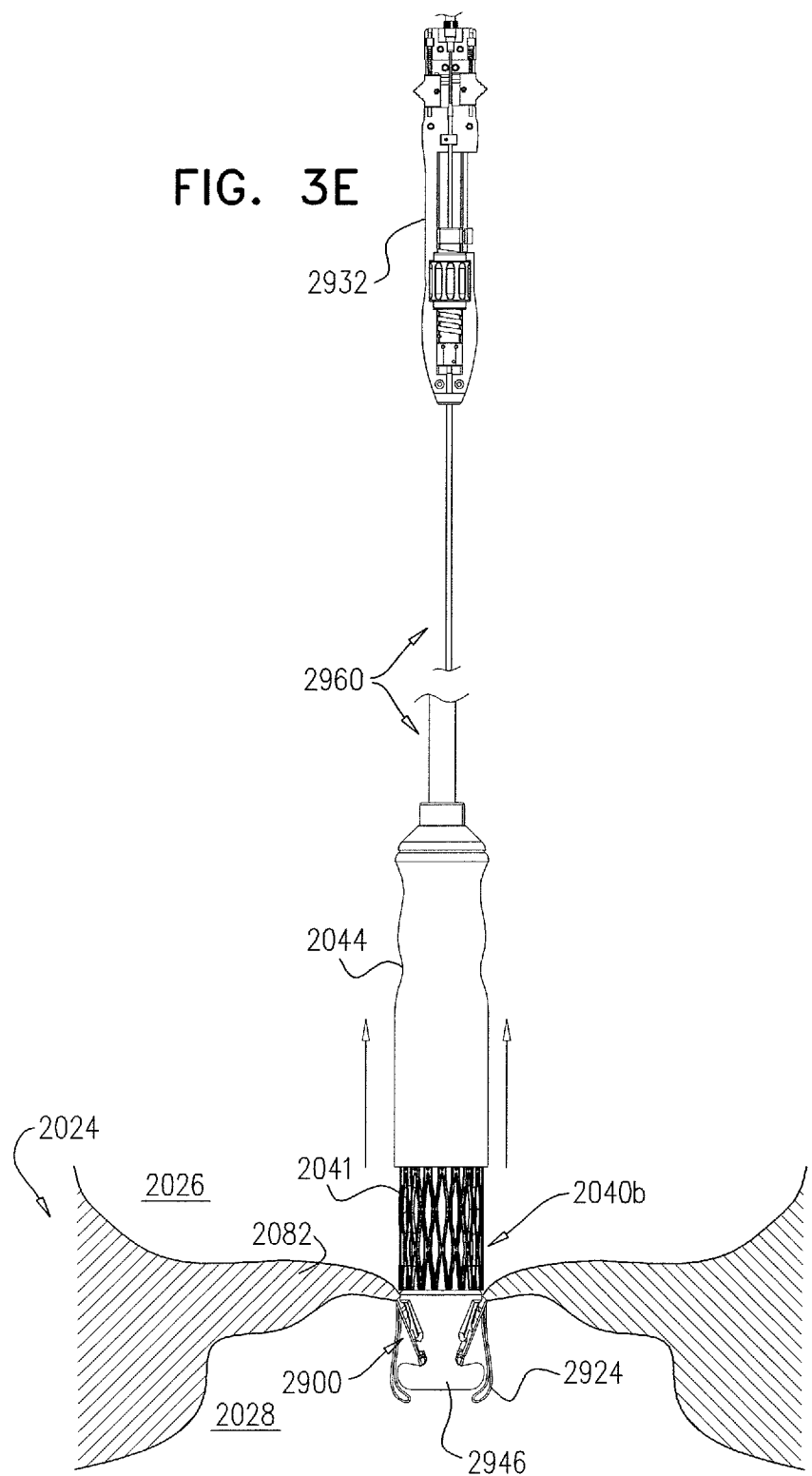

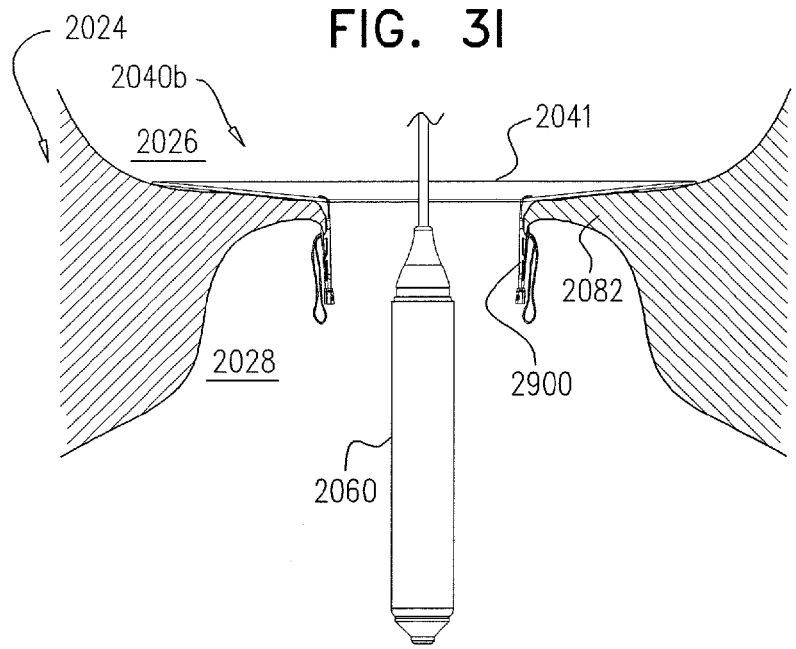
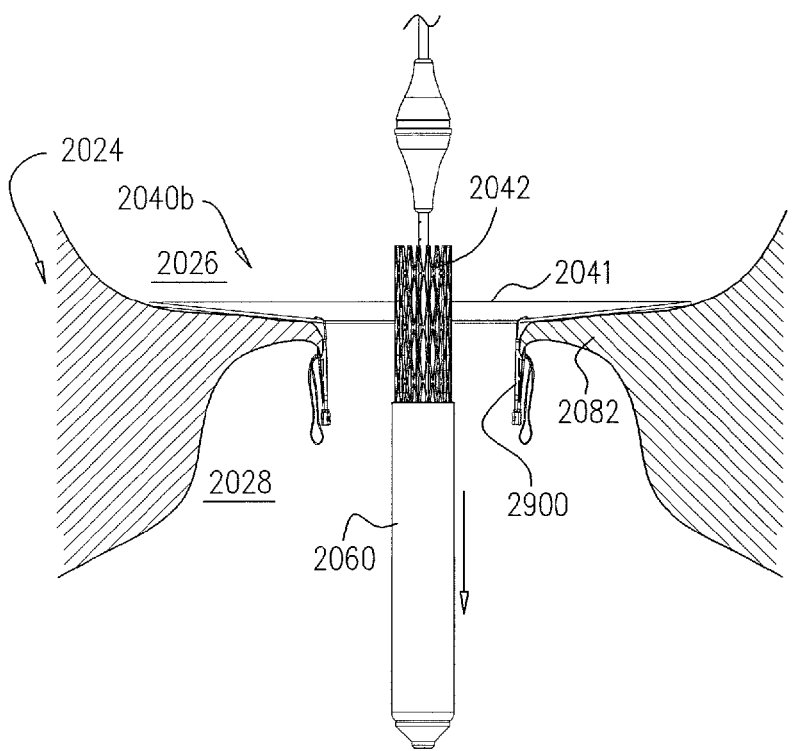

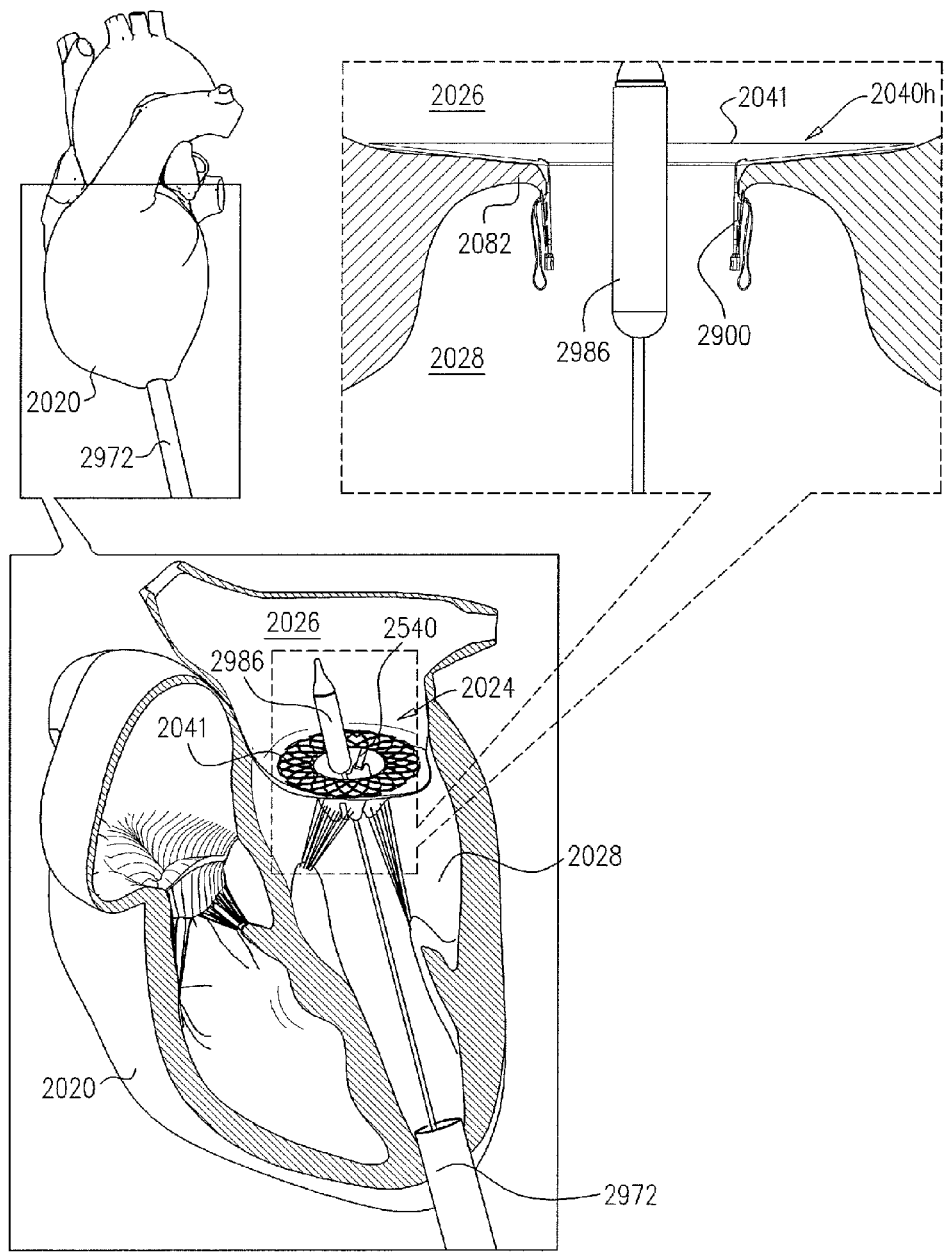

TECHNIQUES FOR PERCUTANEOUS MITRAL VALVE REPLACEMENT AND SEALING

CROSS-REFERENCES TO RELATED APPLICATIONS

The present application is related to, and claims priority from, U.S. Provisional Application 61/515,372 filed Aug. 5, 2011, U.S. Provisional Application 61/525,281 filed Aug. 19, 2011, U.S. Provisional Application 61/537,276, filed Sep. 21, 2011, U.S. Provisional Application 61/555,160, filed Nov. 3, 2011, and U.S. Provisional Application 61/588,892, filed Jan. 20, 2012, which are incorporated herein by reference.

FIELD OF THE INVENTION

Some applications of the present invention relate in general to valve replacement. More specifically, some applications of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications of the invention, a prosthetic valve support, shaped to define an opening, is implanted at a native heart valve of a subject, such that an upstream support portion of the prosthetic valve support is disposed against an upstream side of the native valve (e.g., an upstream side of the native valve annulus). A prosthetic valve is subsequently (e.g., after a duration) coupled to the prosthetic valve support by expanding the prosthetic valve in the opening defined by the prosthetic valve support. For some applications, the native heart valve includes an atrioventricular valve (e.g., a mitral valve or a tricuspid valve). For some applications, the native heart valve includes a semilunar valve (e.g., an aortic valve or a pulmonary valve).

For some applications of the invention, the prosthetic valve support is configured to be couplable to the native heart valve such that the heart of the subject is able to continue pumping blood sufficiently to support physiological systems of the subject for at least the duration between implanting the prosthetic valve support and implanting the prosthetic valve. For some applications of the invention, the prosthetic valve support comprises one or more clips, configured to couple the prosthetic valve support to leaflets of the native valve. For some applications, the clips are configured to couple the prosthetic valve support to the leaflets without eliminating native blood flow regulation functionality of the native valve. For some applications of the invention, the prosthetic valve support comprises a stabilizing element, disposed downstream of the prosthetic valve support, and shaped to define an aperture.

There is therefore provided, in accordance with an application of the present invention, apparatus for use with a prosthetic valve for implantation at a native valve of a heart of a subject, the apparatus including an upstream support portion, the upstream support portion:

(a) having a compressed configuration in which the support is transcatheterally deliverable to the native valve and in which the upstream support portion has a generally cylindrical shape, the cylindrical shape having a downstream end and an upstream end, each end having a perimeter, each perimeter of the cylindrical shape having a length, (b) having an uncompressed configuration in which the upstream support portion:
  is configured to be placed against an upstream side of the native valve, is shaped to define an opening,
  has an outer perimeter and an inner perimeter, and (c) being movable from the compressed configuration to the uncompressed configuration, the apparatus being configured such that, when the upstream support portion moves from the compressed configuration to the uncompressed configuration thereof:
  the perimeter of the downstream end of the upstream support portion in the compressed configuration thereof becomes the inner perimeter of the upstream support portion in the uncompressed configuration thereof, and
  the perimeter of the upstream end of the upstream support portion in the compressed configuration thereof becomes the outer perimeter of the upstream support portion in the uncompressed configuration thereof.

In an application, the apparatus is configured such that, when the upstream support portion moves from the compressed configuration to the uncompressed configuration thereof, the length of the perimeter of the upstream end of the upstream support portion in the compressed configuration thereof increases more than does the length of the perimeter of the downstream end of the upstream support portion in the compressed configuration thereof.

In an application, the upstream support portion, in the uncompressed configuration thereof, is generally annular.

In an application, the upstream support portion is shaped such that, in the uncompressed configuration thereof, the opening defined by the inner perimeter of the upstream support portion has a shape selected from the group consisting of: generally circular, elliptical, and oval.

In an application, the upstream support portion is configured to be placed against an upstream side of a mitral valve of the subject.

In an application, the upstream support portion is configured to be placed against an upstream side of a tricuspid valve of the subject.

In an application, the upstream support portion is configured to be placed against an upstream side of a pulmonary valve of the subject.

In an application, the upstream support portion is configured to be placed against an upstream side of an aortic valve of the subject.

In an application, the length of the outer perimeter is at least 10% greater than the length of the inner perimeter.

In an application, the length of the outer perimeter is at least 50% greater than the length of the inner perimeter.

In an application, the length of the outer perimeter is at least 80% greater than the length of the inner perimeter.

In an application, the inner perimeter of the upstream support portion is configured to be coupled to the prosthetic valve.

In an application, the inner perimeter of the upstream support portion is configured to be coupled to the prosthetic valve by the prosthetic valve being expanded within the opening defined by the inner perimeter.

In an application, in the uncompressed configuration thereof, any portion of the apparatus that circumscribes a space that has a perimeter greater than 60 mm has a depth of less than 2 mm.

In an application, in the uncompressed configuration thereof, any portion of the apparatus that circumscribes a space that has a perimeter greater than 60 mm has a depth of between 0.3 mm and 2 mm.

In an application, the upstream support portion is shaped such that the opening defined by the inner perimeter of the upstream support portion has a depth, and has a diameter that is more than 4 times greater than the depth.

In an application, the upstream support portion is shaped such that the diameter of the opening is more than 6 times greater than the depth of the opening.

In an application, the upstream support portion is shaped such that the diameter of the opening is more than 10 times greater than the depth of the opening.

In an application, the length of the inner perimeter is between 62 and 105 mm.

In an application, the length of the inner perimeter is between 65 and 80 mm.

In an application, the length of the inner perimeter is between 75 and 80 mm.

In an application, the length of the outer perimeter is between 125 and 190 mm.

In an application, the length of the outer perimeter is between 140 and 170 mm.

In an application, the length of the outer perimeter is between 140 and 150 mm.

In an application, the inner perimeter has a depth of less than 5 mm.

In an application, the depth of the inner perimeter is less than 2 mm.

In an application, the depth of the inner perimeter is between 0.3 mm and 2 mm.

In an application, the opening defined by the inner perimeter of the upstream support portion in the uncompressed configuration thereof, has a greatest diameter of between 20 and 35 mm.

In an application, the greatest diameter of the opening defined by the inner perimeter of the upstream support portion in the uncompressed configuration thereof, is between 23 and 32 mm.

In an application, the greatest diameter of the opening defined by the inner perimeter of the upstream support portion in the uncompressed configuration thereof, is between 25 and 30 mm.

In an application, the apparatus further includes at least one clip, the clip including a plurality of clip arms and configured to be coupled to the upstream support portion to the native valve.

In an application, the clip is articulatably coupled to the upstream support portion.

In an application, the clip has an open configuration and a closed configuration, and is movable between the open and closed configurations irrespective of a state of deployment of the upstream support portion.

There is further provided, in accordance with an application of the present invention, apparatus for use with a native heart valve of a subject, the native heart valve having a native annulus, the apparatus including:

a prosthetic valve support, including an upstream support portion, the upstream support portion having:
  a compressed configuration in which the upstream support portion is generally cylindrical, and is transcatheterally deliverable to the native valve, and
  an uncompressed configuration in which the upstream support portion:
    is configured to be placed against an upstream side of the native heart valve, and
    has an inner perimeter that defines an opening; and
a prosthetic valve:
  having a compressed configuration in which the prosthetic valve is transcatheterally deliverable to the native valve, and advanceable into the opening defined by the upstream support portion, and
  being intracorporeally couplable to the upstream support portion by being expanded,
the apparatus being configured such that, when the prosthetic valve is expanded, the expansion of the prosthetic valve is restricted by the prosthetic valve support, without causing the prosthetic valve support to apply a radially-expansive force to the native annulus.

In an application:
the upstream support portion, in the compressed configuration thereof, has an upstream end and a downstream end, each end having a perimeter, each perimeter having a length, and
the upstream support portion is configured such that, when the upstream support portion moves from the compressed configuration toward the uncompressed configuration thereof:
  the perimeter of the downstream end of the upstream support portion in the compressed configuration thereof becomes the inner perimeter of the upstream support portion in the uncompressed configuration thereof, and
  the perimeter of the upstream end of the upstream support portion in the compressed configuration thereof becomes an outer perimeter of the upstream support portion in the uncompressed configuration thereof.

In an application, the prosthetic valve support is configured to be placed against an upstream side of a mitral valve of the subject.

In an application, the prosthetic valve support is configured to be placed against an upstream side of a tricuspid valve of the subject.

In an application, the prosthetic valve support is configured to be placed against an upstream side of a pulmonary valve of the subject.

In an application, the prosthetic valve support is configured to be placed against an upstream side of an aortic valve of the subject.

In an application, the prosthetic valve includes one or more prosthetic valve leaflets, configured to regulate flow of blood through the prosthetic valve.

In an application, the prosthetic valve includes a ball, configured to regulate flow of blood through the prosthetic valve.

In an application, the prosthetic valve is intracorporeally couplable to the upstream support portion by being expanded within the opening defined by the inner perimeter of the upstream support portion.

In an application, the apparatus is configured such that, when the prosthetic valve is expanded, the expansion of the prosthetic valve is restricted by the inner perimeter of the upstream support portion.

In an application:

in the uncompressed configuration thereof, the upstream support portion has an upstream side and a downstream side, and a total height from the upstream side to the downstream side, the prosthetic valve has an upstream end and a downstream end, and a height from the upstream end to the downstream end, and the height of the prosthetic valve is at least 1.5 times greater than the total height of the upstream support portion.

In an application, the height of the prosthetic valve is at least 3 times greater than the total height of the upstream support portion.

In an application, the height of the prosthetic valve is at least 5 times greater than the total height of the upstream support portion.

In an application:

the upstream support portion has an upstream side and a downstream side, and the opening defined by the upstream support portion has a depth from the upstream side to the downstream side, the prosthetic valve has an upstream end and a downstream end, and a height from the upstream end to the downstream end, and the height of the prosthetic valve is at least 1.5 times greater than the depth of the opening defined by the upstream support portion.

In an application, the height of the prosthetic valve is at least 3 times greater than the depth of the opening defined by the upstream support portion.

In an application, the height of the prosthetic valve is at least 5 times greater than the depth of the opening defined by the upstream support portion.

In an application, the prosthetic valve, in the compressed configuration thereof, is generally cylindrical and has a perimeter, and the prosthetic valve has a fully uncompressed configuration in which the prosthetic valve is generally cylindrical and has a perimeter, each perimeter having a length, and the length of the perimeter of the prosthetic valve in the fully uncompressed configuration being greater than the length of the perimeter of the prosthetic valve in the compressed configuration.

In an application, the inner perimeter of the upstream support portion has a length, and the length of the perimeter of the prosthetic valve in the fully uncompressed configuration thereof is more than 1 mm greater than the length of the inner perimeter of the upstream support portion.

In an application, the apparatus is configured such that, when the prosthetic valve is expanded, the expansion of the prosthetic valve is restricted by the inner perimeter of the upstream support portion such that the prosthetic valve has a perimeter that has a length that is more than 1 mm shorter than the length of the perimeter of the prosthetic valve in the fully uncompressed configuration thereof.

In an application, the length of the inner perimeter of the opening defined by the upstream support portion is between 62 and 105 mm.

In an application, the opening defined by the upstream support portion has a greatest diameter of between 20 and 35 mm.

In an application, the prosthetic valve support further includes a stabilizing element, shaped to define an aperture.

In an application, the stabilizing element is configured to facilitate coupling of the prosthetic valve to the prosthetic valve support.

In an application, the stabilizing element is configured to facilitate coupling of the prosthetic valve to the prosthetic valve support by the prosthetic valve being expanded in the aperture defined by the stabilizing element.

In an application, the inner perimeter is defined by a free inner edge of the upstream support portion.

In an application, the inner perimeter is defined by a curved or folded edge of the upstream support portion.

In an application, the curved or folded edge of the upstream support portion has a radius of curvature that is less than 2.5 mm.

In an application, the curved or folded edge of the upstream support portion has a radius of curvature that is less than 1 mm.

In an application, the upstream support portion and the prosthetic valve include respective lattice structures, each lattice structure defining a plurality of struts, and a plurality of voids between the struts.

In an application, the lattice structure of the prosthetic valve support defines a number of inwardly-protruding ridges, and the lattice structure of the prosthetic valve defines a number of circumferential voids.

In an application, the prosthetic valve support defines a number of inwardly-protruding ridges that is equal to the number of circumferential voids defined by the prosthetic valve at at least one transverse plane of the prosthetic valve.

In an application, the prosthetic valve is intracorporeally couplable to the support by expanding the prosthetic valve in the opening defined by the support such that each inwardly-protruding ridge protrudes into a corresponding circumferential void.

In an application, the prosthetic valve is intracorporeally couplable to the prosthetic valve support at a plurality of depths within the prosthetic valve support.

In an application, the prosthetic valve is intracorporeally couplable to the prosthetic valve support at a continuum of depths within the prosthetic valve support.

There is further provided, in accordance with an application of the present invention, a method for use with a prosthetic valve for implantation at a native valve of a heart of a subject, the method including:

delivering an upstream support portion of a prosthetic valve support, in a compressed configuration thereof, to an upstream side of the native valve, the upstream support portion in the compressed configuration thereof, having a generally cylindrical shape, the cylindrical shape having a downstream end and an upstream end, each end having a perimeter, each perimeter of the cylindrical shape having a length;

coupling the prosthetic valve support to the native valve; and expanding the upstream support portion toward an uncompressed configuration thereof, such that:

the perimeter of the downstream end of the upstream support portion in the compressed configuration thereof becomes an inner perimeter of the upstream support portion in the uncompressed configuration thereof, the perimeter of the upstream end of the upstream support portion in the compressed configuration thereof becomes an outer perimeter of the upstream support portion in the uncompressed configuration thereof, and the inner perimeter of the upstream support portion defines an opening.

In an application, coupling the prosthetic valve support to the native valve includes coupling the downstream end of the upstream support portion in the compressed configuration thereof to the native valve.

In an application, expanding the upstream support portion includes expanding the upstream support portion subsequently to coupling the prosthetic valve support to the native valve.

In an application, expanding the upstream support portion toward the uncompressed configuration thereof, includes increasing the length of the perimeter of the upstream end of the upstream support portion more than the length of the perimeter of the downstream end of the upstream support portion.

In an application, the native valve includes a native annulus, and coupling the prosthetic valve support to the native valve, and expanding the upstream support portion includes coupling the prosthetic valve support to the native valve, and expanding the upstream support portion such that no part of the prosthetic valve support that circumscribes a space that has a perimeter greater than 60 mm is disposed downstream of the native annulus.

In an application, the native valve includes a plurality of native leaflets, and coupling the prosthetic valve support to the native valve, and expanding the upstream support portion includes coupling the prosthetic valve support to the native valve, and expanding the upstream support portion such that no part of the prosthetic valve support that circumscribes a space that has a perimeter greater than 60 mm is disposed downstream of the native leaflets.

In an application, the native valve includes a native annulus, and coupling the prosthetic valve support to the native valve, and expanding the upstream support portion includes coupling the prosthetic valve support to the native valve, and expanding the upstream support portion such that no part of the prosthetic valve support that circumscribes a space that has a perimeter greater than 60 mm traverses the native annulus.

In an application, delivering the upstream support portion to the upstream side of the native valve includes delivering the upstream support portion to an upstream side of a mitral valve of the subject, and coupling the prosthetic valve support to the native valve includes coupling the prosthetic valve support to the mitral valve.

In an application, delivering the upstream support portion to the upstream side of the native valve includes delivering the upstream support portion to an upstream side of a tricuspid valve of the subject, and coupling the prosthetic valve support to the native valve includes coupling the prosthetic valve support to the tricuspid valve.

In an application, delivering the upstream support portion to the upstream side of the native valve includes delivering the upstream support portion to an upstream side of a pulmonary valve of the subject, and coupling the prosthetic valve support to the native valve includes coupling the prosthetic valve support to the pulmonary valve.

In an application, delivering the upstream support portion to the upstream side of the native valve includes delivering the upstream support portion to an upstream side of an aortic valve of the subject, and coupling the prosthetic valve support to the native valve includes coupling the prosthetic valve support to the aortic valve.

In an application, delivering the upstream support portion, coupling the prosthetic valve support, and expanding the upstream support portion includes delivering the upstream support portion, coupling the prosthetic valve support, and expanding the upstream support portion without using cardiopulmonary bypass.

In an application, the method further includes subsequently coupling the prosthetic valve to the prosthetic valve support by expanding the prosthetic valve within the opening defined by the upstream support portion.

In an application, expanding the prosthetic valve includes expanding the prosthetic valve within the opening defined by the upstream support portion such that:
a perimeter of the prosthetic valve is restricted by the inner perimeter of the upstream support portion, and
the expanding of the prosthetic valve does not include causing the prosthetic valve support to apply a radially-expansive force to the native valve.

In an application, coupling the prosthetic valve support to the native valve includes coupling the prosthetic valve support to the native valve in a manner that allows the native valve to continue to function, at least in part.

In an application, coupling the prosthetic valve support to the native valve in a manner that allows the native valve to continue to function, at least in part, includes coupling the prosthetic valve support to the native valve in a manner that allows the heart of the subject to support the subject for longer than 1 minute after the prosthetic valve support is coupled to the native valve of the subject.

In an application, coupling the prosthetic valve support to the native valve in a manner that allows the native valve to continue to function, at least in part, includes coupling the prosthetic valve support to the native valve in a manner that allows the heart of the subject to support the subject for longer than 2 minutes after the prosthetic valve support is coupled to the native valve of the subject.

In an application, coupling the prosthetic valve support to the native valve in a manner that allows the native valve to continue to function, at least in part, includes coupling the prosthetic valve support to the native valve in a manner that allows the heart of the subject to support the subject for longer than 5 minutes after the prosthetic valve support is coupled to the native valve of the subject.

In an application, coupling the prosthetic valve support to the native valve in a manner that allows the native valve to continue to function, at least in part, includes coupling the prosthetic valve support to the native valve in a manner that allows the heart of the subject to support the subject for longer than 1 hour after the prosthetic valve support is coupled to the native valve of the subject.

In an application, expanding the upstream support portion toward the uncompressed configuration thereof, includes expanding the upstream support portion such that the length of the outer perimeter is at least 10% greater than the length of the inner perimeter.

In an application, expanding the upstream support portion toward the uncompressed configuration thereof, includes expanding the upstream support portion such that the length of the outer perimeter is at least 50% greater than the length of the inner perimeter.

In an application, expanding the upstream support portion toward the uncompressed configuration thereof, includes expanding the upstream support portion such that the length of the outer perimeter is at least 80% greater than the length of the inner perimeter.

In an application, expanding the upstream support portion toward the uncompressed configuration thereof, includes expanding the upstream support portion such that the length of the inner perimeter is between 62 and 105 mm.

In an application, expanding the upstream support portion toward the uncompressed configuration thereof, includes expanding the upstream support portion such that the length of the inner perimeter is between 65 and 80 mm.

In an application, expanding the upstream support portion toward the uncompressed configuration thereof, includes expanding the upstream support portion such that the length of the inner perimeter is between 75 and 80 mm.

In an application, expanding the upstream support portion toward the uncompressed configuration thereof, includes expanding the upstream support portion such that the length of the outer perimeter is between 125 and 190 mm.

In an application, expanding the upstream support portion toward the uncompressed configuration thereof, includes expanding the upstream support portion such that the length of the outer perimeter is between 140 and 170 mm.

In an application, expanding the upstream support portion toward the uncompressed configuration thereof, includes expanding the upstream support portion such that the length of the outer perimeter is between 140 and 150 mm.

In an application, expanding the upstream support portion toward the uncompressed configuration thereof, includes expanding the upstream support portion such that the opening defined by the inner perimeter of the upstream support portion has a greatest diameter of between 20 and 35 mm.

In an application, expanding the upstream support portion toward the uncompressed configuration thereof, includes expanding the upstream support portion such that the greatest diameter of the opening defined by the inner perimeter of the upstream support portion is between 23 and 32 mm.

In an application, expanding the upstream support portion toward the uncompressed configuration thereof, includes expanding the upstream support portion such that the greatest diameter of the opening defined by the inner perimeter of the upstream support portion is between 25 and 30 mm.

In an application, the prosthetic valve support includes one or more clips, and coupling the prosthetic valve support to the native valve includes coupling the clips to the native valve.

In an application:

each clip includes two clip arms, and is movable between an open and a closed configuration thereof, irrespective of a state of deployment of the upstream support portion, and coupling the clips to the native valve includes coupling the clips to the native valve without automatically changing the state of deployment of the upstream support portion.

There is further provided, in accordance with an application of the present invention, apparatus for use with a native heart valve of a subject, the apparatus including:

a prosthetic valve support, including:

an upstream support portion shaped to define an opening and configured to be placed against an upstream side of the native valve of the subject; and at least one clip:

including a plurality of clip arms, at least a first clip arm being movable with respect to a second clip arm, having an open configuration and a closed configuration, being movable between the open and closed configurations irrespective of a state of deployment of the upstream support portion, and configured to be coupled to a leaflet of the native valve; and a prosthetic valve:

disposable in the opening defined by the support, and intracorporeally couplable to the support by expanding the prosthetic valve in the opening defined by the support.

In an application, the at least one clip includes two clips.

In an application, the opening defined by the upstream support portion has a depth, from an upstream side of the upstream support portion to a downstream side of the upstream support portion, of less than 5 mm.

In an application, the opening defined by the upstream support portion has a depth, from an upstream side of the upstream support portion to a downstream side of the upstream support portion, of less than 2 mm.

In an application, the opening defined by the upstream support portion has a depth, from an upstream side of the upstream support portion to a downstream side of the upstream support portion, of between 0.3 mm and 2 mm.

In an application, the opening defined by the upstream support portion has a depth, from an upstream side of the upstream support portion to a downstream side of the upstream support portion, and a diameter that is more than 4 times greater than the depth.

In an application, the opening defined by the upstream support portion has a depth, from an upstream side of the upstream support portion to a downstream side of the upstream support portion, and a diameter that is more than 6 times greater than the depth.

In an application, the opening defined by the upstream support portion has a depth, from an upstream side of the upstream support portion to a downstream side of the upstream support portion, and a diameter that is more than 10 times greater than the depth.

In an application, the upstream support portion is generally annular.

In an application, the upstream support portion is configured to be placed against an upstream side of a mitral valve of the subject.

In an application, the upstream support portion is configured to be placed against an upstream side of a tricuspid valve of the subject.

In an application, the upstream support portion is configured to be placed against an upstream side of a pulmonary valve of the subject.

In an application, the upstream support portion is configured to be placed against an upstream side of an aortic valve of the subject.

In an application, the prosthetic valve includes one or more prosthetic valve leaflets, configured to regulate flow of blood through the prosthetic valve.

In an application, the prosthetic valve includes a ball, configured to regulate flow of blood through the prosthetic valve.

In an application, the apparatus further includes a stabilizing element, coupled to the at least one clip and shaped to define an aperture.

In an application, the at least one clip includes two clips, and the stabilizing element is coupled to both clips.

In an application, the stabilizing element is configured to facilitate coupling of the prosthetic valve to the prosthetic valve support.

In an application, the upstream support portion and the prosthetic valve include respective lattice structures, each lattice structure defining a plurality of struts, and a plurality of voids between the struts.

In an application, the lattice structure of the prosthetic valve support defines a number of inwardly-protruding ridges, and the lattice structure of the prosthetic valve defines a number of circumferential voids.

In an application, the prosthetic valve support defines a number of ridges that is equal to the number of circumferential voids defined by the prosthetic valve at at least one transverse plane of the prosthetic valve.

In an application, the prosthetic valve is intracorporeally couplable to the support by expanding the prosthetic valve in the opening defined by the support such that each inwardly-protruding ridge protrudes into a corresponding circumferential void.

In an application, the clips are articulatably coupled to the upstream support portion.

In an application, the clips are coupled to the upstream support portion via a flexible connector.

In an application, the clips are coupled to the upstream support portion via a hinge.

In an application, the upstream support portion has an outer perimeter and an inner perimeter, the inner perimeter defining the opening, each perimeter having a respective length, and the length of the outer perimeter is at least 10% greater than the length of the inner perimeter.

In an application, the inner perimeter is defined by a free inner edge of the upstream support portion.

In an application, the inner perimeter is defined by a curved or folded edge of the upstream support portion.

In an application, the curved or folded edge of the upstream support portion has a radius of curvature that is less than 2.5 mm.

In an application, the curved or folded edge of the upstream support portion has a radius of curvature that is less than 1 mm.

In an application:

the upstream support portion has an upstream side and a downstream side, and a total height from the upstream side to the downstream side, the prosthetic valve has an upstream end and a downstream end, and a height from the upstream end to the downstream end, and the height of the prosthetic valve is at least 1.5 times greater than the total height of the upstream support portion.

In an application, the height of the prosthetic valve is at least 3 times greater than the total height of the upstream support portion.

In an application, the height of the prosthetic valve is at least 5 times greater than the total height of the upstream support portion.

In an application:

the upstream support portion has an upstream side and a downstream side, and the opening defined by the upstream support portion has a depth from the upstream side to the downstream side, the prosthetic valve has an upstream end and a downstream end, and a height from the upstream end to the downstream end, and the height of the prosthetic valve is at least 1.5 times greater than the depth of the opening defined by the upstream support portion.

In an application, the height of the prosthetic valve is at least 3 times greater than the depth of the opening defined by the upstream support portion.

In an application, the height of the prosthetic valve is at least 5 times greater than the depth of the opening defined by the upstream support portion.

In an application, the prosthetic valve is intracorporeally couplable to the prosthetic valve support at a plurality of depths within the prosthetic valve support.

In an application, the prosthetic valve is intracorporeally couplable to the prosthetic valve support at a continuum of depths within the prosthetic valve support.

There is further provided, in accordance with an application of the present invention, apparatus for use with a native valve of a heart of a subject, the native valve defining an orifice, and having native leaflets and a native blood flow regulation functionality, the apparatus including:

a prosthetic valve support, couplable to the native valve, and including an upstream support portion:

having an inner perimeter that defines an opening, being configured to be placed against an upstream side of the native valve, such that blood flowing through the orifice of the native valve flows through the opening of the upstream support portion, being configured to be coupled to the native valve without eliminating the native regulation functionality; and a prosthetic valve:

being advanceable into the opening defined by the support, including at least one check valve element, configured to provide a substitute blood flow regulation functionality, and being couplable to the upstream support portion by expanding against the inner perimeter of the upstream support portion, the apparatus being configured such that, when (1) the upstream support portion is coupled to the native valve, and (2) the prosthetic valve expands against the inner perimeter of the upstream support portion, the prosthetic valve replaces, at least in part, the native regulation functionality with the substitute regulation functionality.

In an application:

the prosthetic valve is advanceable into the opening defined by the support in a compressed configuration of the prosthetic valve, and is couplable to the upstream support portion by expanding toward an uncompressed configuration of the prosthetic valve, in the uncompressed configuration, the prosthetic valve is shaped to define a lumen, the at least one check valve element includes at least one prosthetic valve leaflet, disposed in the lumen of the prosthetic valve, and the apparatus is configured such that, when (1) the upstream support portion is coupled to the native valve, and (2) the prosthetic valve expands against the inner perimeter of the upstream support portion, the prosthetic valve replaces, at least in part, the native regulation functionality with the substitute regulation functionality, by the prosthetic valve leaflets regulating blood flow through the lumen of the prosthetic valve.

In an application, the prosthetic valve support:

includes one or more clips, configured to be coupled to a part of the native valve, is couplable to the native valve by coupling the clips to a part of the native valve.

In an application, the clips are configured to be coupled to the native leaflets of the native valve, and the prosthetic valve support is couplable to the native valve by coupling the clips to the native leaflets.

In an application, the clips are configured to be coupled to the native valve without eliminating the native regulation functionality, by being configured to allow the native leaflets to continue to function, at least in part.

In an application, the clips are configured to be coupled to the native valve without eliminating the native regulation functionality, by being articulatably coupled to the upstream support portion.

In an application, the clips are coupled to the upstream support portion via a flexible connector.

In an application, the clips are coupled to the upstream support portion via a hinge.

In an application, the clips are configured, when the upstream support portion is disposed against the upstream side of the native valve and the clips are coupled to the native leaflets, to move through an arc of greater than 45 degrees during a cardiac cycle of the heart of the subject.

In an application, the clips are configured, when the upstream support portion is disposed against the upstream side of the native valve and the clips are coupled to the native leaflets, to move through an arc of greater than 60 degrees during a cardiac cycle of the heart of the subject.

In an application, the clips are configured, when the upstream support portion is disposed against the upstream side of the native valve and the clips are coupled to the native leaflets, to move through an arc of greater than 80 degrees during a cardiac cycle of the heart of the subject.

In an application, the clips are configured, when the upstream support portion is disposed against the upstream side of the native valve and the clips are coupled to the native leaflets, to move toward each other during ventricular systole of the subject, and to move away from each other during ventricular diastole of the subject.

There is further provided, in accordance with an application of the present invention, apparatus for use with a prosthetic valve for implantation at a native heart valve of a subject, the apparatus including an upstream support portion, the upstream support portion:

having an outer perimeter, having a length between 125 and 190 mm, having an inner perimeter that defines an opening, the inner perimeter having length between 62 and 105 mm and a depth of less than 5 mm, and being configured to be placed against an upstream side of the native valve, any portion of the apparatus that circumscribes a space that has a perimeter greater than 60 mm having a depth of less than 5 mm, and the apparatus being configured to be intracorporeally coupled to the prosthetic valve by the prosthetic valve being expanded in the opening defined by the upstream support portion.

In an application, the upstream support portion is generally annular.

In an application, the opening defined by the inner perimeter of the upstream support portion has a shape selected from the group consisting of: generally circular, elliptical, and oval.

In an application, the depth of the opening defined by the inner perimeter of the upstream support portion is less than 2 mm.

In an application, the depth of the opening defined by the inner perimeter of the upstream support portion is between 0.3 mm and 2 mm.

In an application, the length of the outer perimeter is between 140 and 170 mm.

In an application, the length of the outer perimeter is between 140 and 150 mm.

In an application, the length of the inner perimeter is between 65 and 80 mm.

In an application, the length of the inner perimeter is between 75 and 80 mm.

In an application, the opening defined by the inner perimeter of the upstream support portion has a greatest diameter of between 20 and 35 mm.

In an application, the greatest diameter of the opening defined by the inner perimeter of the upstream support portion is between 23 and 32 mm.

In an application, the greatest diameter of the opening defined by the inner perimeter of the upstream support portion is between 25 and 30 mm.

In an application, the length of the outer perimeter is at least 10% greater than the length of the inner perimeter.

In an application, the length of the outer perimeter is at least 50% greater than the length of the inner perimeter.

In an application, the length of the outer perimeter is at least 80% greater than the length of the inner perimeter.

In an application, the opening defined by the inner perimeter of the upstream support portion has a diameter that is more than 4 times greater than the depth of the opening.

In an application, the opening defined by the inner perimeter of the upstream support portion has a diameter that is more than 6 times greater than the depth of the opening.

In an application, the opening defined by the inner perimeter of the upstream support portion has a diameter that is more than 10 times greater than the depth of the opening.

In an application, the apparatus further includes at least one clip, the clip including a plurality of clip arms and configured to couple the upstream support portion to the native valve.

In an application, the clip is articulatably coupled to the upstream support portion.

There is further provided, in accordance with an application of the present invention, apparatus for use with a prosthetic valve for implantation at a native valve of a subject, the apparatus including a prosthetic valve support, including:

an upstream support portion configured to be placed against an upstream side of the native valve, and at least one clip:

including a plurality of clip arms, at least a first clip arm being movable with respect to a second clip arm, having an open configuration and a closed configuration, being movable between the open and closed configurations independently of a state of deployment of the prosthetic valve support, and configured to be coupled to a leaflet of the native valve, any portion of the apparatus that circumscribes a space that has a perimeter greater than 60 mm having a depth of less than 5 mm, and the apparatus being configured to be intracorporeally coupled to the prosthetic valve by the prosthetic valve being expanded in the opening defined by the upstream support portion.

In an application, any portion of the apparatus that circumscribes a space that has a perimeter greater than 60 mm has a depth of less than 2 mm.

In an application, any portion of the apparatus that circumscribes a space that has a perimeter greater than 60 mm has a depth of between 0.3 mm and 2 mm.

In an application, the upstream support portion has an inner perimeter, shaped to define an opening that has a depth of less than 5 mm.

In an application, the opening defined by the inner perimeter of the upstream support portion has a depth of less than 2 mm.

In an application, the opening defined by the inner perimeter of the upstream support portion has a depth of between 0.3 mm and 2 mm.

In an application, the apparatus further includes a stabilizing element, coupled to the at least one clip, and shaped to define an aperture that has a depth of less than 5 mm.

In an application, the aperture defined by the stabilizing element has a depth of less than 2 mm.

There is further provided, in accordance with an application of the present invention, apparatus for implantation of a medical device, the apparatus including:

a tubular member, shaped to define a lumen; and a plug, slidable within the tubular member, and including a restricting portion and a second portion, the apparatus:

having a open configuration, in which the restricting portion is disposed outside of the lumen of the tubular member, and in which the medical device is couplable to, and decouplable from, the apparatus, and having a locking configuration, in which at least part of the restricting portion is disposed within the lumen of the tubular member, and in which the medical device is generally not couplable to, or decouplable from, the apparatus, and being movable between the open and locking configurations by sliding the plug within the tubular member.

In an application, the medical device includes a wire, and the apparatus is configured to be coupled to the medical device when the wire is coupled to the plug, and to be decouplable from the medical device by moving the apparatus into the open configuration such that the wire is decouplable from the plug.

In an application, the apparatus includes a controller, having at least three controller configurations between which the controller is movable, the at least three controller configurations including at least:

a first controller configuration, including a first locking configuration, a second controller configuration, including a second locking configuration, and a third controller configuration, including an open configuration, wherein the apparatus is configured such that, when the apparatus is coupled to the wire, moving the controller from the first controller configuration to the second controller configuration applies tension to the wire, and moving the controller from the second configuration to the first configuration at least partly releases the tension.

In an application, the medical device includes a clip, and the wire includes a clip-controller interface, and the apparatus is configured such that, when the apparatus is coupled to the clip-controller interface, moving the controller between the first and second configurations controls a state of openness of the clip.

There is further provided, in accordance with an application of the present invention, apparatus for use with a prosthetic valve for implantation at a native valve of a subject, the native valve (1) defining an orifice, (2) including at least one native leaflet, having a native beating, and (3) having a native blood flow regulation functionality, the apparatus including:

a prosthetic valve support, including:
  an upstream support portion, configured to be placed against an upstream side of the native valve, to have an inner perimeter that defines an opening, the opening configured to receive the prosthetic valve, and
  at least one clip, configured to be coupled to a native leaflet of the native valve, the clip including a plurality of clip arms, at least one clip arm coupled to a clip-controller interface; and
a clip controller, couplable to the clip-controller interface, and configured to control a relative angular disposition between the clip arms.

In an application, the clip controller is configured to control a relative angular disposition of the clip aims independently of a state of expansion of the prosthetic valve support.

In an application, the at least one clip includes two or more clips.

In an application, the two or more clips are independently controllable.

In an application, the apparatus includes two or more clip controllers, each clip controller being couplable to at least one of the two or more clips.

In an application, the clip includes a first clip arm being configured to be disposed against an upstream side of the leaflet, and a second clip arm being configured to be disposed against a downstream side of the leaflet.

In an application, the second clip arm is coupled to the clip-controller interface.

In an application, the clip is configured to be coupled to the native valve without eliminating the native regulation functionality.

In an application, the clip is configured to be coupled to the native valve without eliminating the native regulation functionality, by being configured, when the clip is coupled to the native leaflet, to allow the native leaflet to continue to function, at least in part.

In an application, the clip is configured to be coupled to the native valve without eliminating the native regulation functionality, by being articulatably coupled to the upstream support portion.

In an application, the clip is coupled to the upstream support portion via a flexible connector.

In an application, the clip is coupled to the upstream support portion via a hinge.

In an application, the clip is configured, when the upstream support portion is disposed against the upstream side of the native valve and the clip is coupled to the native leaflet, to move through an arc of greater than 45 degrees during a cardiac cycle of the heart of the subject.

In an application, the clip is configured, when the upstream support portion is disposed against the upstream side of the native valve and the clip is coupled to the native leaflet, to move through an arc of greater than 60 degrees during a cardiac cycle of the heart of the subject.

In an application, the clip is configured, when the upstream support portion is disposed against the upstream side of the native valve and the clip is coupled to the native leaflet, to move through an arc of greater than 80 degrees during a cardiac cycle of the heart of the subject.

In an application, the at least one clip includes two or more clips, each clip configured to be coupled to a respective native leaflet, and the clips are configured, when the upstream support portion is disposed against the upstream side of the native valve and the clips are coupled to the native leaflets, to move toward each other during ventricular systole of the subject, and to move away from each other during ventricular diastole of the subject.

In an application, the at least one clip includes two or more clips, each clip configured to be coupled to a respective native leaflet, and the clips are configured, when the upstream support portion is disposed against the upstream side of the native valve and the clips are coupled to the native leaflets, to move toward each other during ventricular diastole of the subject, and to move away from each other during ventricular systole of the subject.

There is further provided, in accordance with an application of the present invention, a method for implanting a prosthetic heart valve at a native heart valve of a subject, the method including:

coupling a prosthetic valve support to the native valve;
subsequently expanding an upstream support portion of the prosthetic valve support, such that:
  an outer perimeter defined by the upstream support portion has a greatest diameter that is larger than a greatest diameter of an orifice of the native valve, and
  an opening defined by an inner perimeter of the upstream support portion has a greatest diameter that is smaller than the greatest diameter of the orifice of the native valve; and
subsequently coupling the prosthetic valve to the prosthetic valve support by expanding the prosthetic valve within the opening defined by the inner perimeter of the upstream support portion.

In an application, coupling the prosthetic valve support to the native valve and subsequently coupling the prosthetic valve to the prosthetic valve support, includes coupling the prosthetic valve support to the native valve and subsequently coupling the prosthetic valve to the prosthetic valve support without using a cardiopulmonary bypass.

In an application, expanding the upstream support includes expanding the upstream support portion such that the opening defined by the inner perimeter of the upstream support portion has a greatest diameter that is less than 90% of the greatest diameter of the orifice of the native valve.

In an application, expanding the upstream support portion includes expanding the upstream support portion such that the opening defined by the inner perimeter of the upstream support portion has a greatest diameter that is less than 80% of the greatest diameter of the orifice of the native valve.

In an application, expanding the upstream support portion includes expanding the upstream support portion such that the opening defined by the inner perimeter of the upstream support portion has a greatest diameter that is less than 60% of a greatest diameter of the orifice of the native valve.

In an application, expanding the upstream support portion includes expanding the upstream support portion such that the opening defined by the inner perimeter of the upstream support portion has a greatest diameter that is less than 50% of a greatest diameter of the orifice of the native valve.

In an application, coupling the prosthetic valve support to the native valve includes coupling one or more clips of the prosthetic valve support to one or more parts of the native valve.

In an application, coupling the one or more clips to the one or more parts of the native valve includes coupling the one or more clips to one or more native leaflets of the native valve.

In an application, coupling the one or more clips to the one or more native leaflets includes coupling the one or more clips to the one or more native leaflets such that the native leaflets continue to function, at least in part.

In an application:
the upstream support portion has (1) a compressed configuration in which the upstream support portion has a generally cylindrical shape, the cylindrical shape having a downstream end and an upstream end, each end having a perimeter, each perimeter of the cylindrical shape having a length, and (2) an uncompressed configuration in which the upstream support portion has the outer perimeter, and the inner perimeter that defines the opening, and
coupling the prosthetic valve support to the native valve includes coupling the downstream end of the cylindrical shape of the upstream support portion to the native valve.

In an application, expanding the prosthetic valve support includes expanding the prosthetic valve support such that:
the perimeter of the downstream end of the upstream support portion in the compressed configuration thereof becomes the inner perimeter of the upstream support portion in the uncompressed configuration thereof, and
the perimeter of the upstream end of the upstream support portion in the compressed configuration thereof becomes the outer perimeter of the upstream support portion in the uncompressed configuration thereof.

In an application, subsequently coupling the prosthetic valve to the prosthetic valve support includes coupling the prosthetic valve to the prosthetic valve support more than 1 minute after the prosthetic valve support is coupled to the native valve of the subject.

In an application, subsequently coupling the prosthetic valve to the prosthetic valve support includes coupling the prosthetic valve to the prosthetic valve support more than 2 minutes after the prosthetic valve support is coupled to the native valve of the subject.

In an application, subsequently coupling the prosthetic valve to the prosthetic valve support includes coupling the prosthetic valve to the prosthetic valve support more than 5 minutes after the prosthetic valve support is coupled to the native valve of the subject.

In an application, subsequently coupling the prosthetic valve to the prosthetic valve support includes coupling the prosthetic valve to the prosthetic valve support more than 1 hour after the prosthetic valve support is coupled to the native valve of the subject.

There is further provided, in accordance with an application of the present invention, a method for implanting a prosthetic heart valve at a native heart valve of a subject, the method including:
delivering an upstream support portion of a prosthetic valve support, to a heart of the subject;
placing the upstream support portion against an upstream side of the native valve, such that the upstream support portion has an inner perimeter that defines an opening; and
subsequently expanding at least part of the prosthetic valve within the opening defined by the upstream support portion, such that a perimeter of the prosthetic valve is restricted by the inner perimeter of the upstream support portion, and such that the expanding of the prosthetic valve does not include causing the prosthetic valve support to apply a radially-expansive force to the native valve.

In an application, the native valve includes a plurality of native leaflets, and the method further includes coupling the prosthetic valve support to at least one leaflet of the native valve.

In an application, the native valve includes a native annulus, and placing the upstream support portion against the upstream side of the prosthetic valve includes placing the upstream support portion such that no part of the prosthetic valve support that circumscribes a space that has a perimeter greater than 60 mm is disposed downstream of the native annulus.

In an application, the native valve includes a plurality of native leaflets, and placing the upstream support portion against the upstream side of the prosthetic valve includes placing the upstream support portion such that no part of the prosthetic valve support that circumscribes a space that has a perimeter greater than 60 mm is disposed downstream of the native leaflets.

In an application, the native valve includes a native annulus, and placing the upstream support portion against the upstream side of the prosthetic valve includes placing the upstream support portion such that no part of the prosthetic valve support that circumscribes a space that has a perimeter greater than 60 mm traverses the native annulus.

In an application, expanding the at least part of the prosthetic valve includes expanding the at least part of the prosthetic valve such that the perimeter of the prosthetic valve is restricted by the inner perimeter of the upstream support portion, to a length that is generally equal to a length of the inner perimeter of the prosthetic valve support.

In an application, coupling the prosthetic valve support to the at least one leaflet, includes coupling the prosthetic valve support to the at least one leaflet using at least one clip, the at least one clip including at least two clip arms.

In an application:
the perimeter of the prosthetic valve that is restricted by the inner perimeter of the upstream support portion has a length, and
expanding the at least part of the prosthetic valve within the opening defined by the upstream support portion, includes expanding the at least part of the prosthetic valve such that the length of the perimeter of the prosthetic valve is restricted by the inner perimeter of the upstream support portion to between 62 and 105 mm.

In an application, expanding the at least part of the prosthetic valve within the opening defined by the upstream support portion, includes expanding the at least part of the prosthetic valve such that the length of the perimeter of the prosthetic valve is restricted by the inner perimeter of the upstream support portion to between 65 and 80 mm.

In an application, expanding the at least part of the prosthetic valve within the opening defined by the upstream support portion, includes expanding the at least part of the prosthetic valve such that the length of the perimeter of the prosthetic valve is restricted by the inner perimeter of the upstream support portion to between 75 and 80 mm.

In an application:
the at least part of the prosthetic valve that is restricted by the inner perimeter of the upstream support portion has a greatest diameter, and
expanding the at least part of the prosthetic valve within the opening defined by the upstream support portion, includes expanding the at least part of the prosthetic valve such that the greatest diameter of the at least part of the prosthetic valve is restricted by the inner perimeter of the upstream support portion, to between 20 and 35 mm.

In an application, expanding the at least part of the prosthetic valve within the opening defined by the upstream support portion, includes expanding the at least part of the prosthetic valve such that the greatest diameter of the at least part of the prosthetic valve is restricted by the inner perimeter of the upstream support portion, to between 23 and 32 mm.

In an application, expanding the at least part of the prosthetic valve within the opening defined by the upstream support portion, includes expanding the at least part of the prosthetic valve such that the greatest diameter of the at least part of the prosthetic valve is restricted by the inner perimeter of the upstream support portion, to between 25 and 30 mm.

In an application:
the native valve defines an orifice, the orifice having a greatest diameter,
the at least part of the prosthetic valve that is restricted by the inner perimeter of the upstream support portion has a greatest diameter, and
expanding the at least part of the prosthetic valve within the opening defined by the upstream support portion, includes expanding the at least part of the prosthetic valve such that the greatest diameter of the at least part of the prosthetic valve is restricted by the inner perimeter of the upstream support portion, to less than 90% of the greatest diameter of the orifice of the native valve.

In an application, expanding the at least part of the prosthetic valve within the opening defined by the upstream support portion, includes expanding the at least part of the prosthetic valve such that the greatest diameter of the at least part of the prosthetic valve is restricted by the inner perimeter of the upstream support portion, to less than 80% of the greatest diameter of the native valve.

In an application, expanding the at least part of the prosthetic valve within the opening defined by the upstream support portion, includes expanding the at least part of the prosthetic valve such that the greatest diameter of the at least part of the prosthetic valve is restricted by the inner perimeter of the upstream support portion, to less than 60% of the greatest diameter of the native valve.

In an application, expanding the at least part of the prosthetic valve within the opening defined by the upstream support portion, includes expanding the at least part of the prosthetic valve such that the greatest diameter of the at least part of the prosthetic valve is restricted by the inner perimeter of the upstream support portion, to less than 50% of the greatest diameter of the native valve.

There is further provided, in accordance with an application of the present invention, a method for implanting a prosthetic valve at a native heart valve of a subject, the native heart valve including one or more native leaflets, the method including:
without using cardiopulmonary bypass:
transvascularly delivering an upstream support portion of a prosthetic valve support to an upstream side of the native valve;
coupling the prosthetic valve support to the native valve in a manner that allows the native valve to continue to function, at least in part;
while the native valve continues to function at least in part, transvascularly delivering the prosthetic valve to the native valve; and
subsequently coupling the prosthetic valve to the prosthetic valve support by expanding the prosthetic valve in an opening defined by the upstream support portion of the prosthetic valve support.

In an application:
the native valve has a native blood flow regulation functionality,
coupling the prosthetic valve support to the native valve includes coupling the prosthetic valve support to the native valve without eliminating the native regulation functionality of the native valve, and
subsequently coupling the prosthetic valve to the prosthetic valve support includes subsequently replacing, at least in part, the native blood flow regulation functionality with a substitute blood flow regulation functionality.

In an application, the prosthetic valve support includes one or more clips, coupled to the upstream support portion, and configured to be couplable to the native leaflets, and coupling the prosthetic valve support to the native valve includes coupling the one or more clips to the native leaflets.

In an application, the one or more clips are articulatably coupled to the upstream support portion, and coupling the one or more clips to the native leaflets includes coupling the one or more clips that are articulatably coupled to the upstream support portion, to the native leaflets.

In an application, the one or more clips include a plurality of clips, and coupling the one or more clips to the native leaflets, includes coupling the plurality of clips to the native leaflets such that the plurality of clips move toward each other during ventricular systole of the subject, and move away from each other during ventricular diastole of the subject.

In an application, coupling the prosthetic valve support to the native valve in a manner that allows the native valve to continue to function, at least in part, includes coupling the prosthetic valve support to the native valve in a manner that allows the heart of the subject to support the subject for longer than 1 minute after the prosthetic valve support is coupled to the native valve of the subject.

In an application, coupling the prosthetic valve support to the native valve in a manner that allows the native valve to continue to function, at least in part, includes coupling the prosthetic valve support to the native valve in a manner that allows the heart of the subject to support the subject for longer than 2 minutes after the prosthetic valve support is coupled to the native valve of the subject.

In an application, coupling the prosthetic valve support to the native valve in a manner that allows the native valve to continue to function, at least in part, includes coupling the prosthetic valve support to the native valve in a manner that allows the heart of the subject to support the subject for longer than 5 minutes after the prosthetic valve support is coupled to the native valve of the subject.

In an application, coupling the prosthetic valve support to the native valve in a manner that allows the native valve to continue to function, at least in part, includes coupling the prosthetic valve support to the native valve in a manner that allows the heart of the subject to support the subject for longer than 1 hour after the prosthetic valve support is coupled to the native valve of the subject.

For some applications, techniques described herein are practiced in combination with techniques described in one or more of the references cited in the Background section and Cross-references section of the present patent application.

BRIEF DESCRIPTION OF THE DRAWINGS

FIGS. 1A-D are schematic illustrations of an implant, comprising a prosthetic valve support and a prosthetic valve, in accordance with some applications of the invention;

FIGS. 3A-L are schematic illustrations of steps in the implantation of an implant, comprising a prosthetic valve and a prosthetic valve support, in a native valve of a subject, in accordance with some applications of the invention;

FIGS. 5A-F are schematic illustrations of steps in the implantation of an implant, comprising a prosthetic valve and a prosthetic valve support, in a native valve of a subject, in accordance with some applications of the invention;

DETAILED DESCRIPTION OF EMBODIMENTS

Reference is made to FIGS. 1A-D, which are schematic illustrations of an implant 2030, comprising a prosthetic valve support 2040, and a prosthetic valve 2042, in accordance with some applications of the invention. Implant 2030 is configured to be implanted at a native heart valve of a subject, such as the mitral valve 2024 of the subject.

Figure 1A:
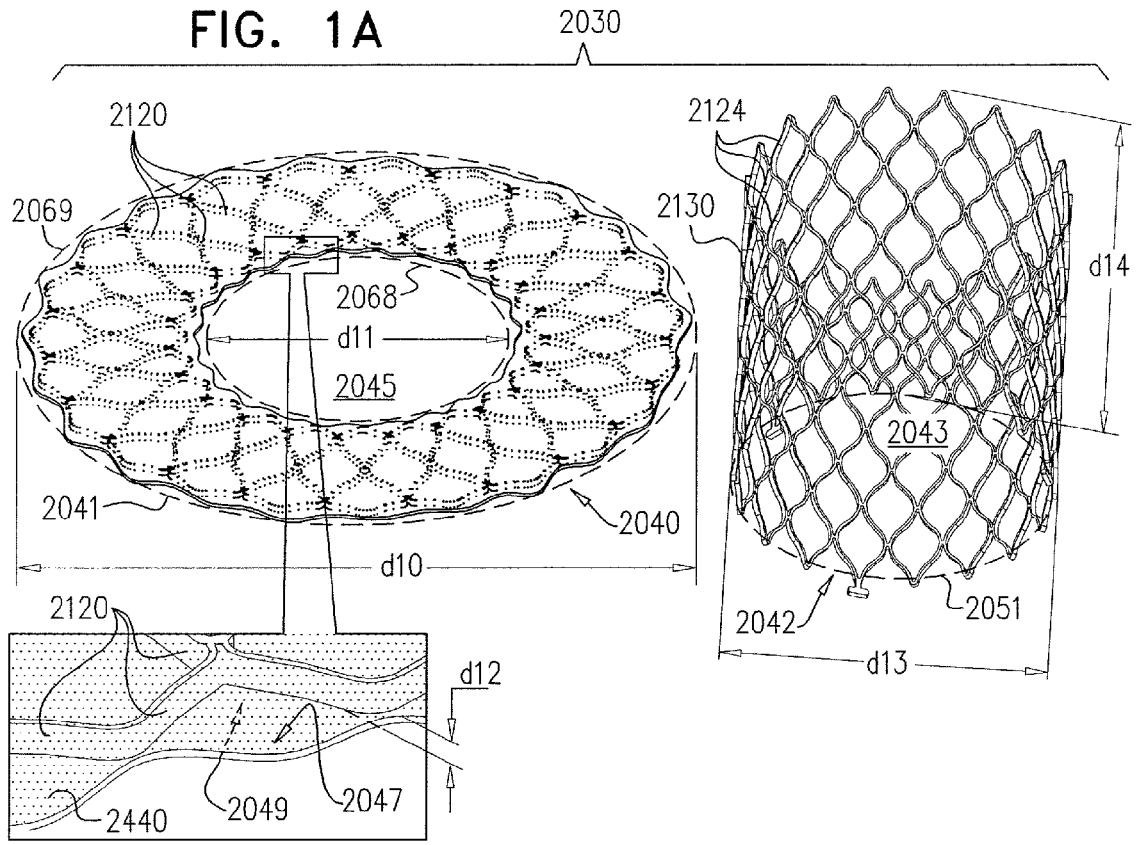

FIG. 1A shows support 2040 and prosthetic valve 2042 of implant 2030 in respective fully uncompressed configurations thereof. Support 2040 comprises an upstream support portion 2041, which is shaped to define an opening 2045, and configured to be placed against an upstream side of the native valve of the subject (e.g., against an atrial side of the mitral valve of the subject, such as against the annulus of the mitral valve of the subject). Typically, upstream support portion 2041 is configured to be placed against the upstream side of the native valve such that the entire of opening 2045 is disposed above (i.e., upstream and within a periphery defined by) the orifice of the native valve. Typically, upstream support portion 2041 is configured and/or selected such that opening 2045 has a greatest diameter that is less than 90% (e.g., less than 80%, e.g., as less than 60%, such as less than 50%) of a greatest diameter of the orifice of the native valve. Typically, upstream support portion 2041 is generally annular (e.g., portion 2041 and opening 2045 are generally elliptical, circular, and/or oval).

In the fully uncompressed configuration thereof, upstream support portion 2041 typically has an outer perimeter 2069 of length between 125 and 190 mm (e.g., between 140 and 170 mm, such as between 140 and 150 mm), and an inner perimeter 2068 (that defines opening 2045) of length between 62 and 105 mm (e.g., between 65 and 80 mm, such as between 75 and 80 mm). When upstream support portion 2041 is annular, the upstream support portion, in the fully uncompressed configuration thereof, typically has an outer diameter d10 (e.g., a greatest outer diameter) of between 40 and 80 mm (e.g., between 40 and 70 mm, such as between 40 and 60 mm), and an inner diameter d11 (e.g., a greatest inner diameter) of between 20 and 35 mm (e.g., between 23 and 32 mm, such as between 25 and 30 mm). That is, opening 2045 typically has a greatest diameter of between 20 and 35 mm (e.g., between 23 and 32 mm, such as between 25 and 30 mm). Typically, outer perimeter 2069 has a length that is at least 10% (e.g., at least 50%, such as at least 80%) greater than the length of the inner perimeter 2068.

In the fully uncompressed configuration thereof, upstream support portion 2041 is typically (but not necessarily) generally flat (e.g., laminar, and/or planar). For some applications, in the fully uncompressed configuration, portion 2041 assumes a frustoconical shape, typically arranged from the generally flat composition of the portion. Portion 2041 has a thickness of less than 5 mm, such as less than 2 mm. For example the upstream support portion may have a thickness of between 0.3 mm and 2 mm. Opening 2045 has a depth (e.g., a height) d12 from an upstream side 2047 of the upstream support portion to a downstream side 2049 of the upstream support portion. Depth d12 of opening 2045 is less than 5 mm, such as less than 2 mm. For example, depth d12 may be between 0.3 mm and 2 mm. Typically, therefore, inner diameter d11 is more than 4 times (e.g., more than 6 times, such as more than 10 times) greater than depth d12. That is, opening 2045 is more than 4 times (e.g., more than 6 times, such as more than 10 times) wider than it is deep. Typically, in the fully uncompressed configuration, upstream support portion 2041 has a total height of less than 10 mm (e.g., less than 5 mm, such as less than 2 mm).

Typically, inner perimeter 2068 comprises, or is defined by, a free inner edge of upstream support portion 2041. That is, opening 2045 resembles a hole cut out of a lamina (e.g., out of a disc). For some applications, inner perimeter 2068 comprises, or is defined by, a curved and/or folded inner edge of upstream support portion 2041. If the inner perimeter of upstream support portion 2041 comprises, or is defined by, a curved or folded edge, then a radius of curvature of the curved or folded edge is typically less than 2.5 mm, such as less than 1 mm. That is, the curve or fold of the edge is generally sharp, such that when viewed from within opening 2045, the curved or folded edge looks generally like a free edge.

It is to be noted that, for simplicity, upstream support portion 2041 is generally described herein in terms of symmetrical geometric shapes (e.g., ellipse and frustum), but that the upstream support portion may assume a symmetrical or an unsymmetrical shape.

Prosthetic valve 2042 comprises a generally tubular (e.g., cylindrical) primary structural element 2130, shaped to define a lumen 2043 therethrough, and at least one check valve element 2050 (see FIGS. 1C-D), configured to regulate blood flow through the prosthetic valve. Typically, the check valve element comprises one or more prosthetic valve leaflets 2052 (see FIGS. 1C-D), disposed in lumen 2043, and coupled (e.g., sutured) to the primary structural element. For some applications of the invention, the check valve element comprises a ball, disc, or other check valve component. For some applications of the invention, prosthetic valve 2042 comprises a commercially-available stent-based prosthetic valve.

Prosthetic valve 2042 is configured to be placed in opening 2045 of support 2040, and couplable to the support by being expandable within this opening, e.g., as described in more detail hereinbelow. Typically, support 2040 comprises tissue-engaging elements (e.g., support-anchoring elements), and is couplable to the native valve, such that coupling of prosthetic valve 2042 to the support, couples the prosthetic valve to the native valve. For some applications, prosthetic valve 2042 comprises tissue-engaging elements (e.g., valve-anchoring elements), and is alternatively or additionally directly couplable to the native valve.

In the fully uncompressed configuration thereof, prosthetic valve 2042 typically has a perimeter 2051 of length between 62 and 110 mm (e.g., between 70 and 90 mm, such as between 80 and 90 mm), and a height $d14$, (i.e., a length from an upstream end to a downstream end) of between 15 and 40 mm (e.g., between 20 and 35 mm, such as between 25 and 25 mm). When structural element 2130 is cylindrical, prosthetic valve 2042, in the fully uncompressed configuration thereof, typically has a diameter $d13$ of between 20 and 35 mm (e.g., between 25 and 35 mm, such as between 25 and 30 mm). Typically, support 2040 and prosthetic valve 2042 are configured and/or selected (e.g., paired), such that perimeter 2051 is slightly (e.g., between 1 and 15 mm, such as between 1 and 7 mm) greater than perimeter 2068, and/or that diameter $d13$ is slightly (e.g., between 1 and 5 mm, such as between 1 and 3 mm) greater than diameter $d11$.

In the respective fully uncompressed configurations thereof, height $d14$ of prosthetic valve 2042 is typically at least 1.5 times greater (e.g., at least 3 times greater, such as at least 5 times greater) than the total height of upstream support portion 2041. Typically, height $d14$ of prosthetic valve 2042 is at least 1.5 times greater (e.g., at least 3 times greater, such as at least 5 times greater) than depth $d12$ of opening 2045.

Typically, support 2040 comprises a lattice structure which defines a plurality of struts 2120, typically in a repeating arrangement, and a plurality of voids between the struts. Typically, upstream support portion 2041 comprises the lattice structure of support 2040. Typically, prosthetic valve 2042 comprises a lattice structure which defines a plurality of struts 2124, and a plurality of voids between the struts. Support 2040 and prosthetic valve 2042 typically have shape-memory (e.g., resilient, pseudoelastic and/or superelastic) properties. Typically, struts 2120 and/or struts 2124 comprise a shape-memory (e.g., resilient, pseudoelastic and/or superelastic) material, such that support 2040 and/or prosthetic valve 2042 are compressible when a compressive force is applied (e.g., prior to implantation), and re-expandable when the compressive force is removed (e.g., during implantation), as described hereinbelow. Non-limiting examples of materials that the support (e.g., struts 2120) and/or prosthetic valve (e.g., struts 2124) may comprise include nickel-titanium (Nitinol), stainless steel, nickel cobalt, cobalt chrome, titanium, tantalum, and palladium.

Typically, support 2040 and/or prosthetic valve 2042 are at least in part covered with a covering 2440 (for clarity, covering 2440 is only shown on support 2040). Non-limiting examples of materials that covering 2440 may comprise include polyethylene terephthalate (e.g., polyester), polytetrafluoroethylene (e.g., Teflon, Gore-Tex, ePTFE), and pericardial tissue. For some applications, covering 2440 comprises a fabric. Typically, a thickness of the covering is less than 0.5 mm, such as less than 0.2 mm, e.g., less than 0.1 mm, or less than 0.05 mm. In FIG. 1A, struts 2120 are shown in phantom, as they are covered by covering 2440.

For some applications of the invention, covering 2440 is configured to facilitate blood flow through the prosthetic valve, e.g., to channel blood through lumen 2043 defined by prosthetic valve 2042, and/or to prevent leakage (1) between the prosthetic valve and support 2040, and/or (2) between implant 2030 and the native valve.

Figure 2:
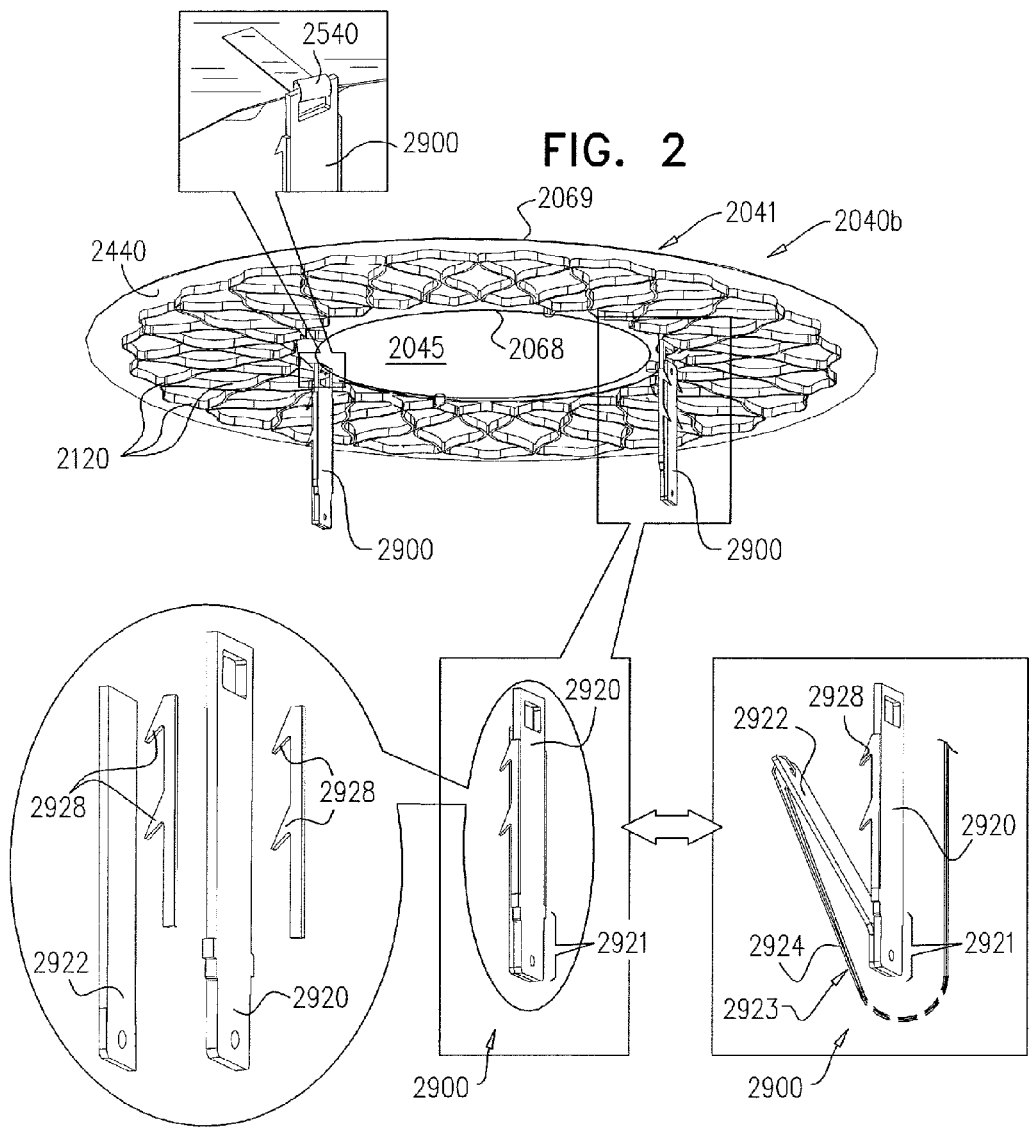
FIG. 2 is a schematic illustration of a prosthetic valve support, for use with a prosthetic valve, in accordance with some applications of the invention.

Typically, and as shown in FIGS. 1A and 2, the covering of the upstream support portion of the prosthetic valve support overlaps (e.g., is larger than) the lattice structure of the upstream support portion. For some applications, the covering of the upstream support portion defines an inner perimeter that is smaller (e.g., more than 5% smaller, e.g., more than 10% smaller, such as more than 20% smaller) than that defined by the lattice structure of the upstream support portion. For some applications, the covering of the upstream support portion defines an outer perimeter that is larger (e.g., more than 5% larger, e.g., more than 10% larger, such as more than 20% larger) than that defined by the lattice structure of the upstream support portion.

For some applications of the invention, the covering is configured to mask sharp and/or hard surfaces (e.g., metal surfaces, such as surfaces of struts 2120 and/or 2124), and thereby to protect native tissues from being damaged by such surfaces. For some applications of the invention, the covering is configured to facilitate (e.g., to enhance) coupling between support 2040 and prosthetic valve 2042 (e.g., as described hereinbelow), such as by increasing friction. For some applications of the invention, the covering is configured to facilitate (e.g., to encourage) growth of tissue (e.g., fibrosis) over one or more components of implant 2030.

Figure 1B:
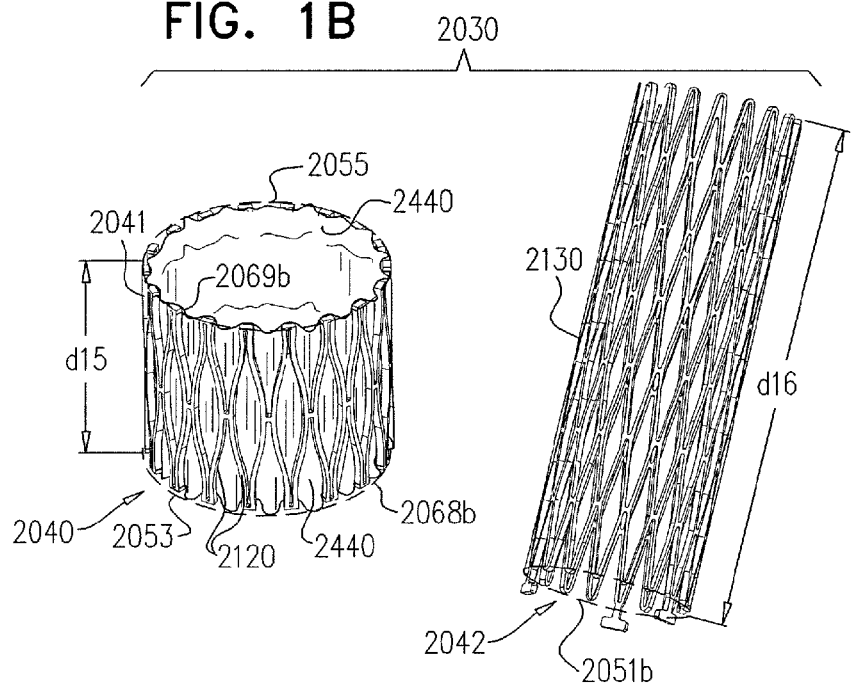

FIG. 1B shows support 2040 and prosthetic valve 2042 of implant 2030 in respective compressed configurations thereof, typically for delivery to the native valve. Typically, support 2040 and prosthetic valve 2042 are delivered percutaneously (e.g., transcatheterally). Typically, the support and the valve component are delivered to the native valve transluminally (e.g., transfemorally). For some applications, support 2040 and prosthetic valve 2042 are delivered to the native valve transatrially. For some applications, support 2040 and prosthetic valve 2042 are delivered to the native valve transapically.

In the compressed configuration thereof, upstream support portion 2041 is typically generally cylindrical, and is typically delivered to a site that is upstream of the native valve of the subject (e.g., the left atrium, upstream of the mitral valve of the subject), such that a downstream (e.g., distal) end 2053 of the support has a perimeter 2068*b*, which is a compressed inner perimeter 2068, and an upstream end 2055 of the support comprises perimeter 2069*b*, which is a compressed outer perimeter 2069.

In the compressed configuration thereof, upstream support portion 2041 typically has (e.g., perimeters 2068*b* and 2069*b* have) a perimeter of length between 9 and 30 mm (e.g., between 15 and 25 mm, such as between 18 and 22 mm), and a height d15 of between 11 and 30 mm (e.g., between 15 and 30 mm, such as between 15 and 25 mm). When upstream support portion 2041, in the compressed configuration thereof, is cylindrical, portion 2041 typically has a diameter of between 3 and 9 mm (e.g., between 5 and 8 mm, such as between 6 and 7 mm).

In the compressed configuration thereof, prosthetic valve 2042 is typically generally cylindrical. Compression of the prosthetic valve typically comprises inwardly-radial compression, such that the component is narrower and taller in the compressed configuration than in the fully uncompressed configuration thereof. In the compressed configuration thereof, prosthetic valve 2042 typically has a perimeter 2051b (a compressed perimeter 2051) of between 9 and 30 mm (e.g., between 10 and 20 mm, such as between 15 and 20 mm), and a height d16 of between 16 and 41 mm (e.g., between 20 and 35 mm, such as between 20 and 30 mm). When prosthetic valve 2042, in the compressed configuration thereof, is cylindrical, prosthetic valve 2042 typically has a diameter of between 2 and 9 mm (e.g., between 3 and 8 mm, such as between 3 and 6 mm).

Support 2040 (e.g., portion 2041) and prosthetic valve 2042 typically have shape-memory properties, and are compressed (e.g., crimped) into their respective compressed configurations prior to (e.g., immediately prior to) the implantation procedure. Typically, the support and prosthetic valve are retained (e.g., 'constrained') in this configuration by a constraining member, such as an overtube, a delivery tube, and/or other delivery apparatus. Support 2040 and prosthetic valve 2042 are typically subsequently expanded (e.g., 'deployed') close to the site of implantation by releasing the constraining (e.g., compressive) force (e.g., by removing the constraining member). That is, the compressed configurations of prosthetic valve support 2040 (e.g., of upstream support portion 2041) and prosthetic valve 2042, described with reference to FIG. 1B, typically comprise constrained compressed configurations, and the fully uncompressed configurations, described with reference to FIG. 1A, are unconstrained uncompressed configurations.

FIG. 1C shows an end-view of implant 2030, with prosthetic valve 2042 coupled to prosthetic valve support 2040 by being disposed and expanded within opening 2045 (see FIG. 1A) defined by portion 2041. FIG. 1C shows downstream side 2049 of support 2040, therefore struts 2120 are shown in solid foam. Typically, prosthetic valve 2042 is delivered to opening 2045 in a constrained compressed configuration thereof (e.g., as described with reference to FIG. 1B), and expanded (e.g., released) in the opening, such that prosthetic valve 2042 applies a radially-expansive force against inner perimeter 2068 of portion 2041. Typically, this radially-expansive force facilitates coupling of prosthetic valve 2042 to portion 2041.

So as to provide the radially-expansive force, and as described hereinabove, prosthetic valve 2042 and support 2040 (e.g., portion 2041) are typically configured and/or selected (e.g., paired) such that perimeter 2051 of prosthetic valve 2042, in the fully uncompressed configuration thereof, is slightly greater than inner perimeter 2068 of portion 2041. When prosthetic valve 2042 is expanded within opening 2045, portion 2041 (e.g., inner perimeter 2068) thereby restricts the full expansion of prosthetic valve 2042. Therefore, in the coupled configuration shown in FIG. 1C, a perimeter 2051c of prosthetic valve 2042 is typically smaller than perimeter 2051 of the prosthetic valve in the fully uncompressed configuration thereof.

As described hereinabove (e.g., with reference to FIG. 1A), upstream support portion 2041 is configured to be placed against an upstream side of the native valve. As further discussed hereinbelow (e.g., with reference to FIG. 3K), it should be noted, that radial expansion of prosthetic valve 2042 against inner perimeter 2068 of upstream support portion 2041, thereby typically does not cause the prosthetic valve support to apply a radially-expansive force to the native valve annulus.

For some applications, the prosthetic valve is couplable to the upstream support portion at a continuum of positions along the axial length of the prosthetic valve. That is, a physician can couple the prosthetic valve to the support at a continuum of depths within the support. For example, in applications in which the prosthetic valve is configured to be coupled to the upstream support portion solely by the radially-expansive force, the prosthetic valve may be coupled to the upstream support portion at a continuum of positions along the length of the prosthetic valve.

As described hereinabove, the lattice structures of prosthetic valve 2042 and portion 2041 typically define a repeating arrangement of struts, e.g., a repeating arrangement of shapes. For some applications, and as shown in FIG. 1C, portion 2041 comprises the same number of arrangement repeats as does prosthetic valve 2042, at at least one transverse plane of the prosthetic valve. For some such applications, this matching number of repeats facilitates coupling of prosthetic valve 2042 and portion 2041. For example, and as shown in FIG. 1C, a number of inwardly-protruding ridges 2057 of portion 2041 protrude (e.g., interpose) within an equal number of corresponding circumferential voids defined by the lattice structure of prosthetic valve 2042. These ridges facilitate coupling of support 2040 and prosthetic valve 2042, e.g., by inhibiting axial movement of the prosthetic valve through opening 2045 of upstream support portion 2041.

Typically, the arrangement of repeating circumferential voids defined by the lattice structure of the prosthetic valve is repeated axially, thereby defining a prismatic (e.g., cylindrical) shape of the prosthetic valve. For some applications, the prosthetic valve is thereby couplable to the upstream support portion at a plurality of positions along the axial length of the prosthetic valve. That is, a physician can couple the prosthetic valve is couplable to the upstream support portion at a plurality of depths within the support. For example, in applications in which when a circumferential arrangement of voids is repeated four times along the axial length of the prosthetic valve, the prosthetic valve is typically couplable to the upstream support portion at four positions along the axial length of the prosthetic valve.

It is noted that, for some applications, the above descriptions of prosthetic valve 2042 and support 2040 are applicable to (e.g., the applications described above are combinable with) other embodiments of prosthetic valves and prosthetic valve supports described herein.

FIG. 1D shows an end view of an implant 2030a, comprising prosthetic valve 2042 coupled to a prosthetic valve support 2040a. For some applications of the invention, prosthetic valve support 2040a is analogous to other prosthetic valve supports (e.g., prosthetic valve support 2040) described herein, and implant 2030a is analogous to other implants (e.g., implant 2030) described herein. Prosthetic valve support 2040a comprises an upstream support portion 2041a. For some applications of the invention, upstream support portion 2041a is analogous to other upstream support portions described herein. Upstream support portion 2041a comprises a plurality of inwardly-protruding barbs 2102, protruding from inner perimeter 2068 into opening 2045, such that, when prosthetic valve 2042 is expanded within opening 2045, barbs 2102 protrude (e.g., interpose) into voids defined by the lattice structure of prosthetic valve 2042. Similarly to the protrusion of ridges 2057 (described with reference to FIG. 1C) the protrusion of barbs 2102 further facilitates coupling of prosthetic valve support 2040a and prosthetic valve 2042. For some applications, barbs 2102 are disposed on (e.g., protrude from) ridges 2057. For some applications, barbs 2102 are disposed between ridges 2057 (e.g., protrude from sites between ridges 2057).

Reference is made to FIG. 2, which is a schematic illustration of a prosthetic valve support 2040b, in accordance with some applications of the invention. For some applications of the invention, prosthetic valve support 2040b is analogous to other prosthetic valve supports (e.g., prosthetic valve support 2040) described herein. Support 2040b comprises upstream support portion 2041, coupled to one or more clips 2900, configured to be coupled to one or more native leaflets 2082 of the native valve (e.g., as described hereinbelow with reference to FIGS. 3A-L and 5A-F). For some applications of the invention, clips 2900 are analogous to tissue-engaging elements and/or support-anchoring elements (e.g., as described hereinabove with reference to FIG. 1A).

Typically, support 2040b comprises two clips 2900, coupled to portion 2041 at or near inner perimeter 2068. For some applications, clips 2900 are disposed opposite each other. For some applications (e.g., for prosthetic valve supports that are configured to be coupled to tri-leaflet valves, such as the tricuspid valve and/or the aortic valve), the prosthetic valve support comprises three clips, coupled to the upstream support portion.

Typically, clips 2900 are articulatably coupled to portion 2041. That is, typically, clips 2900 can move, at least in part, with respect to portion 2041. Typically, each clip 2900 is coupled to portion 2041 via a connector 2540, which facilitates this movement. Typically, but not necessarily, connector 2540 comprises a flexible material, such as a fabric, metal, and/or polymer. For some applications, connector 2540 comprises one or more hinge points, to facilitate the movement of the clips.

Each clip 2900 typically comprises two or more clip elements, such as a clip arm 2920 and a clip arm 2922, movable with respect to each other. Typically, the clip arms are articulatably-coupled at an articulation point 2921, and are movable with respect to each other by the relative angular disposition of the clip aims being controllable. Typically, clip 2900 is configured to be biased (e.g., pre-set, such as shape-set) to be in a closed configuration, such that aims 2920 and 2922 are relatively disposed at a generally small angle (e.g., less than 45 degrees, such as less than 20 degrees, such as less than 5 degrees) to each other. For some applications, in the closed configuration of clip 2900, arms 2920 and 2922 touch each other at a site that other than the articulation point.

Clips 2900 further have an open configuration, in which the angular disposition of the clip aims relative to each other is greater than in the closed configuration. Typically, in the open configuration, the clip arms are disposed at a relatively large angle (e.g., greater than 40 degrees, such as greater than 90 degrees, such as greater than 150 degrees, such as 180 degrees).

Each clip 2900 is configured to be coupled to a native leaflet of the native valve by enveloping the native leaflet when the clip is in the open configuration thereof, and clipping the leaflet between the clip arms when the clip subsequently moves toward the closed configuration thereof.

Typically, arm 2920 is substantially immobile, and arm 2922 is (1) biased to assume a first configuration, and (2) movable between the first configuration and another configuration. Typically, the first configuration of arm 2922 is a closed configuration. Typically, the other configuration of arm 2922 is an open configuration, whereby a portion of arm 2922 that is furthest from articulation point 2921 is disposed (1) further from arm 2920 than is the same portion in the first, closed configuration, and (2) further from arm 2920 than a portion of arm 2922 that is closest to the articulation point. That is, an angular disposition of arm 2922 to arm 2920 is greater when arm 2922 is in the open configuration thereof, than when arm 2922 is in the closed configuration thereof. When arm 2922 is in the closed configuration thereof, clip 2900 is in the closed configuration thereof. When arm 2922 is in the open configuration thereof, clip 2900 is in the open configuration thereof. That is, clip 2900 is movable between open and closed configurations thereof, by arm 2922 moving between open and closed configurations thereof. FIG. 2 shows detailed illustrations of clip 2900 in the open and closed configurations, and further shows an exploded view of the components of clip 2900.

Clip 2900 further comprises a clip-controller interface 2923, typically comprising a pull-wire 2924, which facilitates movement of arm 2922 between the closed and open configurations, i.e., relative angular movement of arms 2920 and 2922. Pull-wire 2924 is typically coupled to clip arm 2922, and controlled from outside the body of the subject. For example, pull-wire 2924 may be coupled to arm 2922, and extend to a clip controller (e.g., clip controller 2930, described with reference to FIGS. 3A-L) disposed within delivery apparatus, and ultimately controlled by a physician. Typically, pull-wire 2924 is coupled to arm 2922 such that (1) placing the pull-wire under tension (e.g., by pulling) moves arm 2922 toward the open configuration, and (2) releasing the tension, at least in part, allows the arm to return toward the closed configuration.

As described hereinabove (e.g., with reference to FIGS. 1A-D), upstream support portion 2041 is expandable from a compressed to an uncompressed configuration thereof. Clips 2900 are generally controllable (e.g., movable between the open and closed configurations thereof) irrespective of and/or independent to a state of expansion of the upstream support portion. For some applications of the invention, both clips 2900 are controlled simultaneously by a user (e.g., clips 2900 are configured to operate simultaneously). For some applications, each clip 2900 is controllable independently. For some applications, clip 2900 further comprises one or more grips, such as teeth 2928, which facilitate the clamping of leaflets 2082 when clip 2900 is closed. For some applications, clips 2900 may alternatively or additionally be coupled to the prosthetic valve, and configured to couple the prosthetic valve directly to the native valve.

Reference is made to FIGS. 3A-L, which are schematic illustrations of steps in the implantation of implant 2030b, comprising prosthetic valve 2042 and prosthetic valve support 2040b, in a native heart valve, such as mitral valve 2024 of a subject, in accordance with some applications of the invention.

Figure 3A:
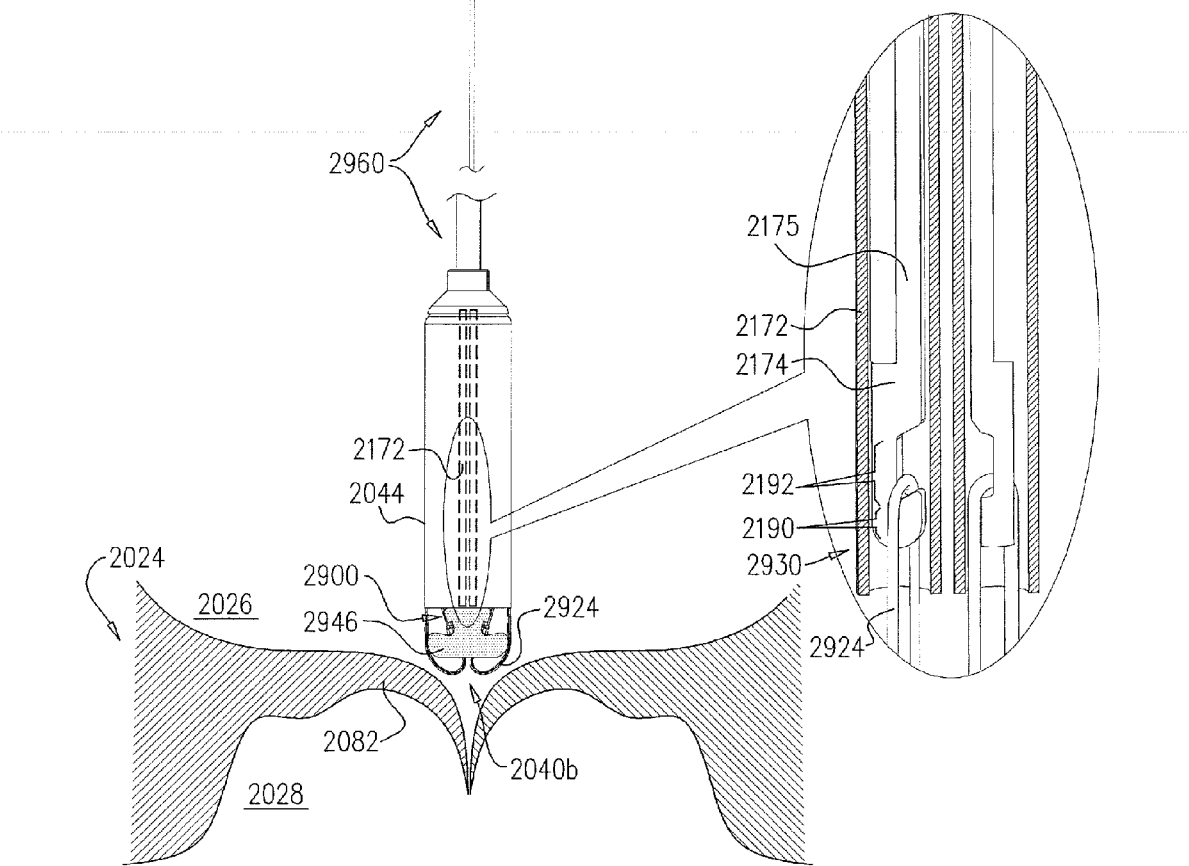
Figure 3A:
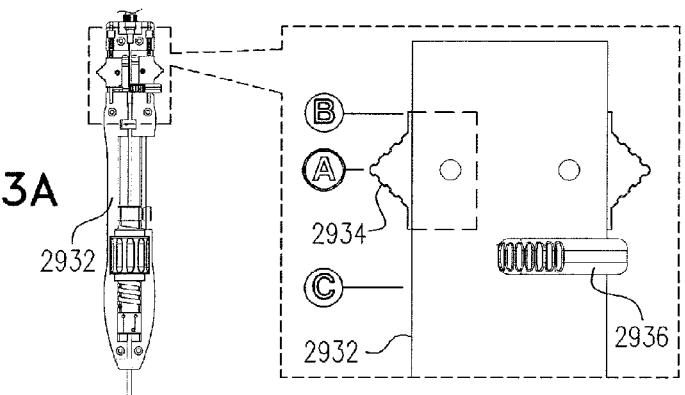

Prosthetic valve support 2040b is implanted using support-delivery apparatus, such as support-delivery apparatus 2960. As described hereinabove with reference to FIG. 2, each clip 2900 comprises a clip-controller interface, typically pull-wire 2924, which is configured to open the clip when pulled (i.e., placed under tension). For some applications of the invention, and as shown in FIG. 3A, support-delivery apparatus 2960 comprises at least one clip controller 2930, one end of pull-wire 2924 is coupled to clip arm 2922, and another end of the pull-wire is coupled to controller 2930. Controller 2930 comprises a tubular member 2172, shaped to define a lumen, and a plug 2174. Plug 2174 is dimensioned such that it is disposable in, and slidable through (e.g., within, into, and out of) the lumen of tubular member 2172. Plug 2174 comprises a restricting portion 2190 and a second portion 2192.

Typically, at least part of plug 2174 (e.g., restricting portion 2190) is dimensioned so as to fit tightly in the lumen of tubular member 2172, in a manner in which an outer surface of plug 2174 (e.g., an outer surface of portion 2190) is disposed very close to an inner surface of tubular member 2172, i.e., such that little space exists between the at least part of the plug and the tubular member. For example, the widest space between portion 2190 and member 2172 may be smaller than a thickness of pull-wire 2924. Typically, a surface of second portion 2192 is disposed further from the inner surface of tubular member 2172, than is the surface of the at least part of portion 2190.

Controller 2930 typically has at least three controller configurations, each configuration having a different relative disposition of plug 2174 within tubular member 2172. In a first controller configuration, plug 2174 is disposed at a first longitudinal position within tubular member 2172. In a second controller configuration, the plug is disposed at a second longitudinal position within the tubular member, the second position being more proximal (e.g., closer to a position outside the body; typically upstream) than the first longitudinal position. In a third controller configuration, the plug is disposed at a third longitudinal position, distal (e.g., downstream) to the first longitudinal position, such that at least restricting portion 2190 is disposed outside of (e.g., distal to) the tubular member.

Controller 2930 has at least one locking configuration, in which (1) at least part of restricting portion 2190 is disposed inside the lumen of tubular member 2172, and (2) pull-wire 2924, is generally not couplable to, and decouplable from, the controller. Typically, the first and second controller configurations, described hereinabove, are locking configurations. Controller 2930 further has at least one open configuration, in which (1) at least restricting portion 2190 is disposed outside the lumen of tubular member 2172, and (2) pull-wire 2924 is couplable to, and decouplable from, the controller. Typically, the third controller configuration, described hereinabove, is an open configuration. That is, (1) when pull-wire 2924 is coupled to the controller (e.g., is coupled to the plug, e.g., is in contact with second portion 2192 of the plug), and the controller is in the locking configuration thereof, the pull-wire is generally not decouplable from the controller, and (2) if/when controller moves into the open configuration thereof, the pull-wire is decouplable from the controller.

Typically, and as shown in FIG. 3A, pull-wire 2924 comprises, and/or is shaped to define, a loop, and is coupled to controller 2930 by at least part of the loop being disposed against second portion 2192 when the lock is in, or moves into, a locking configuration thereof. For some applications, pull-wire 2924 is generally flat (e.g., has an elongate transverse cross-section, e.g., is a strip), is shaped to define a hole, and is coupled to controller 2930 by at least part of restricting portion 2190 being disposed within the hole when the lock is in, or moves into, a locking configuration thereof. Restricting portion 2190 inhibits distal axial movement of the coupling wire, and tubular member 2172 inhibits lateral movement of the coupling wire (e.g., the inner surface of the tubular member holds the coupling wire against second portion 2192). Tubular member 2172 thereby facilitates coupling of pull-wire 2924 to plug 2174, and thereby to controller 2930.

Controller 2930 is typically controlled (e.g., the configurations of the controller, such as the disposition of plug 2174 within tubular member 2172, are typically selected), via a control rod 2175, using an extracorporeal controller, such as a control handle 2932, typically disposed at a proximal end of support-delivery apparatus 2960. Control handle 2932 comprises at least one adjuster 2934, each adjuster configured to control at least one clip 2900 of prosthetic valve support 2040b. Typically, control handle 2932 comprises two adjusters 2934, each adjuster configured to independently control one clip 2900. For clarity, however, adjusters 2934 are shown operating simultaneously. Typically, but not necessarily, adjuster 2934 has pre-defined positions in which it can reside, each pre-defined position of the adjuster corresponding to a respective configuration of controller 2930. That is, moving adjuster 2934 between the pre-defined positions thereof, moves controller 2930 between the configurations thereof. For illustrative purposes only, example pre-defined positions (A), (B) and (C) are indicated.

FIG. 3A shows support 2040b having been delivered, using support-delivery apparatus 2960, to left atrium 2026 of the heart of a subject (i.e., to a site upstream of native mitral valve 2024 of the subject). Support 2040b is typically delivered transcatheterally (e.g., transvascularly, such as transfemorally), while in a compressed configuration thereof (e.g., as described with reference to FIG. 1B for support 2040). Typically, support 2040b is delivered within an overtube 2044, which provides a constraining (e.g., compressive) force, to constrain the support in the compressed configuration thereof. Typically, upstream support portion 2041 of support 2040b is coupled to a scaffold, such as a core 2946, and constrained in the compressed configuration by being disposed within an overtube 2044 of the delivery apparatus. In the compressed configuration of support 2040b, clips 2900 are typically disposed downstream (e.g., distal) to the cylinder of upstream support portion 2041, and coupled to core 2946.

During delivery of support 2040b, and as shown in FIG. 3A, clips 2900 are typically in the closed configuration thereof. FIG. 3A shows clips 2900 exposed from the distal end of overtube 2044, overtube 2044 having been retracted (e.g., overtube 2044 having been moved proximally, and/or support 2040b having been moved distally). Adjuster 2934 of control handle 2932 is in a first position (A) (typically a middle position) thereof, and controller 2930 is in the first configuration thereof, whereby pull-wire 2924 is coupled to plug 2174, which is disposed within tubular member 2172.

FIG. 3B shows support 2040b and core 2946 having been moved closer to the native valve, and clips 2900 enveloping leaflets 2082 of the native valve. Adjuster 2934 of control handle 2932 is in a second position (B) thereof (typically more proximal than the first position), and controller 2930 is in the second configuration thereof. Movement of controller 2930 into the second configuration thereof (i.e., moving plug 2174 proximally) places pull-wire 2924 under tension (i.e., pulls the pull-wire), thereby pulling clip arm 2922, and opening clip 2900. Using support-delivery apparatus 2960, the position of prosthetic valve support 2040b is adjusted, so as to envelope native leaflets 2082 between the clip arms of clips 2900.

Figure 3C:
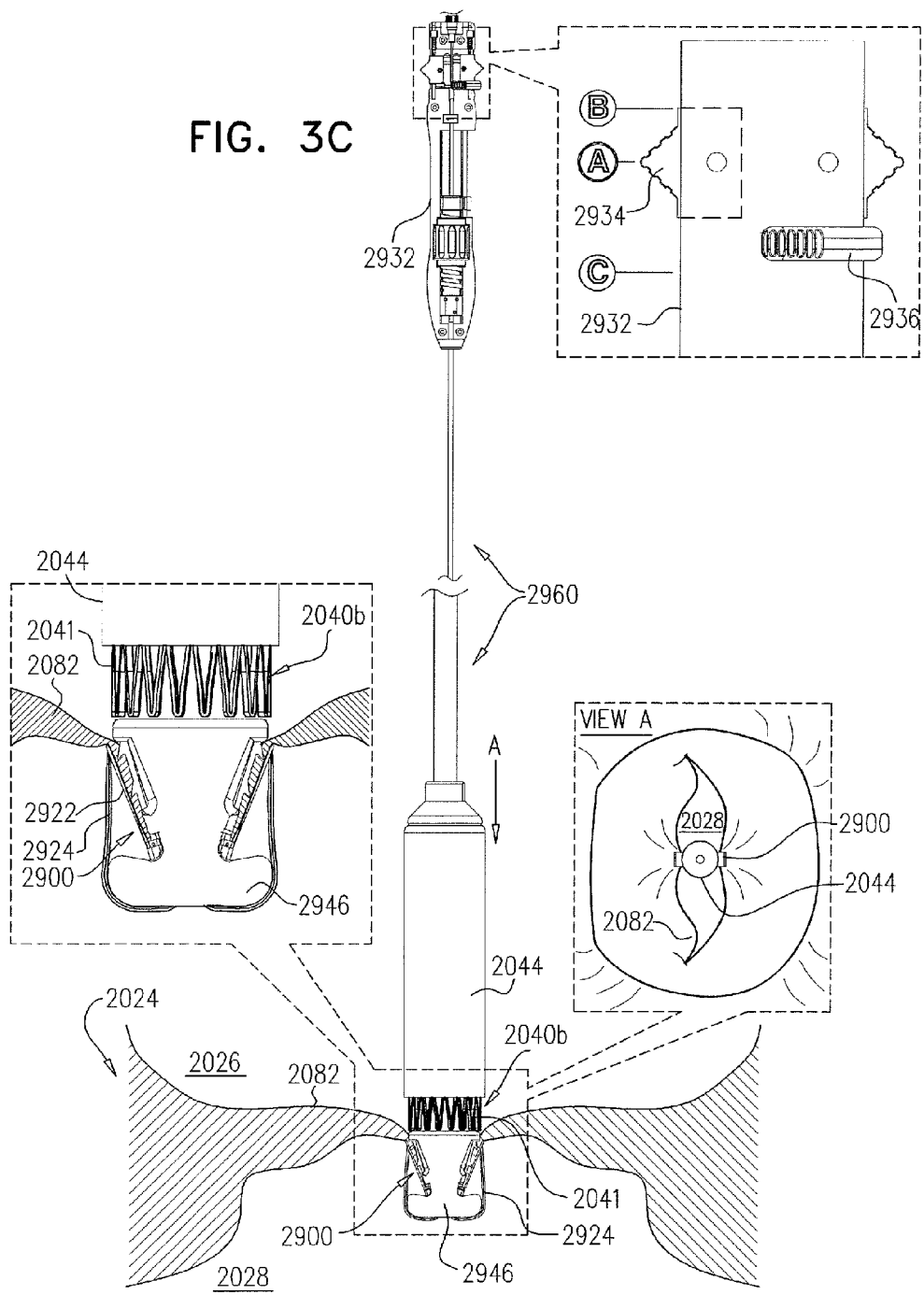

FIG. 3C shows clips 2900, coupled (i.e., clipped) to native leaflets 2082. The user (e.g., the physician) couples the clips to the native leaflets by closing the clips while the leaflets are enveloped by the arms of the clips. Adjuster 2394 of control handle 2932 is in first position (A) thereof (i.e., has been returned to first position (A)), and controller 2930 is in the first configuration thereof (i.e., has been returned to the first configuration thereof). For some applications of the invention, control handle 2932 comprises a spring, which facilitates the return of adjuster 2394 to first position (A). For example, a user may apply a force to adjuster 2394 so as to move the adjuster to second position (B), and remove the force (e.g., release the adjuster) so as to return the adjuster to first position (A). Movement of controller 2930 into the first configuration thereof (i.e., moving plug 2174 distally) at least partly releases the tension on pull-wire 2924, allowing the bias of clip 2900 (e.g., of clip arm 2922) to return the clip toward the closed configuration. If a native leaflet 2082 is enveloped by the clip arms, the leaflet is sandwiched between the arms, thereby coupling the clip to the leaflet.

As described hereinabove (e.g., with reference to FIG. 2), clips 2900 are generally controllable (e.g., movable between the open and closed configurations thereof) irrespective of and/or independent to a state of expansion of the upstream support portion. It is to be noted that in FIGS. 3A-C, upstream support portion 2041 of prosthetic valve support 2040b remains in the compressed configuration thereof, within overtube 2044, during the opening and closing of clips 2900 and the coupling of the clips to the native leaflets. That is, clips 2900 are closeable without expanding the prosthetic valve support. That is, clips 2900 are generally movable between the open and closed configurations thereof, irrespective of and/or independent to a state of deployment of the upstream support portion.

For some applications, visualization (e.g., imaging) techniques such as ultrasound are used to facilitate and/or confirm the coupling of clips 2900 to leaflets 2082. For example, an echocardiogram may be used to observe native leaflets 2082, and movement thereof. For some applications, coupling of both native leaflets by clips 2900 is accompanied by a generally lemniscate (e.g., 'figure 8') arrangement of the native leaflets, as shown in View A of FIG. 3C. Clips 2900 may be repeatedly opened and closed until coupling of the clips to leaflets 2082 has been achieved.

For some applications of the invention, clips 2900 further comprise a securing element (not shown), configured to secure the clips in the closed configuration, following coupling of the clips to the native leaflets. For some applications of the invention, the securing element is configured to secure the clips in one or more pre-defined closed configurations (e.g., in a partially-closed configuration).

Reference is made to FIG. 3D. Following coupling of clips 2900 to native leaflets 2082, the clips are released (e.g., decoupled) from support-delivery apparatus 2960 (e.g., from core 2946) by decoupling pull-wire 2924 from controller 2930. Until clips 2900 are released (e.g., until pull-wire 2924 is decoupled from controller 2930), prosthetic valve support 2040b is typically entirely retrievable from the body of the subject, e.g., by decoupling the clips from the native leaflets, and withdrawing support 2040b and delivery apparatus 2960 from the body of the subject.

To decouple the pull-wire from the controller, the user moves adjuster 2394 of control handle 2932 to third position (C) thereof (typically a distal position), thereby moving controller 2930 in the third configuration thereof, whereby at least restricting portion 2190 of plug 2174 is disposed outside of tubular member 2172. For some applications of the invention, control handle 2932 comprises a safety device, such as a safety lock 2936, configured to prevent inadvertent movement of adjuster 2394 into position (C), and thereby inadvertent release of clips 2900. For such applications, safety lock is disabled (e.g., removed) prior to releasing clips 2900.

Movement of controller 2930 into the third position thereof (i.e., moving at least part of plug 2174 outside of tubular member 2172) allows pull-wire 2924 to decouple from the controller. For some applications, pull-wire 2924 is configured to automatically decoupled from the controller when the controller moves into the third position. For example, the pull-wire may comprise a shape-memory (e.g., resilient, pseudoelastic and/or superelastic) material configured to lift the loop of the pull-wire away (e.g., laterally away) from plug 2174 when restricting portion 2190 moves outside of the tubular member. Non-limiting examples of materials that pull-wire 2924 may comprise include nickel-titanium (Nitinol), stainless steel, nickel cobalt, cobalt chrome, titanium, tantalum, palladium, polyester, PTFE, nylon, and cotton. For some applications of the invention, pull-wire 2924 is biodegradable (e.g., biosorbent).

Thereby, controller 2930 is configured to (1) be coupled to the clip-controller interface (e.g., to pull-wire 2924), (2) control a relative angular disposition of the clip arms (i.e., a state of openness of the clips), and (3) be decoupled from the clip-controller interface.

Reference is now made to FIG. 3E. Following the decoupling of clips 2900 from controller 2930, upstream support portion 2041 of prosthetic valve support 2040b is deployed (e.g., released from overtube 2044). Typically, overtube 2044 is withdrawn proximally, exposing successively more proximal (e.g., upstream) parts of portion 2041. As described hereinabove (e.g., with reference to FIG. 1A), portion 2041 typically comprises a shape-memory material, and is compressed prior to implantation. Portion 2041 thereby automatically expands upon removal of the constraining (e.g., compressive) force, i.e., when overtube 2044 is withdrawn.

Immediately prior to the release of prosthetic valve support 2040b from the overtube, the total length of overtube 2044 and support 2040b may be double or more than that of the overtube or support alone. For some applications, this extra length can hinder the movement and/or removal of the overtube from the body of the subject. For some applications, overtube 2044 comprises a flexible and/or soft material, such as a fabric or polymer, thereby becoming flexible as support 2040b is removed from within the overtube. It is hypothesized that this composition/configuration of overtube 2044 facilitates deployment of support 2040b, and removal of the overtube from the body of the subject.

Figure 3F:
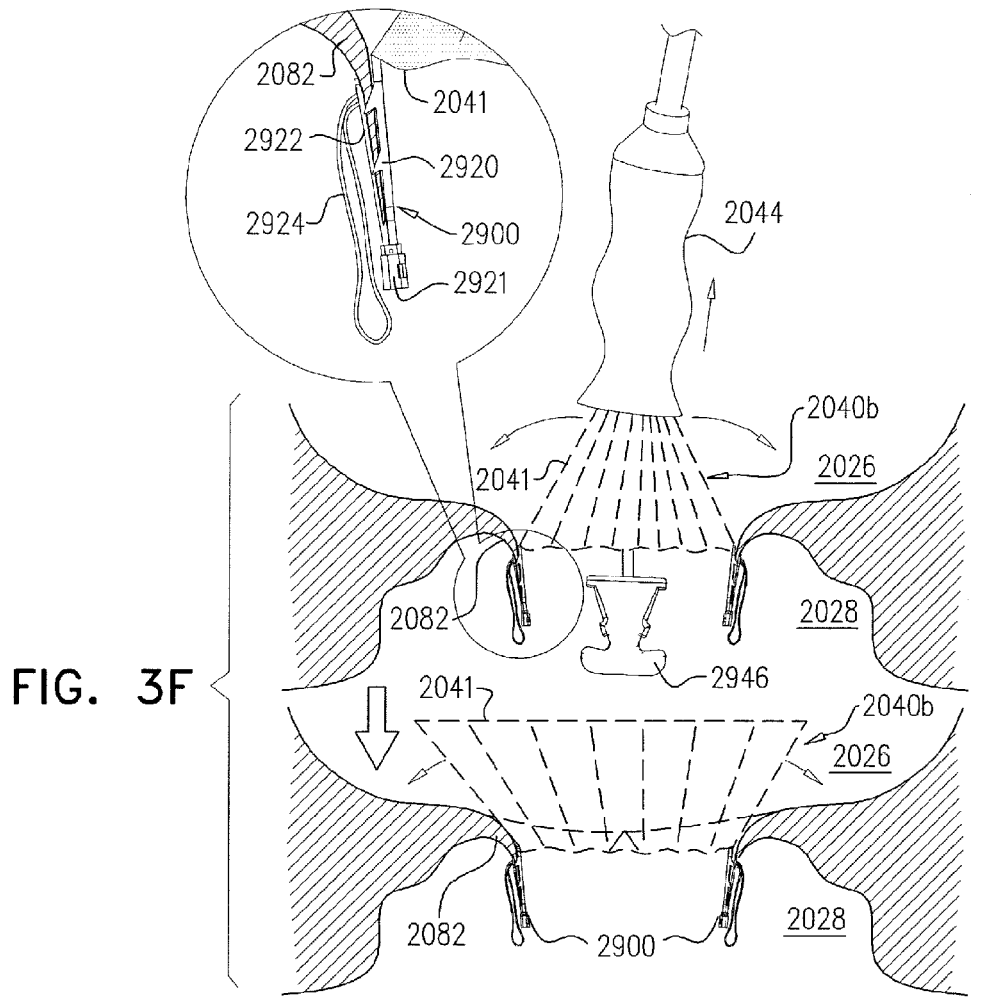

FIG. 3F shows prosthetic valve support 2040b during deployment thereof. Typically, and as described hereinabove, when upstream support portion 2041 is delivered to the native valve in the cylindrical, compressed configuration, downstream (e.g., distal) end 2053 of the cylinder has perimeter 2068b, which is a compressed inner perimeter 2068. Distal end 2053, and therefore the inner perimeter of portion 2041, is thereby coupled to the native valve before deploying (e.g., expanding) upstream (e.g., proximal) end 2055, and therefore the outer perimeter of portion 2041. That is, the inner perimeter of portion 2041 typically engages the native valve before the outer perimeter.

The two phases illustrated in FIG. 3F illustrate typical behavior of upstream support portion 2041 during deployment thereof. As downstream end 2053, moves out of overtube 2044, it expands toward becoming and/or defining inner perimeter 2068 of portion 2041. As upstream end 2055 moves out of overtube 2044, it expands to become outer perimeter 2069. Due to this arrangement, during deployment, upstream end 2055 typically expands more than does downstream end 2053. For some applications, upstream end 2055 expands more than 1.5 times (e.g., more than twice) as much as does downstream end 2053.

Figure 3G:
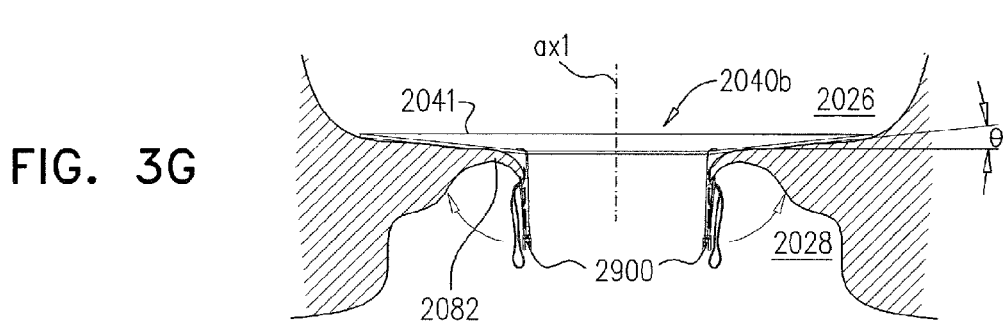
Figure 3H:
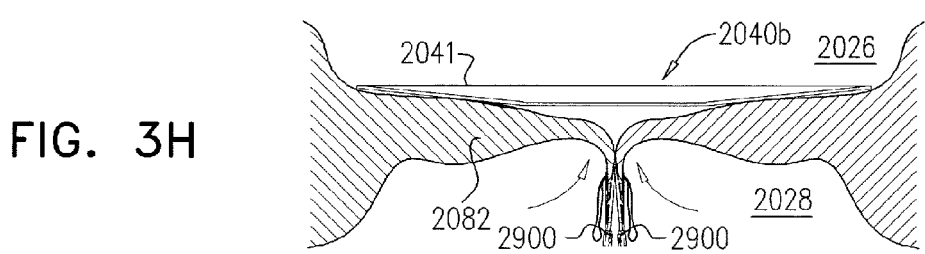

Reference is now made to FIGS. 3G-H, which show support 2040b in the implanted configuration thereof. Upstream support portion 2041 is described hereinabove (e.g., with reference to FIG. 1A) as being generally flat when in its fully uncompressed configuration. However, portion 2041 is typically at least partly resilient. For example, as described hereinabove, portion 2041 typically comprises a shape-memory material. Implanting support 2040*b*, as described with reference to FIGS. 3A-F, disposes portion 2041 against the upstream side of the native valve (e.g., the upstream side of the native valve annulus). Typically, portion 2041 is held tightly against the upstream side of the native valve by clips 2900, and deforms responsively to the contours of the native tissue (e.g., conforms to the native annulus), thereby assuming an implanted configuration. For some applications, portion 2041 repeatedly deforms responsively to the contours of the native tissue, as the native tissue repeatedly changes shape with the cardiac cycle.

Upstream support portion 2041 and clips 2900 are typically configured such that, when support 2040*b* is implanted at the native valve, upstream support portion inhibits downstream (e.g., ventricular) movement of support 2040*b*, and clips 2900 inhibit upstream (e.g., atrial) movement of the support. Typically, clips 2900 are configured to couple the prosthetic valve support to the native valve such that upstream support portion 2041 is in contact with the upstream side of the native valve (e.g., with the upstream side of the native annulus). For some applications, clips 2900 are the only component of prosthetic valve support 2040*b* that inhibits upstream movement of prosthetic valve support.

The dimensions of upstream support portion 2041 in the implanted configuration thereof are typically similar to those of the same portion in the fully uncompressed configuration thereof, with any difference between the configurations typically due to the portion being implanted. For example, in some applications in which upstream support portion 2041 is generally flat in the fully uncompressed (e.g., unconstrained uncompressed) configuration thereof, when support 2040*b* is implanted at the native valve, clips 2900 apply a downstream force to inner perimeter 2068 of upstream support portion 2041, thereby inducing portion 2041 to assume a frustoconical shape in the implanted configuration thereof. When upstream support portion 2041 is generally frustoconical in the implanted configuration thereof, a surface of portion 2041 typically has an angle θ (theta) of less than 60 degrees (e.g., less than 45 degrees) from a plane of the smaller base of the frustum. (As shown in FIG. 3G, for example, angle θ (theta) is approximately 10 degrees.) That is, when upstream support portion 2041 is generally frustoconical in the implanted configuration thereof, portion 2041 is closer to being planar than it is to being cylindrical. Alternatively, the surface of portion 2041 has an angle of greater than 60 degrees from the smaller base of the frustum. It is to be noted that, although upstream support portion 2041 is generally described herein in terms of symmetrical geometric shapes (e.g., ellipse and frustum), when conforming to native tissue, the upstream support portion may assume a symmetrical or an unsymmetrical shape.

Thus, in general, as shown in and described with reference to FIGS. 1A-3L, (1) the fully uncompressed configurations of upstream support portion 2041 described with reference to FIG. 1A are typically unconstrained uncompressed configurations, (2) the compressed configurations of portion 2041 described with reference to FIG. 1B are typically constrained compressed configurations, and (3) the implanted configurations of portion 2041 described with reference to FIG. 3F are typically constrained uncompressed configurations.

When implanted at the native valve, and thereby in the implanted configuration thereof, no part of upstream support portion 2041 is disposed downstream of native leaflets 2082 (e.g., no part of portion 2041 is disposed in ventricle 2028). Typically, when prosthetic valve support 2040*b* is implanted at the native valve, no part of support 2040*b* that circumscribes a space that has a perimeter greater than 60 mm (e.g., opening 2045) is disposed downstream of the native leaflets.

For some applications, when prosthetic valve support 2040*b* is implanted at the native valve, no part of support 2040*b* that circumscribes a space that has a perimeter greater than 60 mm is disposed downstream of the native annulus.

When implanted at the native valve, and thereby in the implanted configuration thereof, a height (i.e., a length along an upstream-to-downstream axis ax1 from a most upstream end to a most downstream end) of upstream support portion 2041, is typically less than 20 mm (e.g., less than 10 mm, such as less than 5 mm). Typically, when prosthetic valve support 2040*b* is implanted at the native valve, no part of the support that circumscribes a space that has a perimeter greater than 60 mm has a height of more than 20 mm. For some applications, when prosthetic valve support 2040*b* is implanted at the native valve, no part of the support that circumscribes a space that has a perimeter greater than 60 mm has a height of more than 10 mm. For some applications, when prosthetic valve support 2040*b* is implanted at the native valve, no part of the support that circumscribes a space that has a perimeter greater than 60 mm has a height of more than 5 mm.

As described hereinabove with reference to FIG. 2, clips 2900 are articulatably-coupled to upstream support portion 2041 of prosthetic valve support 2040*b*. Following the implantation (e.g., delivery, coupling and deployment) of prosthetic valve support 2040*b*, clips 2900 can move, at least in part, with respect to portion 2041, thereby allowing native leaflets 2082 to continue to function, at least in part. That is, implantation of prosthetic valve support 2040*b* at a native valve, does not eliminate the native blood flow regulation functionality of the native valve.

FIGS. 3G-H show such movement of native leaflets 2082, and clips 2900. FIG. 3G shows support 2040*b* implanted at mitral valve 2024, with native leaflets 2082 open (e.g., during ventricular diastole), clips 2900 having moved away from each other. FIG. 3H shows support 2040*b* implanted at mitral valve 2024, with native leaflets 2082 closed (e.g., during ventricular systole), clips 2900 having moved toward each other. Typically, each clip moves through an arc of greater than 45 degrees (e.g., greater than 60 degrees, such as greater than 80 degrees) during each cardiac cycle.

For applications in which support 2040*b* is implanted at a native tricuspid valve, clips 2900 similarly typically move away from each other during ventricular diastole, and toward each other during ventricular systole. For applications in which support 2040*b* is implanted at a native semilunar valve (e.g., the aortic valve or the pulmonary valve), clips 2900 typically move toward each other during ventricular diastole, and away from each other during ventricular systole.

FIGS. 3I-L show steps in the implantation of prosthetic valve 2042 in opening 2045 of prosthetic valve support 2040*b*. As described hereinabove, prosthetic valve 2042 is typically delivered transcatheterally. Typically, prosthetic valve 2042 is delivered to the native valve from an upstream side (e.g., the atrial side of the mitral valve), in a compressed configuration, and constrained within a delivery tube 2060, as shown in 3I. The prosthetic valve and delivery tube are typically placed within opening 2045. Delivery tube 2060 is then withdrawn from the prosthetic valve. Typically, the delivery tube is withdrawn in a downstream direction (e.g., distally and/or ventricularly), as shown in FIG. 3J. For some applications, the delivery tube is withdrawn in an upstream direction (e.g., proximally and/or atrially).

Figure 3K:
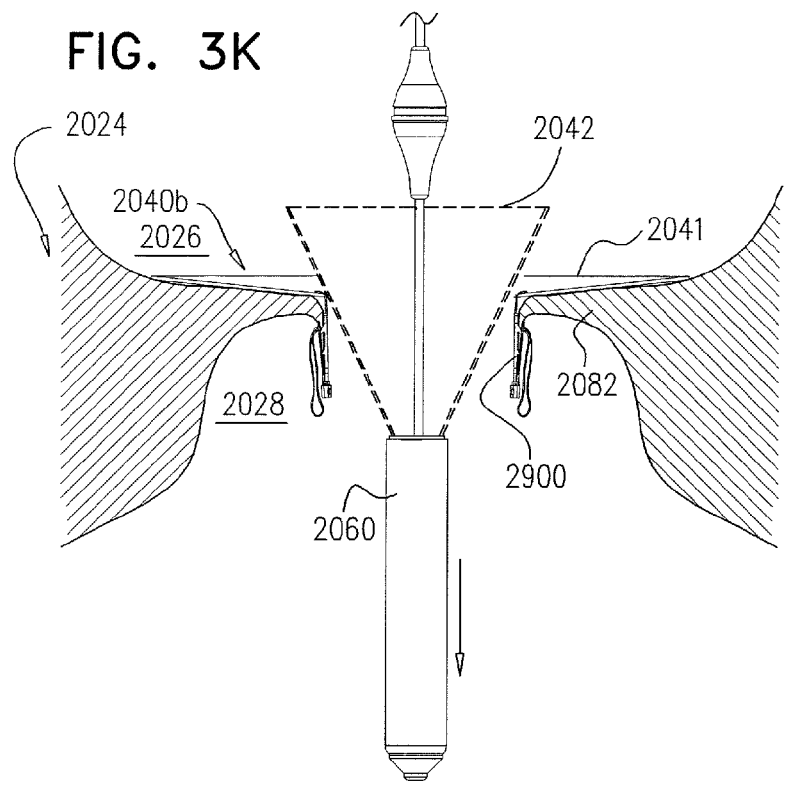

As regions of prosthetic valve 2042 are successively exposed as they exit delivery tube 2060, they expand (e.g., radially). When delivery tube 2060 is withdrawn in the downstream direction, the upstream end of the prosthetic valve is exposed, and expands, thereby coupling the prosthetic valve to the upstream support portion of prosthetic valve support 2040b, as shown in FIG. 3K (in which prosthetic valve 2042 is represented by a trapezoid/frustum). As described hereinabove (e.g., with reference to FIG. 1C), for some applications, the prosthetic valve is couplable to the upstream support portion at a plurality of positions along the axial length of the prosthetic valve. For such applications, a physician can typically implant (e.g., couple to support 2040b) the prosthetic valve at a plurality of depths with respect to upstream support portion 2041 and/or the native valve. For some such applications, the physician can implant the prosthetic valve prosthetic valve is implantable at a continuum of depths with respect to upstream support portion 2041 and/or the native valve.

As shown in FIG. 3K, upstream support portion 2041 is placed against the upstream side of the native valve, and prosthetic valve 2042 is radially expanded within opening 2045 defined by the upstream support portion. Radially-expansive force applied by prosthetic valve 2042 to upstream support portion 2041 (and which typically couples the prosthetic valve to the upstream support portion), is thereby typically not transferred to the native valve annulus via the prosthetic valve support. That is, and as described hereinabove (e.g., with reference to FIGS. 1A and 1C), radial expansion of prosthetic valve 2042 against inner perimeter 2068 of upstream support portion 2041, typically does not cause the prosthetic valve support to apply a radially-expansive force to the native valve annulus.

Typically, until delivery tube 2060 is fully withdrawn from prosthetic valve 2042 (e.g., until prosthetic valve 2042 is fully deployed), the prosthetic valve may be repeatedly recompressed and uncompressed by being withdrawn into, and exposed from, the delivery tube. This facilitates repositioning of the prosthetic valve with respect to prosthetic valve support 2042, by the physician, before full deployment of the prosthetic valve. Furthermore, until delivery tube 2060 is fully withdrawn from prosthetic valve 2042 (e.g., until prosthetic valve 2042 is fully deployed), the prosthetic valve is typically entirely retrievable from the body of the subject. For example, the delivery tube may be slid back over the prosthetic valve, re-compressing the prosthetic valve into the compressed configuration thereof, and the prosthetic valve and delivery tube subsequently withdrawn from the body of the subject.

Figure 3L:
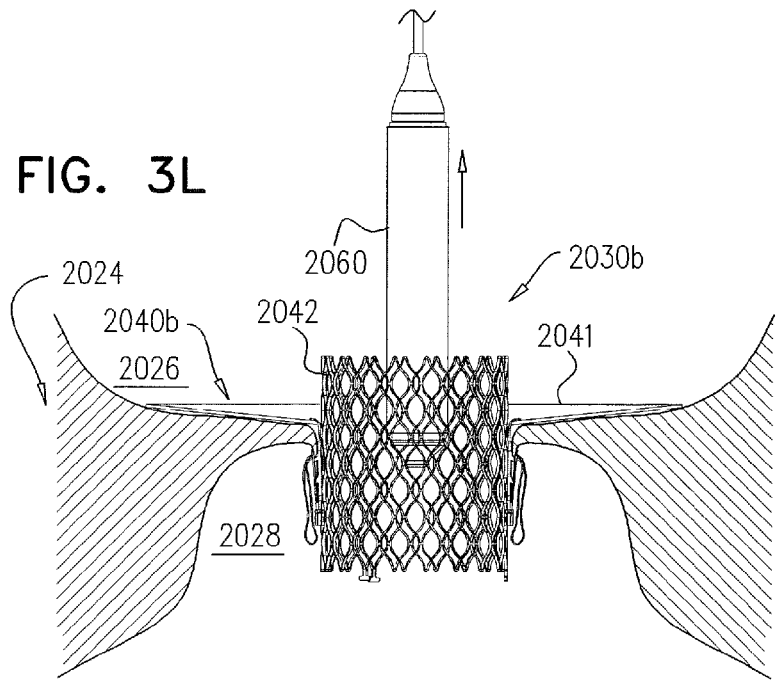

Once delivery tube 2060 is fully withdrawn from prosthetic valve 2042, and the prosthetic valve is fully deployed (e.g., in the implanted configuration thereof), the prosthetic valve thereby assumes its implanted configuration, in which it is coupled to prosthetic valve support 2040b. In this configuration, the prosthetic valve thereby replaces the native blood flow regulation functionality of the native valve with a substitute blood flow regulation functionality, provided by the check valve element disposed in the lumen of the primary structural element of the prosthetic valve. Delivery tube 2060 is subsequently removed from the body of the subject. For some applications, when the delivery tube is withdrawn in the downstream direction (e.g., ventricularly), it is removed from the body via the lumen of the prosthetic valve, as shown in FIG. 3L.

As described hereinabove (e.g., with reference to FIGS. 2 and 3G-H), following the implantation (e.g., delivery, coupling and deployment) of prosthetic valve support 2040b, clips 2900 and native leaflets 2082 can move, at least in part, thereby not eliminating the native blood flow regulation functionality of the native valve. In experiments conducted by the inventors, prosthetic valve support 2040b has been implanted in two pigs. Both animals remained alive and stable (e.g., had stable blood pressure, pulse, breathing rate and oxygen saturation) for a duration of sufficient length to withdraw the support-delivery apparatus, introduce a valve-delivery system (e.g., delivery tube 2060), and deploy (e.g., implant) prosthetic valve 2042 in opening 2045 of the support. The period between implanting support 2040b and implanting prosthetic valve 2042 was between 5 and 10 minutes. During this duration, the native valve of the animals functioned generally normally. For example, native leaflet movement and coaptation, and blood flow therebetween was generally normal during this duration.

It is thereby hypothesized that, following implantation of prosthetic valve support 2040b, the heart of the subject is able to continue pumping blood sufficiently to support the subject for longer than a minute, e.g., longer than 2 minutes, e.g., longer than 5 minutes, such as longer than an hour. It is thereby hypothesized that a period of generally normal physiological activity of the subject of up to a minute, e.g., up to 2 minutes, e.g., up to 5 minutes, such as up to an hour, between implantation of support 2040b and implantation of prosthetic valve 2042 (e.g., as described with reference to FIGS. 3I-L and/or 5D-E), is supported by prosthetic valve support 2040b. It is thereby hypothesized that the implantation of implant 2030b, comprising support 2040b and prosthetic valve 2042, may be performed without the use of cardiopulmonary bypass. It is thereby hypothesized that replacement of a native valve with implant 2030b, may be performed in a human, 'off-pump,' as was performed in the pig experiments.

Reference is again made to FIGS. 2 and 3A-L. It should be noted that clips 2900, clip-controller interface (e.g., pull-wire 2924), clip controller 2930, and/or the support-delivery apparatus (e.g., support-delivery apparatus 2930) are typically configured such that the clips are controllable independently of the deployment (e.g., expansion) of the prosthetic valve support (e.g., the withdrawal of overtube 2044 from upstream support portion 2041). That is, clips 2900 are typically configured to be controllable independently of a state of deployment of the prosthetic valve support. Thus, a physician may independently control (1) the coupling (e.g., 'clipping') of clips 2900 to the leaflets of the native valve, and (2) the deployment of the prosthetic valve support (e.g., expansion of the upstream support portion).

Reference is made to FIGS. 4A-E, which are schematic illustrations of implant 2030c, comprising prosthetic valve 2042 and prosthetic valve support 2040c, and the implantation thereof, in accordance with some applications of the invention. For some applications of the invention, prosthetic valve support 2040c is analogous to other prosthetic valve supports (e.g., prosthetic valve support 2040), and implant 2030c is analogous to other implants (e.g., implant 2030) described herein. Support 2040c comprises upstream support portion 2041, coupled to one or more clips 2900, described hereinabove (e.g., with reference to FIGS. 2 and 3A-L), and configured to be couplable to one or more native leaflets 2082 of the native valve. Typically, support 2040c comprises two clips 2900, coupled to portion 2041 at or near inner perimeter 2068. For some applications, clips 2900 are disposed opposite each other. Support 2040c further comprises a stabilizing element 3062, coupled to clips 2900.

Figure 4A:
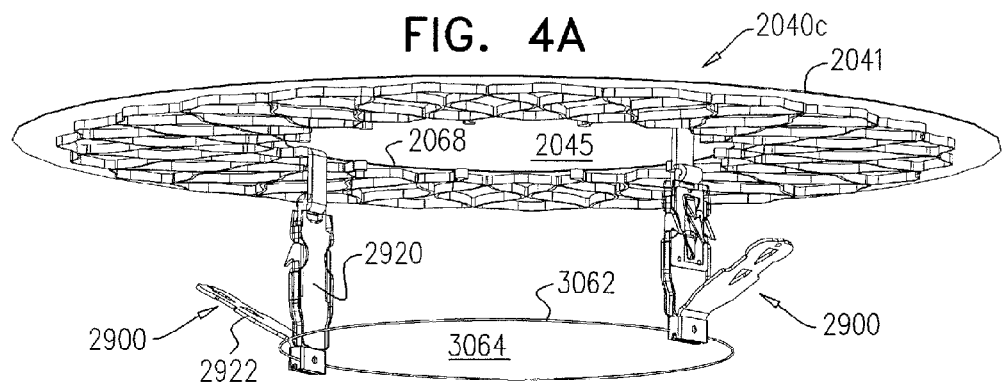
FIGS. 4A-D are schematic illustrations of an implant, comprising a prosthetic valve support and a prosthetic valve, and steps in the implantation thereof, in accordance with some applications of the invention.

Reference is now made to FIG. 4A, which shows a lower side view of support 2040c. Typically, stabilizing element 3062 is coupled to a downstream (e.g., distal) portion of clips 2900, and forms a ring shape downstream (e.g., distal) to upstream support portion 2041. Stabilizing element 3062 defines an aperture 3064, and is typically inelastic and at least partly flexible. Non-limiting examples of materials that element 3062 may comprise include polyester, PTFE (e.g., ePTFE), nylon, cotton, nitinol, stainless steel, nickel cobalt, cobalt chrome, titanium, tantalum and palladium. The flexibility of element 3062 typically facilitates the compressibility of the prosthetic valve support (e.g., for delivery) and/or movement (e.g., articulation) of clips 2900 with respect to upstream support portion 2041.

Stabilizing element 3062 is hypothesized to increase the stability of prosthetic valve support 2040c at the native valve. For example, element 3062 is hypothesized to at least partly inhibit lateral movement (e.g., rotation around an atrial-ventricular axis, e.g., 'yaw') of the support and/or clips, when the support is implanted at the native valve. Element 3062 is further hypothesized to reduce rolling movement (e.g., movement around a lateral axis, e.g., an axis between two clips 2900, e.g., 'pitch' and 'roll') of implant 2030c, including inversion (e.g., 'flipping') of the implant, following deployment (e.g., implantation) of prosthetic valve 2042.

For some applications of the invention, stabilizing element 3062 is further hypothesized to stabilize clips 2900 during deployment of the elements, e.g., by facilitating coupling thereof to delivery apparatus, such as apparatus 2960.

Figure 4B:
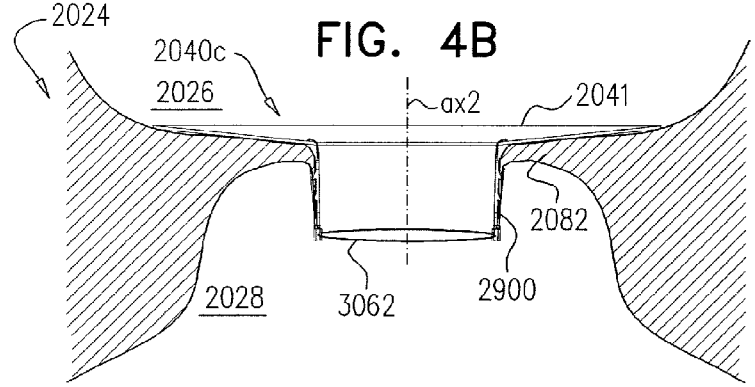
Figure 4C:
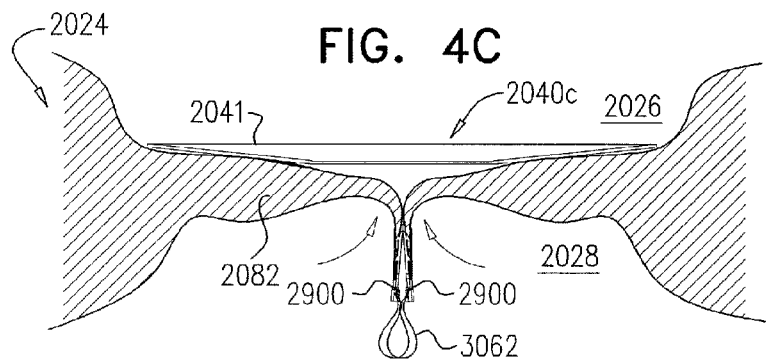

FIGS. 4B-C show prosthetic valve support 2040c, following implantation thereof at mitral valve 2024. As described hereinabove, the upstream support portion is disposed upstream of the native valve. Stabilizing element is disposed downstream of the native valve (i.e., in ventricle 2028). Prosthetic valve support 2040c is typically implanted as described elsewhere herein for other prosthetic valve supports, mutatis mutandis. As described hereinabove, stabilizing element 3062 is typically at least partly flexible, such that clips 2900 are movable with respect to upstream support portion 2041. Typically, element 3062 is sufficiently flexible to allow native leaflets 2082 to continue to function, at least in part. FIG. 4B shows support 2040c implanted at mitral valve 2024, with native leaflets 2082 open (e.g., during ventricular diastole). FIG. 4C shows support 2040c implanted at mitral valve 2024, with native leaflets 2082 closed (e.g., during ventricular systole). For some applications, when the native leaflets close, stabilizing element 3062 deforms toward a generally lemniscate (e.g., 'figure-8' or 'butterfly') configuration (e.g., as shown in FIG. 4C).

For some applications of the invention, a similar generally lemniscate configuration is formed by element 3062 when prosthetic valve support 2040c is coupled to delivery apparatus, during delivery to the native valve (e.g., as described for support 2040b with reference to FIGS. 3A-B). For some such applications, stabilizing element 3062 protrudes from the compressed prosthetic valve support, and facilitates positioning and/or orientation of the support. For example, the 'limbs' of the lemniscate are typically oriented at right angles to clips 2900, and protrude from the compressed support. When the clips are in close proximity to the native leaflets, the 'limbs' are typically downstream of the leaflets, and interact (e.g., touch) chordae tendineae of the native valve. By orienting the prosthetic valve support such that the 'limbs' have the least interaction with chordae tendineae (typically when the 'limbs' are oriented toward commissures of the native valve), a user automatically orients clips 2900 toward leaflets 2082 of the native valve.

Similarly to support 2040b (described with reference to FIGS. 3A-L), implantation of prosthetic valve support 2040c at a native valve does not eliminate the native blood flow regulation functionality of the native valve. It is thereby hypothesized that, following implantation of prosthetic valve support 2040c, the heart of the subject is able to continue pumping blood sufficiently well to support the physiological systems of the subject for longer than a minute, e.g., longer than 2 minutes, e.g., longer than 5 minutes, such as longer than an hour. It is thereby hypothesized that a period of up to a minute, e.g., up to 2 minutes, e.g., up to 5 minutes, such as up to an hour, between implantation of support 2040c and implantation of a prosthetic valve (e.g., prosthetic valve 2042), is supported by prosthetic valve support 2040c. It is thereby hypothesized that the implantation of implant 2030c, comprising support 2040c and prosthetic valve 2042, may be performed without the use of cardiopulmonary bypass. That is, it is hypothesized that replacement of a native valve with implant 2030c, may be performed 'off-pump'.

When implanted at the native valve, and thereby in the implanted configuration thereof, no part of stabilizing element 3062 is disposed upstream of native leaflets 2082 (e.g., no part of element 3062 is disposed in atrium 2026). Typically, when prosthetic valve support 2040c is implanted at the native valve, no part of support 2040c that circumscribes a space that has a perimeter greater than 60 mm traverses (e.g., fully traverses) the native annulus. For example, portion 2041 (which circumscribes opening 2045) and stabilizing element 3062 (which circumscribes aperture 3064), typically do not traverse (e.g., fully traverse) the native annulus.

When implanted at the native valve, and thereby in the implanted configuration thereof, a height (i.e., a length along an upstream-to-downstream axis ax2 from a most upstream part to a most downstream part) of stabilizing element 3062, is typically less than 20 mm (e.g., less than 10 mm, such as less than 5 mm). For example, stabilizing element 3062 typically has a thickness of less than 20 mm (e.g., less than 10 mm, e.g., less than 5 mm, such as less than 1 mm). Typically, when prosthetic valve support 2040c is implanted at the native valve, no part of the support that circumscribes a space that has a perimeter greater than 60 mm has a height of more than 20 mm. For some applications, when prosthetic valve support 2040c is implanted at the native valve, no part of the support that circumscribes a space that has a perimeter greater than 60 mm has a height of more than 10 mm. For some applications, when prosthetic valve support 2040c is implanted at the native valve, no part of the support that circumscribes a space that has a perimeter greater than 60 mm has a height of more than 5 mm.

Figure 4D:
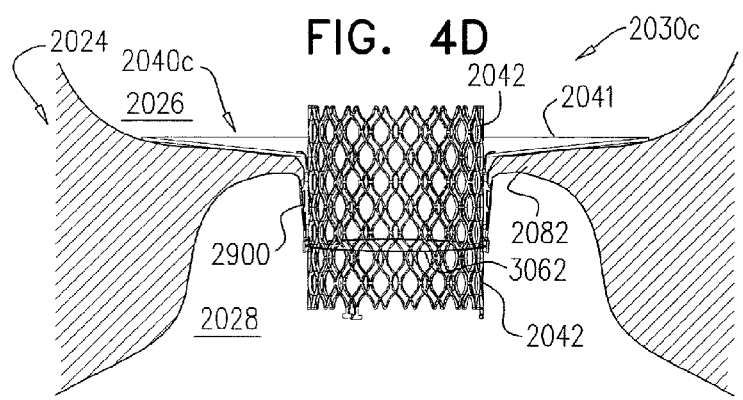

FIG. 4D shows implant 2030, comprising prosthetic valve support 2040c and prosthetic valve 2042, following implantation at mitral valve 2024. The prosthetic valve is typically implanted as described elsewhere herein (e.g., with reference to FIGS. 3I-L), mutatis mutandis. Prosthetic valve 2042 is deployed (e.g., delivered and expanded) in opening 2045, defined by upstream support portion 2041, and in aperture 3064, defined by stabilizing element 3062. That is, when prosthetic valve 2042 is deployed at the native valve, it is expanded such that (1) an upstream (e.g., proximal) portion of the prosthetic valve engages (e.g., couples to) inner perimeter 2068 of support 2040c, and (2) a downstream (e.g., distal) portion of the prosthetic valve is disposed within the aperture of the stabilizing element. For some applications of the invention, and as illustrated in FIG. 4D, the distal portion of the prosthetic valve engages (e.g., couples to) the stabilizing element.

For some applications of the invention, stabilizing element 3062 is configured (e.g., dimensioned) such that, when the prosthetic valve is expanded within the aperture of the stabilizing element, the stabilizing element restricts the full expansion of the downstream portion of the prosthetic valve. That is, for some applications, upon expansion of the prosthetic valve, a transverse cross-sectional dimension (e.g., area) defined by a downstream portion of the prosthetic valve is determined (e.g., restricted) by a transverse cross-sectional dimension (e.g., area) of aperture 3064 of the stabilizing element. For some applications, one or more dimensions of aperture 3064, defined by stabilizing element 3062, are substantially equal to one or more dimensions of opening 2045, defined by upstream support portion 2041. For some such applications, the expansion of both the downstream and upstream portions of the prosthetic valve are restricted to substantially the same transverse cross-sectional dimensions, thereby facilitating the primary structural element of the prosthetic valve to assume a generally prismatic (e.g., generally cylindrical) shape.

For applications where stabilizing element 3062 limits the expansion of prosthetic valve 2042, a radially-expansive force is thereby applied by prosthetic valve 2042 to stabilizing element 3062. The radially-expansive force typically couples the prosthetic valve to the stabilizing element. That is, for some applications, prosthetic valve 2042 is couplable to the stabilizing element. For some applications, the prosthetic valve is coupled to the stabilizing element by alternative or additional means. For example, the stabilizing element may comprise barbs and/or hooks, which facilitate coupling to the prosthetic valve.

For some applications of the invention, at least part (e.g., an inner surface) of stabilizing element 3062 comprises a friction coating that is configured to increase friction and, thereby, coupling between the stabilizing element and the prosthetic valve.

For some applications of the invention, at least part of stabilizing element 3062 is shaped to define ridges, which are configured (e.g., dimensioned) to protrude (e.g., interpose) within corresponding voids defined by the lattice structure of the prosthetic valve. The ridges facilitate coupling of the stabilizing element to the prosthetic valve, e.g., by inhibiting axial movement of the prosthetic valve through aperture 3064.

For some applications of the invention, a soft (e.g., crushable) material is disposed on the inner surface of stabilizing element 3062 (e.g., the stabilizing element comprises the soft material). When prosthetic valve 2042 expands, and applies radially-expansive force to the stabilizing element, (1) the struts of the lattice structure of the prosthetic valve compress (e.g., crush) the parts of the soft material against which the struts apply the force, and (2) the parts of the soft material that are disposed between the struts (i.e., that are disposed at voids defined by the lattice structure), form ridges that protrude between the struts (i.e., protrude into the voids). The protruding parts of the soft material facilitate coupling of the stabilizing element to the prosthetic valve, e.g., by inhibiting axial movement of the prosthetic valve through aperture 3064, such as by increasing friction.

For some applications of the invention, prosthetic valve 2042 (e.g., the primary structural element of prosthetic valve 2042) is shaped to define a circumferential groove that is configured (e.g., dimensioned) to receive stabilizing element 3062. That is, for some applications of the invention, stabilizing element 3062 is configured (e.g., dimensioned) to be placed in a circumferential groove defined by prosthetic valve 2042. When prosthetic valve 2042 is deployed, and expands within aperture 3064, element 3062 is disposed in the groove, thereby further facilitating coupling of the stabilizing element to the prosthetic valve, e.g., by inhibiting axial movement of the prosthetic valve through the aperture 3064.

Reference is made to FIGS. 5A-F, which are schematic illustrations of steps in transapical implantation of implant 2030h, comprising prosthetic valve 2042 and a prosthetic valve support 2040h, in a native valve, such as mitral valve 2024 of a heart 2020 of a subject, in accordance with some applications of the invention. For some applications of the invention, prosthetic valve support 2040h is analogous to other prosthetic valve supports described herein. Prosthetic valve support 2040h comprises upstream support portion 2041 and clips 2900, and is typically analogous to prosthetic valve support 2040b.

Figure 5A:
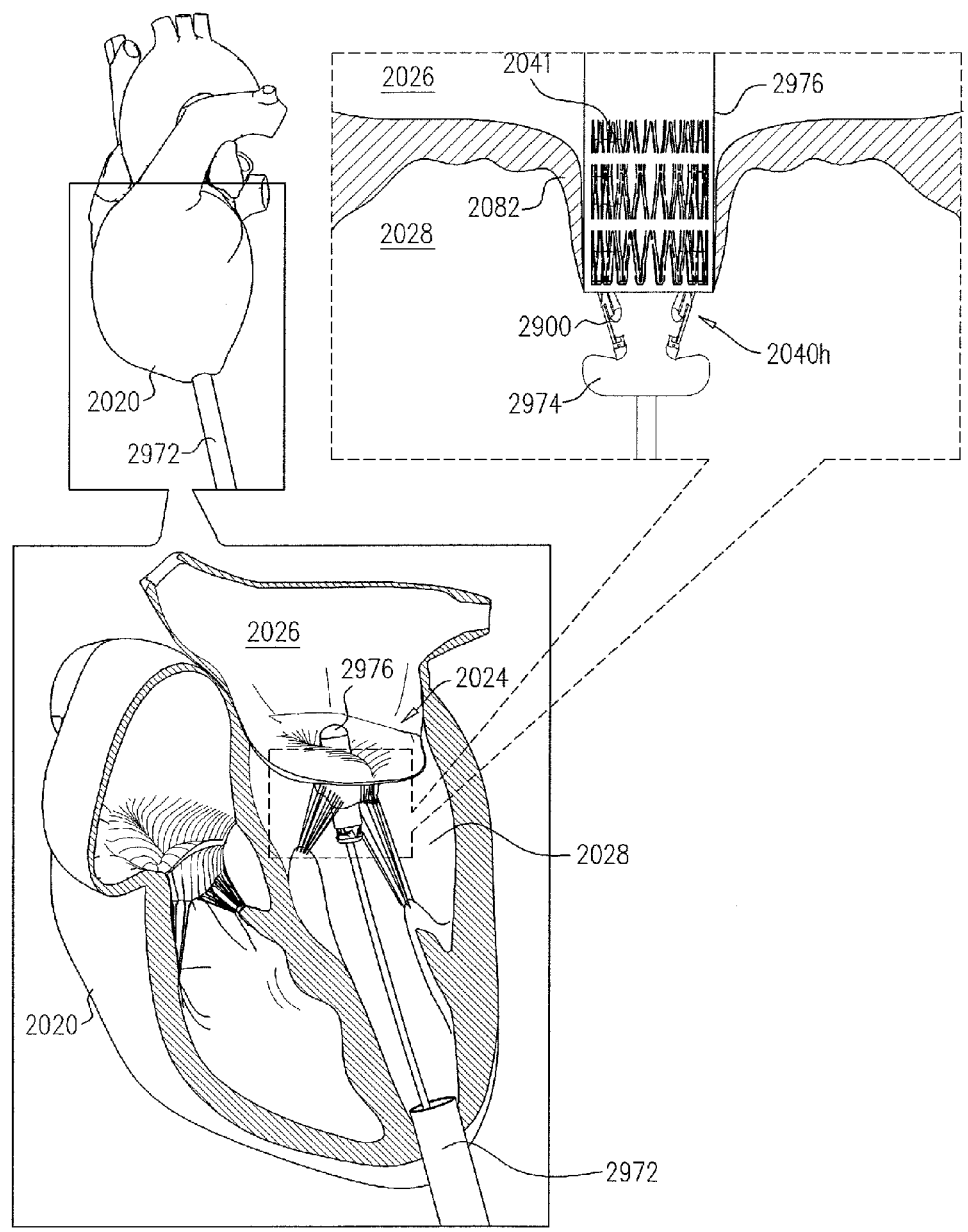

FIG. 5A shows support 2040h being delivered, via the apex of the heart, to left ventricle 2028 of the subject. During delivery, at least portion 2041 of support 2040h is typically disposed, in the compressed configuration thereof, within a delivery tube 2976. Typically, support 2040h and delivery tube 2976 are delivered transcatheterally via an incision between ribs of the subject, e.g., within an overtube 2972 of the delivery apparatus. Delivery tube 2976, containing portion 2041, is shown having been advanced distally (i.e., upstream) from the overtube, such that the delivery tube is disposed between native leaflets 2082 of the native valve. Upstream support portion 2041 is disposed, in the compressed configuration thereof, such that upstream end 2055 is upstream of downstream end 2053. At this stage of the procedure, clips 2900 are typically exposed from the proximal (i.e., downstream) end of delivery tube 2976. Typically, and as described hereinabove (e.g., with reference to FIG. 3A), clips 2900 are coupled to a scaffold, such as a core 2974. Clips 2900 are openable and closeable as described hereinabove with reference to FIGS. 2-3L, mutatis mutandis, and are clipped to leaflets 2082 so as to couple prosthetic valve support 2040h to the leaflets.

Figure 5B:
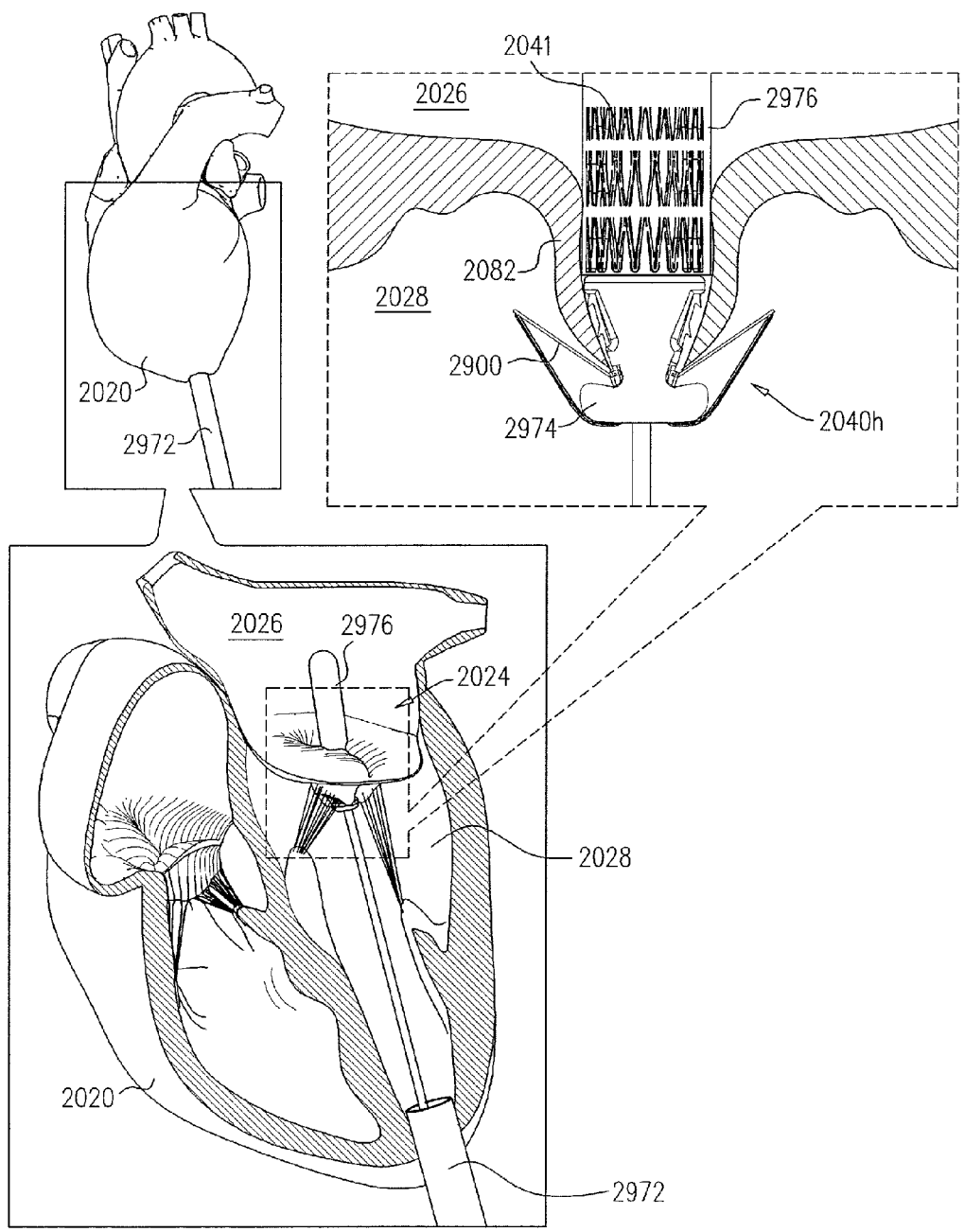

FIG. 5B shows clips 2900 in the open configuration thereof, and positioned such that the clips envelop native leaflets 2082. Clips 2082 are coupled to the native leaflets by moving the clips to the closed configuration thereof, while the leaflets are enveloped by the clips. As described hereinabove with reference to FIGS. 2-3L, mutatis mutandis, clips 2900 are coupled to downstream end 2053 of the compressed upstream support portion, and thereby coupling the clips to the leaflets, couples the downstream end of the compressed upstream support portion to the leaflets.

Figure 5C:
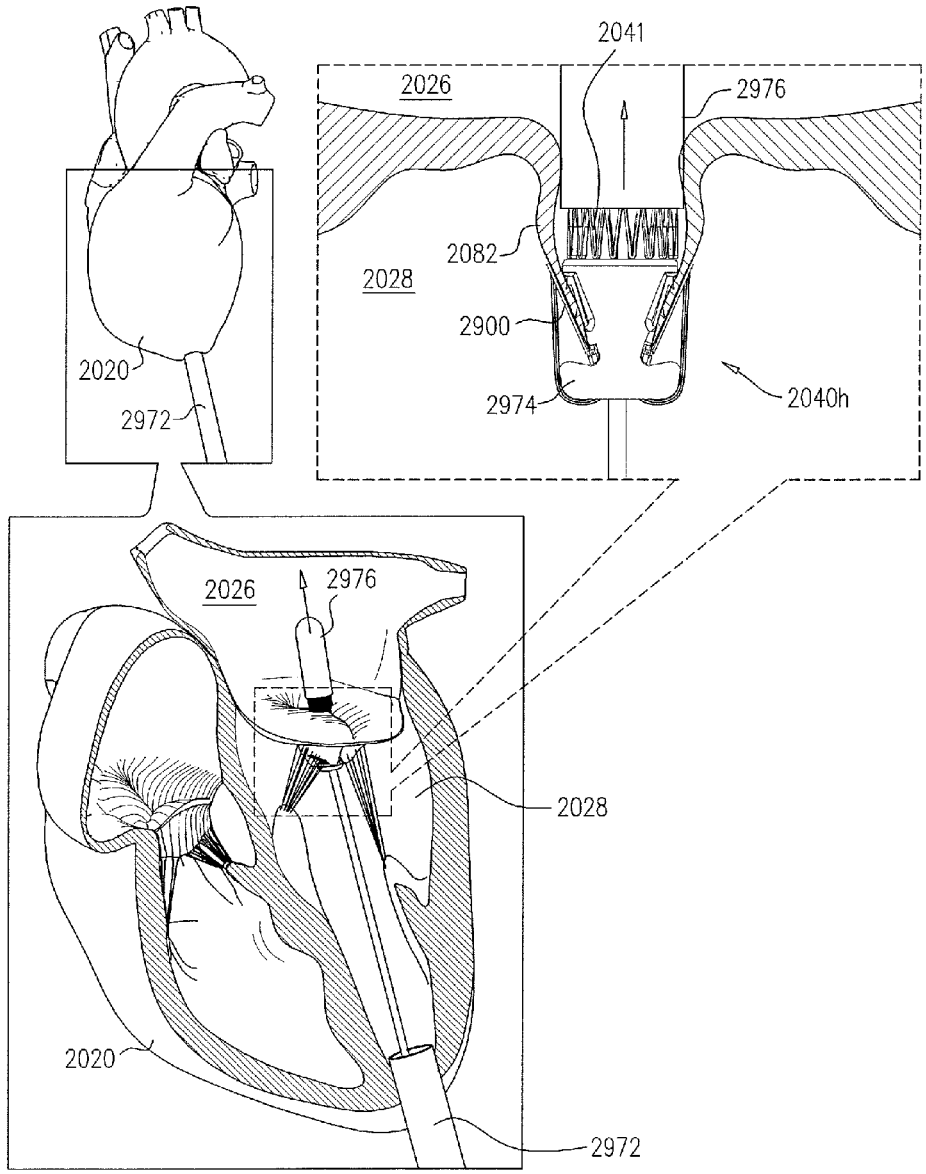

FIG. 5C shows clips 2900 in the closed configuration thereof, coupled to native leaflets 2900, and delivery tube 2976 being withdrawn distally from upstream support portion 2041. Following the coupling of the clips to the native leaflets, delivery tube 2976 is moved distally (i.e., upstream, e.g., atrially), thereby exposing successively more distal (e.g., upstream) parts of portion 2041. As described hereinabove (e.g., with reference to FIG. 3F, mutatis mutandis), as downstream end 2053 moves out of the delivery tube, it expands toward becoming and/or defining inner perimeter 2068 of portion 2041.

As successively more distal (e.g., upstream) parts of portion 2041 are exposed as they exit delivery tube 2976, they expand (e.g., radially). When portion 2041 is sufficiently exposed from the delivery tube (e.g., when upstream end 2055 is exposed from the delivery tube), upstream end 2055 expands to define outer perimeter 2069, as described hereinabove, mutatis mutandis. Following this implantation of prosthetic valve support 2040h, delivery tube 2976 is typically subsequently withdrawn proximally (e.g., downstream), via opening 2045 defined by upstream support portion 2041, and removed from the body of the subject, e.g., via overtube 2972.

As described hereinabove (e.g., for prosthetic valve support 2040b with reference to FIGS. 3G-H), following the implantation of the prosthetic valve support, clips 2900 allow movement of native leaflets 2082, at least in part. Thereby, implantation of the prosthetic valve support typically does not eliminate the native blood flow regulation functionality of the native valve.

FIG. 5D shows prosthetic valve support 2040*h* having been implanted at the native valve, such that clips 2900 are coupled to the native leaflets, and upstream support portion 2041 is disposed against the upstream side of the native valve (e.g., the upstream side of the native valve annulus). Following the implantation of prosthetic valve support 2040*h*, prosthetic valve 2042 is subsequently delivered transapically to ventricle 2028 of the subject, typically via overtube 2972. Prosthetic valve 2042 is delivered in a compressed configuration thereof, typically within a delivery tube 2986. Delivery tube 2986 is advanced into opening 2045 of upstream support portion 2041.

Figure 5E:
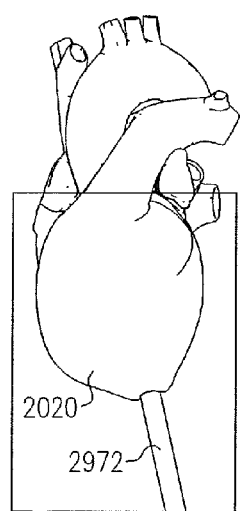
Figure 5E:
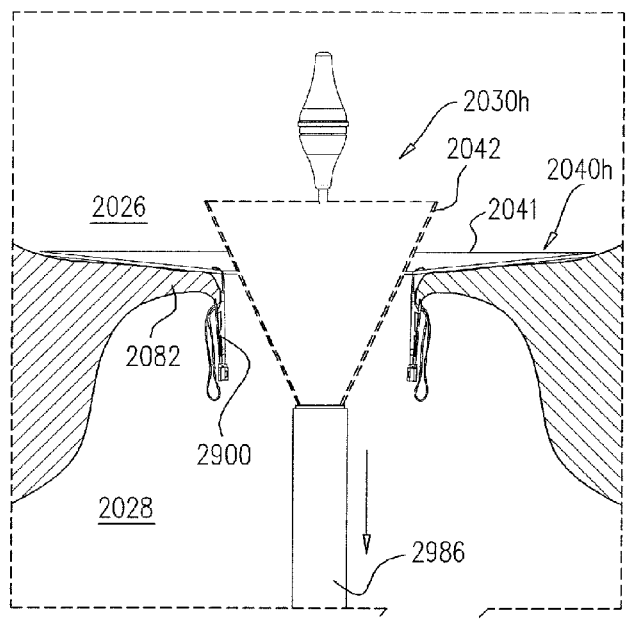
Figure 5E:
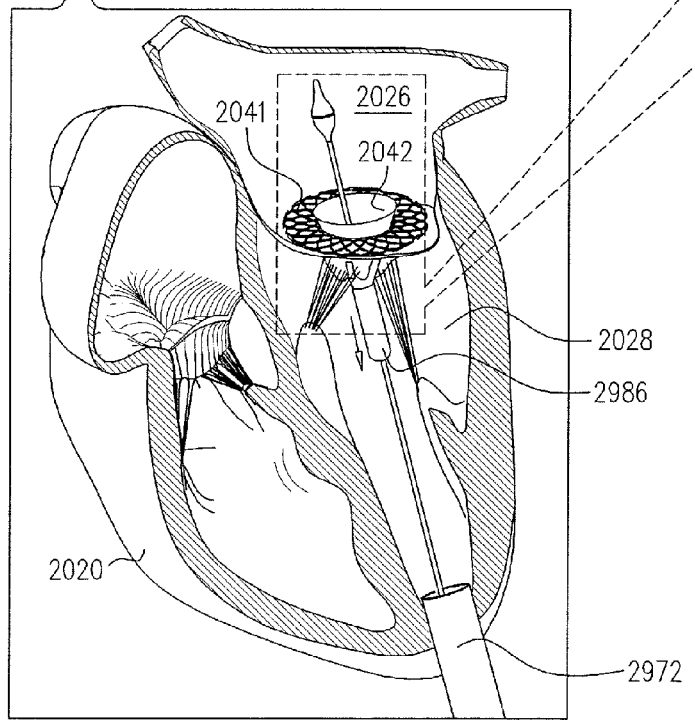

Reference is now made to FIG. 5E. The delivery tube is subsequently withdrawn proximally (e.g., ventricularly) from prosthetic valve 2042, such that the upstream end of the prosthetic valve is exposed. As successively more proximal (e.g., downstream) parts of prosthetic valve 2042 are exposed as they exit delivery tube 2986, they expand (e.g., radially). This expansion is illustrated in FIG. 5E, in which prosthetic valve 2042 is represented by a trapezoid/frustum. When prosthetic valve 2042 is sufficiently exposed from the delivery tube, the prosthetic valve engages inner perimeter 2068 of upstream support portion 2041 of support 2040*h*, and couples the prosthetic valve thereto, as described hereinabove, mutatis mutandis, thereby forming implant 2030*h*.

Figure 5F:
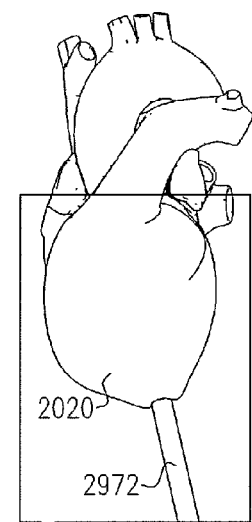
Figure 5F:
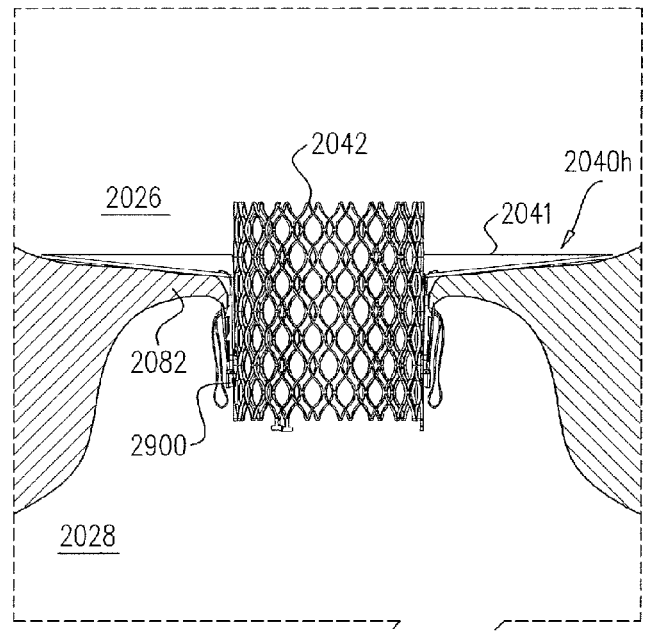
Figure 5F:
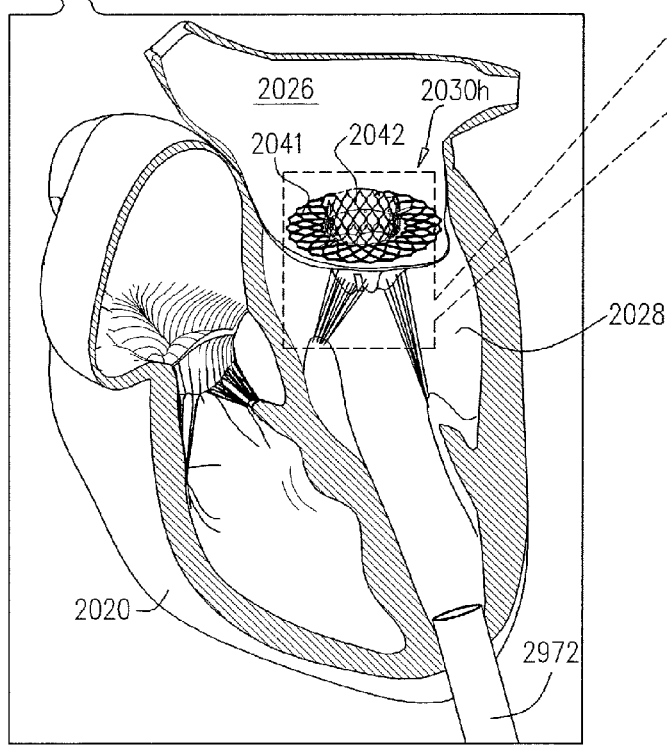

Reference is now made to FIG. 5F. Once prosthetic valve 2042 is completely exposed (e.g., deployed), the prosthetic valve thereby assumes its implanted configuration, in which it is coupled to prosthetic valve support 2040*h*, thereby replacing the native blood flow regulation functionality of the native valve with a substitute blood flow regulation functionality, as described hereinabove, mutatis mutandis. Delivery apparatus, such as delivery tube 2986 and overtube 2972, are subsequently removed from the body of the subject.

Reference is made to FIGS. 6-9, which are schematic illustrations of implants, each comprising a prosthetic valve support and a prosthetic valve, implanted at native valves of heart 2020 of a subject, in accordance with some applications of the invention. FIGS. 6-9 are not intended to limit the scope of the invention, but to indicate some placements of the implants with respect to the anatomy of the heart and/or native valve, and to illustrate commonalities between such placements.

Figure 6:
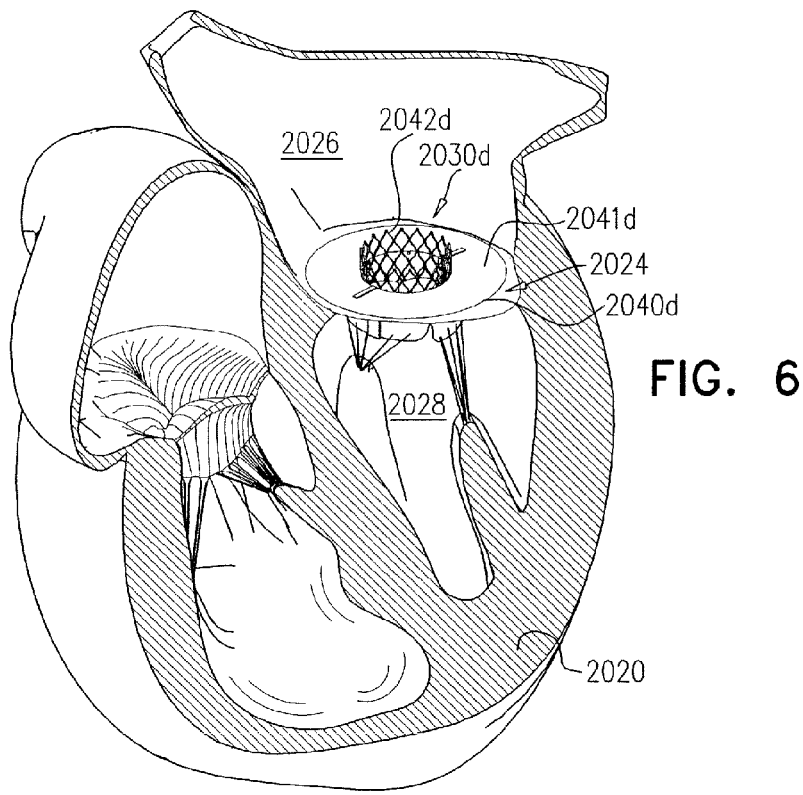
FIG. 6 is a schematic illustration of an implant, implanted at the mitral valve of a subject, in accordance with some applications of the invention.

FIG. 6 shows implant 2030*d*, comprising a prosthetic valve support 2040*d* and a prosthetic valve 2042*d*, implanted at mitral valve 2024 of heart 2020 of a subject, in accordance with some applications of the invention. For some applications of the invention, prosthetic valve support 2040*d* is analogous to other prosthetic valve supports described herein, and implant 2030*d* is analogous to other implants described herein. Implant 2030*d* (e.g., support 2040*d* and prosthetic valve 2042*d*) are configured (e.g., dimensioned) to be implanted at mitral valve 2024. Implant 2030*d* is typically implanted at mitral valve 2024 as described elsewhere herein (e.g., with reference to FIGS. 3A-L and/or 5A-E). An upstream support portion 2041*d* of support 2040*d* is disposed against the upstream (i.e., atrial) side of mitral valve 2024, and is coupled to the native valve, e.g., using clips or another support-anchoring element. Prosthetic valve 2042*d* is disposed and expanded in the opening defined by portion 2041*d*, thereby traversing the annulus of the native valve.

Figure 7:
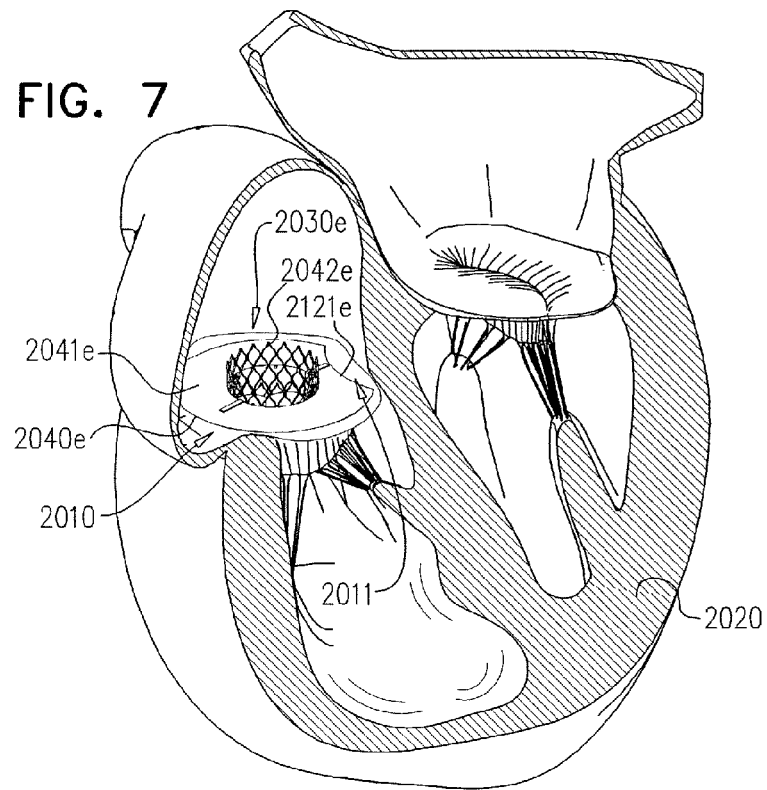
FIG. 7 is a schematic illustration of an implant, implanted at the tricuspid valve of a subject, in accordance with some applications of the invention.

FIG. 7 shows implant 2030*e*, comprising a prosthetic valve support 2040*e* and a prosthetic valve 2042*e*, implanted at tricuspid valve 2010 of heart 2020 of a subject, in accordance with some applications of the invention. For some applications of the invention, prosthetic valve support 2040*e* is analogous to other prosthetic valve supports described herein, and implant 2030*e* is analogous to other implants described herein. Implant 2030*e* (e.g., support 2040*e* and prosthetic valve 2042*e*) are configured (e.g., dimensioned) to be implanted at tricuspid valve 2010. For example, and as shown in FIG. 7, an upstream support portion 2041*e* of support 2040*e* typically defines a concavity 2121, configured to be oriented toward the atrioventricular (AV) node, so as to reduce a likelihood of support 2040*e* interfering with electrical activity of the heart. Upstream support portion 2041*e* of support 2040*e* is disposed against the upstream (i.e., atrial) side of tricuspid valve 2010, and is coupled to the native valve, e.g., using clips or another support-anchoring element. Prosthetic valve 2042*e* is disposed and expanded in the opening defined by portion 2041*e*, thereby traversing the annulus of the native valve.

Figures 8, 9:
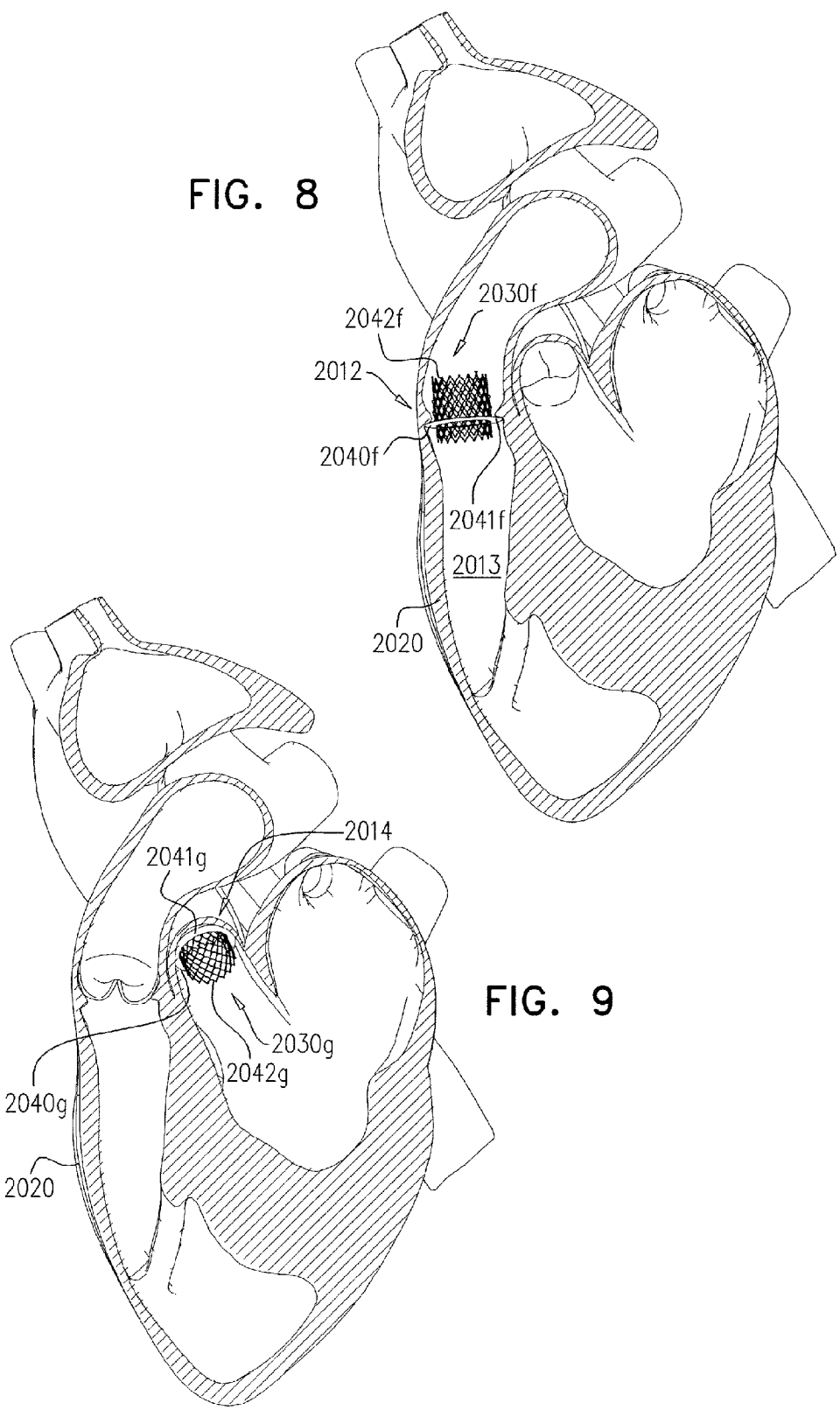
FIG. 8 is a schematic illustration of an implant, implanted at the pulmonary valve of a subject, in accordance with some applications of the invention.
FIG. 9 is a schematic illustration of an implant, implanted at the aortic valve of a subject, in accordance with some applications of the invention.

FIG. 8 shows implant 2030*f*, comprising a prosthetic valve support 2040*f* and a prosthetic valve 2042*f*, implanted at pulmonary valve 2012 of heart 2020 of a subject, in accordance with some applications of the invention. For some applications of the invention, prosthetic valve support 2040*f* is analogous to other prosthetic valve supports described herein, and implant 2030*f* is analogous to other implants described herein. Implant 2030*f* (e.g., support 2040*f* and prosthetic valve 2042*f*) are configured (e.g., dimensioned) to be implanted at pulmonary valve 2012. For example, and as shown in FIG. 8, an outer perimeter of upstream support portion 2041*f* of support 2040*f* may be dimensioned to be small enough to fit within the downstream portion of right ventricle 2013, but large enough to inhibit movement of implant 2030*f* downstream through the pulmonary valve. Upstream support portion 2041*f* of support 2040*f* is disposed against the upstream (i.e., ventricular) side of pulmonary valve 2012, and is coupled to the native valve, e.g., using clips or another support-anchoring element. Prosthetic valve 2042*f* is disposed and expanded in the opening defined by portion 2041*f*, thereby traversing the annulus of the native valve.

FIG. 9 shows implant 2030*g*, comprising a prosthetic valve support 2040*g* and a prosthetic valve 2042*g*, implanted at aortic valve 2014 of heart 2020 of a subject, in accordance with some applications of the invention. For some applications of the invention, prosthetic valve support 2040*g* is analogous to other prosthetic valve supports described herein, and implant 2030*g* is analogous to other implants described herein. Implant 2030*g* (e.g., support 2040*g* and prosthetic valve 2042*g*) are configured (e.g., dimensioned) to be implanted at aortic valve 2014. For example, and as shown in FIG. 9, an outer perimeter of upstream support portion 2041*g* of support 2040*g* may be dimensioned to be sufficiently large to inhibit movement of implant 2030*g* downstream through the aortic valve, and/or prosthetic valve 2042*g*, and prosthetic valve 2042*g* may be dimensioned to reduce a likelihood of interference with (e.g., reduction of) blood flow into the coronary arteries of the subject. Upstream support portion 2041*g* of support 2040*g* is disposed against the upstream (i.e., ventricular) side of aortic valve 2014, and is coupled to the native valve, e.g., using clips or another support-anchoring element. Prosthetic valve 2042*g* is disposed and expanded in the opening defined by portion 2041*g*, thereby traversing the annulus of the native valve.

FIGS. 6-9 show implants 2030*d*, 2030*e*, 2030*f* and 2030*g*, implanted at respective native heart valves. For some applications of the invention, these implants (e.g., the prosthetic valve support and the prosthetic valve that each implant comprises) are configured to be delivered and/or implanted transluminally (e.g., as described for implant 2030*b* with reference to FIGS. 3A-L). For some applications of the invention, these implants are configured to be delivered and/or implanted transapically (e.g., as described for implant 2030*h* with reference to FIGS. 5A-F). For some applications of the invention, these implants are configured to be delivered and/or implanted using other techniques (e.g., via other routes) known in the art.

Reference is made to FIGS. 10A-D, which are schematic illustrations of a prosthetic valve support 2040j, in accordance with some applications of the invention. For some applications of the invention, prosthetic valve support 2040j is analogous to other prosthetic valve supports (e.g., prosthetic valve support 2040) described herein. For some applications of the invention, prosthetic valve support 2040j may be used in combination with techniques described hereinabove, such as those described with reference to FIGS. 3A-L and 5A-F, mutatis mutandis.

Support 2040j comprises upstream support portion 2041, coupled to one or more clips 3000, configured to be coupled to one or more native leaflets of the native valve (e.g., as described hereinabove for clips 2900 with reference to FIGS. 3A-L and 5A-F, mutatis mutandis). For some applications of the invention, clips 3000 are analogous to clips 2900, described hereinabove.

Typically, support 2040j comprises two clips 3000, coupled to portion 2041 of support 2040j at or near inner perimeter 2068. For some applications, clips 3000 are disposed opposite each other. For some applications (e.g., for prosthetic valve supports that are configured to be coupled to tri-leaflet valves such as the tricuspid valve and/or the aortic valve), the prosthetic valve support comprises three clips, coupled to the upstream support portion.

Typically, clips 3000 are articulatably coupled to portion 2041 via a connector, as described hereinabove for clips 2900, mutatis mutandis. Typically, clips 3000 facilitate the coupling of support 2040j to the native valve without eliminating the native functionality of the native valve, as described hereinabove with respect to clips 2900, mutatis mutandis.

Each clip 3000 typically comprises two or more clip elements, such as a clip arm 3020 and a clip arm 3022, movable with respect to each other. Typically, the clip arms are articulatably-coupled at an articulation point 3021, and are movable with respect to each other by the relative angular disposition of the clip arms being controllable.

Figure 10A:
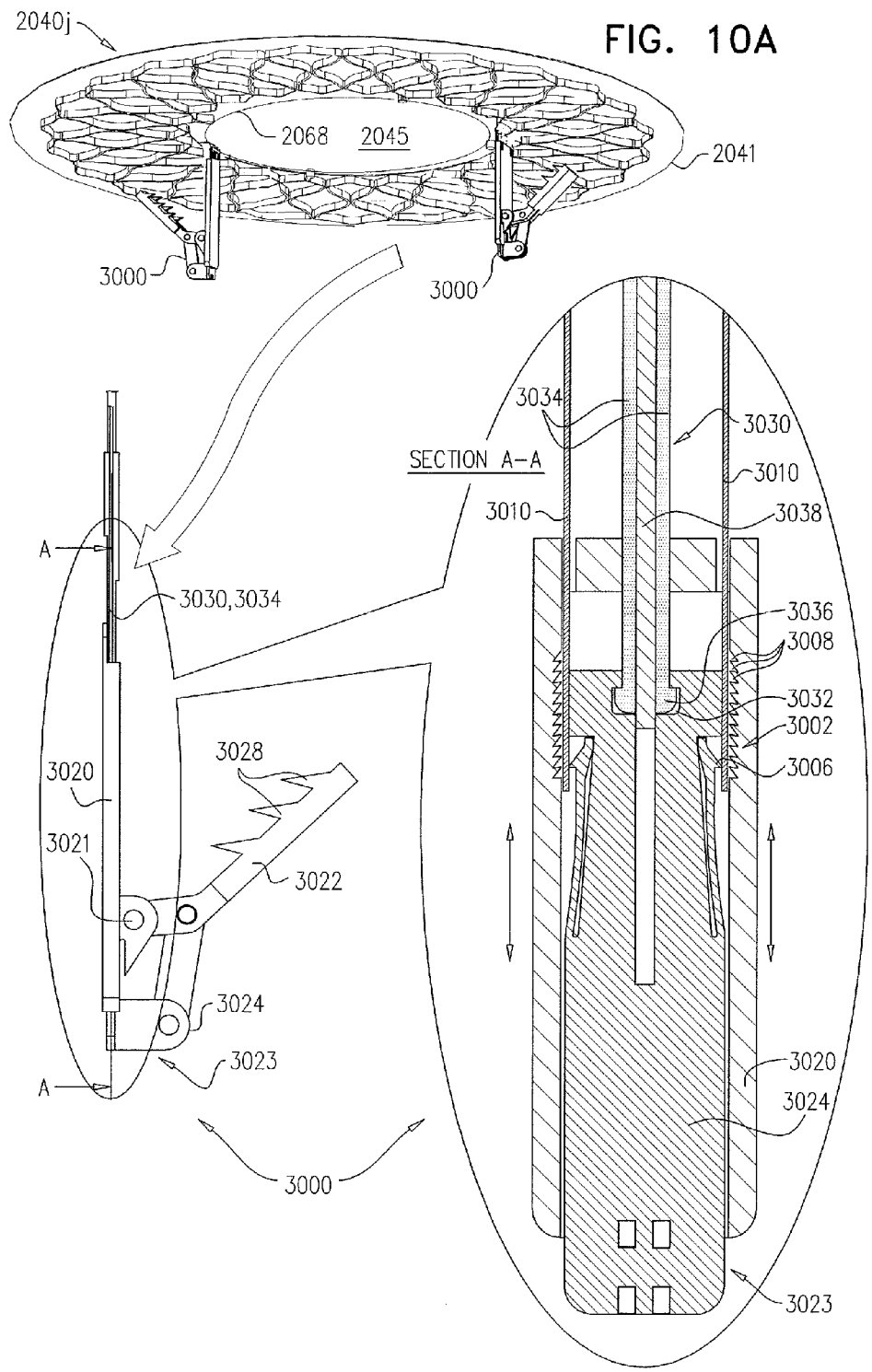
FIGS. 10A-D are schematic illustrations of a prosthetic valve support, for use with a prosthetic valve, in accordance with some applications of the invention.
Figure 10B:
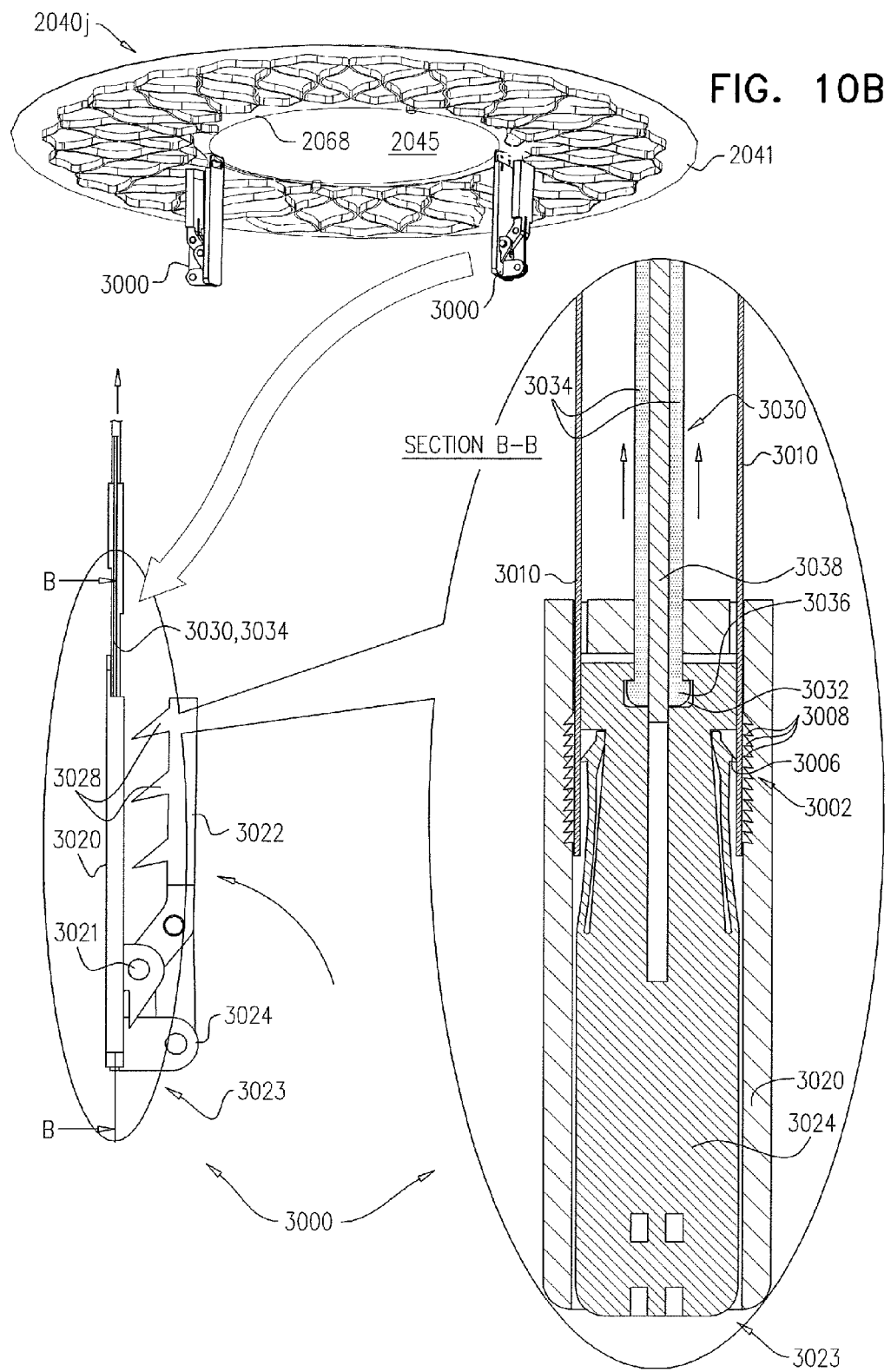

Clip 3000 has a closed configuration and an open configuration, and is movable between the closed and open configurations. FIG. 10A shows clip 3000 in the open configuration thereof, and FIG. 10B shows clip 3000 in the closed configuration thereof. In the closed configuration, arms 3020 and 3022 are relatively disposed at a generally small angle (e.g., less than 45 degrees, such as less than 20 degrees, such as less than 5 degrees) to each other. For some applications, in the closed configuration of clip 3000, arms 3020 and 3022 touch each other at a site that other than the articulation point. In the open configuration, the angular disposition of the clip arms relative to each other is greater than in the closed configuration. Typically, in the open configuration, the clip arms are disposed at greater than 35 degrees and/or less than 130 degrees, such as between 40 degrees and 120 degrees. For some applications, the clip arms have more than one open configuration. For example, the clip arms may be openable to an angle of greater than 120 degrees, but may be generally opened to an angle of between 40 and 90 degrees for coupling of the clips to the native leaflets.

When arm 3022 is in the closed configuration thereof, clip 3000 is in the closed configuration thereof. When arm 3022 is in the open configuration thereof, clip 3000 is in the open configuration thereof. That is, clip 3000 is movable between open and closed configurations thereof, by arm 3022 moving between open and closed configurations thereof.

Each clip 3000 is configured to be coupled to a native leaflet of the native valve by enveloping the native leaflet when the clip is in the open configuration thereof, and clipping the leaflet between the clip arms when the clip subsequently moves toward the closed configuration thereof.

Clip 3000 further comprises a clip-controller interface 3023, typically comprising a linkage 3024, which facilitates movement of arm 3022 between the closed and open configurations, i.e., relative angular movement of arms 3020 and 3022. Linkage 3024 is typically coupled to clip arm 3022, and controlled from outside the body of the subject. For example, linkage 3024 may be coupled to arm 3022, and extend to a clip controller (e.g., clip controller 3030, described hereinbelow), ultimately controlled by a physician. Typically, linkage 3024 is articulatably coupled to arm 3022. Typically, linkage 3024 is coupled to arm 3022 such that (1) moving the linkage in one direction (e.g., by pushing distally) moves arm 3022 toward the open configuration, and (2) moving the linkage in the other direction (e.g., by pulling proximally), moves the arm toward the closed configuration.

Typically, linkage 3024 comprises one or more portions. For some applications, at least one of the portions of linkage 3024 is articulatably coupled to another one of the portions of the linkage. For some applications, at least part of at least one portion of linkage 3024 is disposed within, and slidable through, a cavity defined by clip arm 3022.

As described hereinabove (e.g., with reference to FIGS. 1A-D), upstream support portion 2041 is expandable from a compressed to an uncompressed configuration thereof. Clips 3000 are generally controllable (e.g., movable between the open and closed configurations thereof) irrespective of and/or independent to a state of expansion of the upstream support portion, e.g., as described hereinabove with respect to clips 2900, mutatis mutandis. That is, clips 3000 are typically configured to be controllable independently of a state of deployment of the prosthetic valve support. Thus, a physician may independently control (1) the coupling (e.g., 'clipping') of clips 3000 to the leaflets of the native valve, and (2) the deployment of the prosthetic valve support (e.g., expansion of the upstream support portion).

For some applications of the invention, both clips 3000 are controlled simultaneously by a user (e.g., clips 3000 are configured to operate simultaneously). For some applications, each clip 3000 is controllable independently. For some applications, one or more of the clip arms comprises one or more grips 3028, such as teeth, which facilitate coupling of the clip to the native leaflet when the clip is closed. For some applications, clips 3000 may alternatively or additionally be coupled to the prosthetic valve, and configured to couple the prosthetic valve directly to the native valve.

Typically, clips 3000 further comprise at least one securing element 3002, configured to secure the clips in the closed configuration, following coupling of the clips to the native leaflets. For some applications of the invention, securing element 3002 is configured to secure the clips in one or more pre-defined closed configurations (e.g., in a partially-closed configuration). Typically, securing element 3002 comprises at least one tooth 3006, and at least one respective socket 3008, in which the tooth is disposable. Typically, (1) linkage 3024 comprises tooth 3006, (2) enclosure 3004 defines socket 3008, and (3) the securing element is configured to secure the clips in the closed configuration by the tooth being disposable in the socket. For applications in which at least part of linkage 3024 is disposed within and slidable through the cavity defined by clip arm 3022, socket 3008 is typically defined by the clip arm.

Figure 10C:
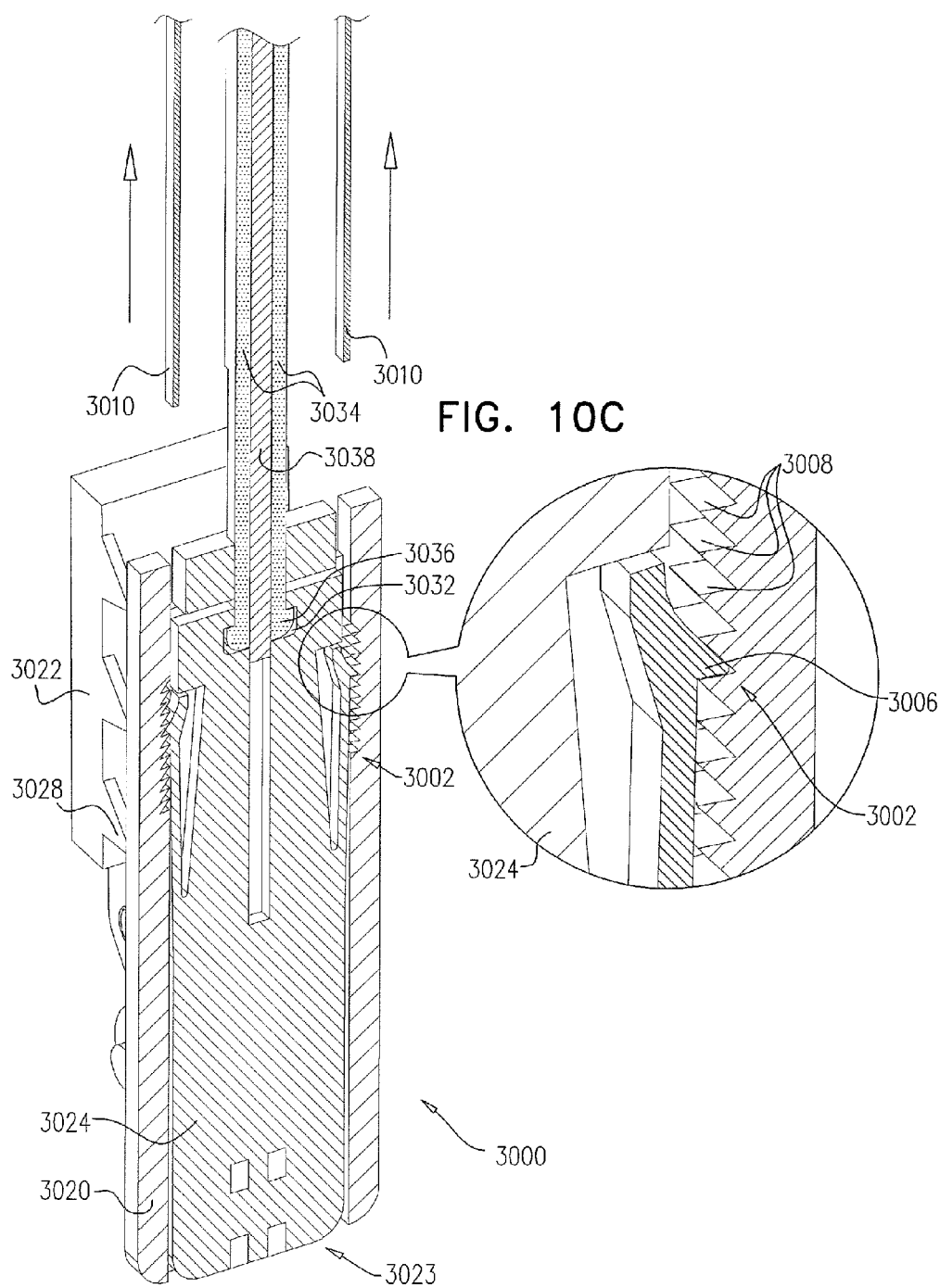

Typically, linkage 3024 is configured to be biased such that tooth 3006 is disposed in socket 3008, and an obstructing element 3010 is configured to prevent the tooth from moving into the socket by being placeable between the tooth and the socket. For some applications, obstructing element 3010 comprises a strip of metal or plastic. As shown in FIG. 10C, removing element 3010 from between tooth 3006 and socket 3008 thereby allows the tooth to move into the socket, and inhibits subsequent movement of linkage 3024. For some applications of the invention, clip 3000 is configured such that, in the absence of element 3010, linkage 3024 is movable in one direction and not in the other direction, e.g., the clip is further closable but not re-openable. For example, securing element 3002 may comprise at least one tooth 3006 and a plurality of sockets 3008, which are configured to act as a ratchet.

Typically, clips 3000 are used to couple prosthetic valve support 2040j to the leaflets of the native valve, as clips 2900 are used to couple prosthetic valve support 2040b to the leaflets, mutatis mutandis. That is:

(1) the prosthetic valve support is typically delivered to the native valve while the support is in the compressed configuration thereof;

(2) in the compressed configuration of the support, the clips are typically disposed downstream to the cylinder of upstream support portion 2041; and (3) the clips are coupled (e.g., by a physician) to the leaflets of the native valve by enveloping the leaflets between the clip arms, and moving the clips to the closed configuration thereof.

While clips 3000 are coupled to the native leaflets (i.e., while the clips are closed and enveloping the native leaflets), the physician typically secures the clips in the closed configuration (e.g., by removing obstructing element 2010), thereby securing the clips to the leaflets.

Prosthetic valve support 2040j is implanted using support-delivery apparatus. For some applications of the invention, the support-delivery apparatus for implantation of support 2040j is analogous to support-delivery apparatus 2924 (described with reference to FIGS. 3A-L) for delivery of prosthetic valve support 2040b. As described hereinabove, each clip 3000 comprises a clip-controller interface, typically linkage 3024, which is configured to open the clip when moved in one direction (e.g., pulled proximally), and to close the clip when moved in another direction (e.g., pushed distally). Typically, linkage 3024 is coupled to a clip controller, such as clip controller 3030, which the support-delivery apparatus typically comprises, and the clip controller is used by the physician to control the clips (e.g., from outside the body of the subject). Typically, clips controller 3030 is decouplable from the clip-controller interface, e.g., subsequent to the coupling of the clip to the native leaflets. For some applications of the invention, and as shown in FIGS. 10A-D, one portion (e.g., one end) of linkage 3024 is coupled to clip arm 3072, and another portion (e.g., another end) of linkage 3024 is coupled to controller 3030.

Figure 10D:
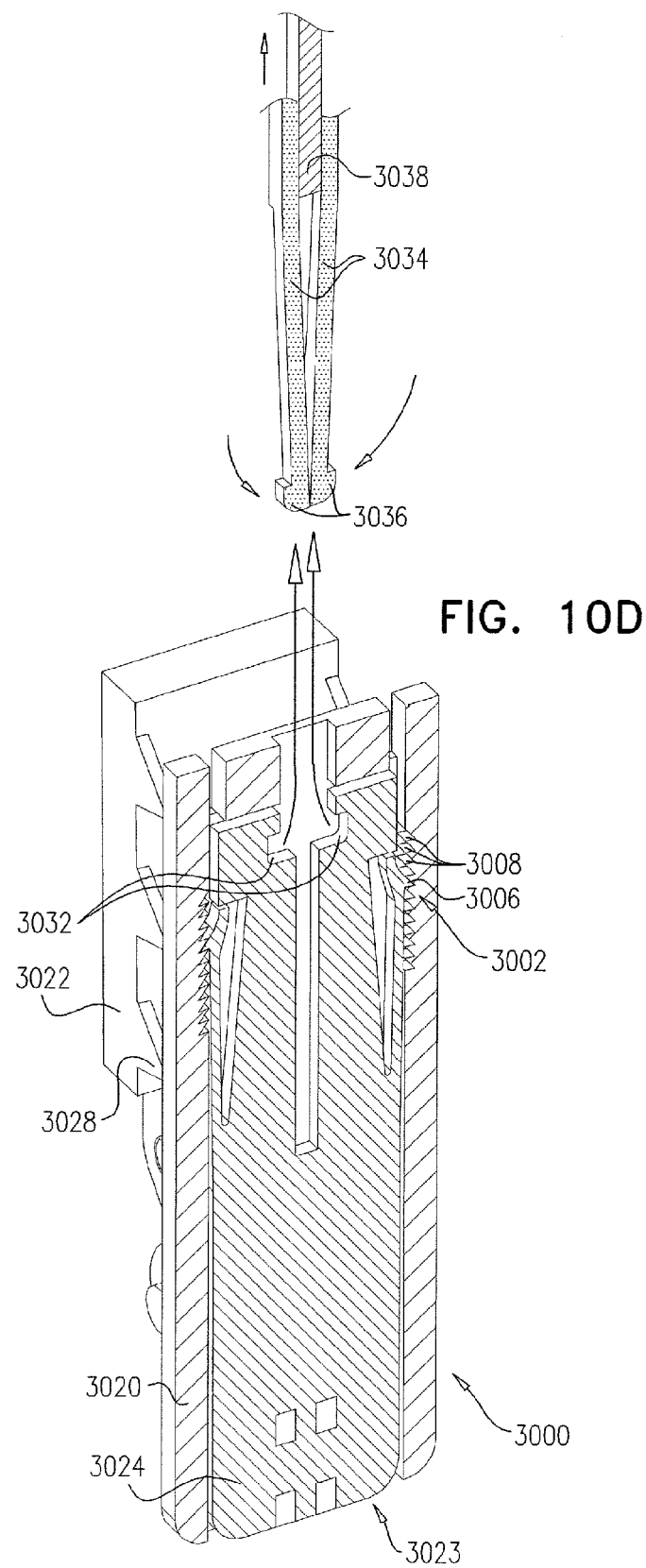

Typically, and as shown in FIGS. 10A-C, (1) linkage 3024 is shaped to define one or more depressions 3032, (2) controller 3030 comprises one or more shafts 3034, each shaft being shaped to define at least one projection 3036, and (3) the controller is couplable to the linkage by each projection being disposable in a respective depression. Typically, shafts 3034 are configured to be biased such that projections 3036 are not disposed in respective depressions 3032, and a restraint 3038 is couplable to at least the shafts, and is configured to retain the projections in the respective depressions. For example, restraint 3038 may be disposed between shafts 3034, and prevents the shafts from moving together. Decoupling of restraint 3038 from shafts 3034 (e.g., removing the restraint from between the shafts) thereby decouples controller 3030 from linkage 3024 by allowing projections 3036 to move out of depressions 3032, as shown in FIG. 10D.

Thereby, controller 2030 is configured to (1) be coupled to the clip-controller interface (e.g., to linkage 3024), (2) control a relative angular disposition of the clip arms (i.e., a state of openness of the clips), and (3) be decoupled from the clip-controller interface.

Reference is made to FIGS. 1A-10D. For each of the prosthetic valve supports described, at least a part of the prosthetic valve support circumscribes (e.g., encloses on all lateral sides) a space. As described hereinabove, the upstream support portion of the prosthetic valve support is shaped to define opening. This opening is thereby an example of one such space that at least part of the prosthetic valve support circumscribes. As described hereinabove, for some applications, the prosthetic valve support comprises a stabilizing element, which defines an aperture. The stabilizing element is thereby an additional part of the prosthetic valve support that circumscribes a space. That is, for prosthetic valve supports that comprise a stabilizing element, the aperture defined by the stabilizing element is another such space that at least part of the prosthetic valve support circumscribes.

Following implantation, the part of the prosthetic valve support that circumscribes the opening (i.e., the upstream support portion) is typically disposed only upstream of the native leaflets and/or annulus. When the implant comprises a stabilizing element, following implantation, the portion of the prosthetic valve support that circumscribes the aperture (i.e., the stabilizing element) is typically disposed only downstream to the native leaflets and/or annulus. That is, typically, no part of the implant that circumscribes a space that has a perimeter greater than 60 mm traverses the native leaflets. For some applications, no part of the implant that circumscribes a space that has a perimeter greater than 60 mm traverses the native annulus. It is hypothesized that this advantageously facilitates continued function of the native leaflets following implantation of the prosthetic valve support, and prior to the implantation of a prosthetic valve, as described hereinabove.

Reference is again made to FIGS. 1A-10D. For clarity, FIGS. 3A-H and 4A-D do not show regions of the native leaflets of the native valve that are closer to, or further from, the reader, than the regions to which the clips are coupled (i.e., regions of the native leaflets that are closer to the commissures than the regions to which the clips are coupled). That is, the native valve is shown generally cross-sectionally in these figures. In FIGS. 3G-H and 4B-C, the movement of the clips and native leaflets following coupling of the prosthetic valve support to the native valve is shown such that, when the native leaflets are closed, the clips meet generally only at downstream (e.g., distal) ends thereof. That is, coaptation of the native leaflets (e.g., as shown in FIG. 3A) at the regions to which the clips are coupled, is not shown in FIGS. 3H and 4C. However, regions of the native leaflets that are closer to the commissures than the regions to which the clips are coupled, typically do coapt. Furthermore, for some applications of the invention, the regions of the native leaflets to which the clips are coupled also coapt.

Clips described hereinabove (e.g., clips 2900 and 3000) are described as typically coupled to the upstream support portion of the prosthetic valve support via a connector (e.g., connector 2540), which is shown as generally short and hinge-like. For some applications of the invention, the connector is longer, and may comprise a flexible strip or wire.

Typically, this longer connector facilitates coaptation of the native leaflets, including at regions of the native leaflets to which the clips are coupled.

Reference is again made to FIGS. 1A-10D. It is to be noted that the apparatus and techniques described hereinabove are not limited to the combinations described hereinabove. For example:

(1) any of the implantation techniques and/or delivery apparatus described hereinabove may be used in combination with any of the implants described hereinabove, mutatis mutandis. For example, the implantation techniques and delivery apparatus described for implants 2030b (with reference to FIGS. 3A-L) and/or 2030h (with reference to FIGS. 5A-E), may be used in combination with prosthetic valve support 2040c, described with reference to FIGS. 4A-D, and/or with prosthetic valve support 2040j, described with reference to FIGS. 10A-D, mutatis mutandis.

(2) any of the prosthetic valves described hereinabove may be used in combination with any of the prosthetic valve supports described hereinabove, and (3) any of the prosthetic valve supports described hereinabove may comprise any of the upstream support portions, clips, and/or stabilizing elements described hereinabove.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a prosthetic valve for implantation at a native valve of a heart of a subject, the apparatus comprising:
   an overtube; and
   an upstream support portion, the upstream support portion:
   (a) having a compressed configuration in which the support is transcatheterally deliverable to the native valve within the overtube and in which the upstream support portion has a generally cylindrical shape, the cylindrical shape having a downstream end and an upstream end, each end having a perimeter, each perimeter of the cylindrical shape having a length and defining a free edge,
   (b) having an uncompressed configuration in which the upstream support portion:
      is configured to be placed against an upstream side of an annulus of the native valve,
      is shaped to define an opening, and
      has an outer perimeter and an inner perimeter, and
   (c) being movable from the compressed configuration to the uncompressed configuration by the downstream end being deployed from the overtube before the upstream end is deployed from the overtube,
   the apparatus being configured such that, upon deployment from the overtube, the upstream support portion moves from the compressed configuration to the uncompressed configuration thereof such that:
      the perimeter of the downstream end of the upstream support portion in the compressed configuration thereof becomes the inner perimeter of the upstream support portion in the uncompressed configuration thereof, and
      the perimeter of the upstream end of the upstream support portion in the compressed configuration thereof becomes the outer perimeter of the upstream support portion in the uncompressed configuration thereof.

2. The apparatus according to claim 1, wherein the apparatus is configured such that, when the upstream support portion moves from the compressed configuration to the uncompressed configuration thereof, the length of the perimeter of the upstream end of the upstream support portion in the compressed configuration thereof increases more than does the length of the perimeter of the downstream end of the upstream support portion in the compressed configuration thereof.

3. The apparatus according to claim 1, wherein the upstream support portion, in the uncompressed configuration thereof, is generally annular.

4. The apparatus according to claim 3, wherein the upstream support portion, in the uncompressed configuration thereof, is generally flat.

5. The apparatus according to claim 1, wherein the length of the outer perimeter is at least 10% greater than the length of the inner perimeter.

6. The apparatus according to claim 1, wherein the inner perimeter of the upstream support portion is configured to be coupled to the prosthetic valve.

7. The apparatus according to claim 1, wherein, in the uncompressed configuration thereof, any portion of the apparatus that circumscribes a space that has a perimeter greater than 60 mm has a depth of less than 2 mm.

8. The apparatus according to claim 1, wherein the upstream support portion is shaped such that the opening defined by the inner perimeter of the upstream support portion has a depth, and has a diameter that is more than 4 times greater than the depth.

9. The apparatus according to claim 1, further comprising the prosthetic valve.

10. The apparatus according to claim 1, wherein the overtube is configured to constrain the upstream support portion in the compressed configuration thereof while the upstream support portion is disposed within the overtube.

11. The apparatus according to claim 1, further comprising at least one clip, the clip comprising a plurality of clip arms, and being configured to couple the upstream support portion to the native valve.

12. The apparatus according to claim 11, wherein the clip is articulatably coupled to the upstream support portion.

13. The apparatus according to claim 11, wherein the clip has an open configuration and a closed configuration, and is movable between the open and closed configurations irrespective of a state of deployment of the upstream support portion.

14. Apparatus for use with a native heart valve of a subject, the native heart valve having a native annulus, the apparatus comprising:
   (A) a prosthetic valve support, comprising an upstream support portion, the upstream support portion having:
      a compressed configuration in which the upstream support portion is generally cylindrical, and is transcatheterally deliverable to the native valve, and
      an uncompressed configuration in which the upstream support portion:
         is configured to be placed against an upstream side of an annulus of the native heart valve, and
         has an inner perimeter that defines an opening; and
   (B) a prosthetic valve:
      having a compressed configuration in which the prosthetic valve is transcatheterally deliverable to the native valve, and advanceable into the opening defined by the upstream support portion, and
      being intracorporeally couplable to the upstream support portion by being expanded, the apparatus being configured such that, when the prosthetic valve is expanded, the expansion of the prosthetic valve is restricted by the prosthetic valve support, without causing the prosthetic valve support to apply a radially-expansive force to the native annulus, and wherein:

in the uncompressed configuration thereof, the upstream support portion has an upstream side and a downstream side, and a total height from the upstream side to the downstream side, the prosthetic valve has an upstream end and a downstream end, and a height from the upstream end to the downstream end, and the height of the prosthetic valve is at least 1.5 times greater than the total height of the upstream support portion.

15. The apparatus according to claim 14, wherein:

the upstream support portion, in the compressed configuration thereof, has an upstream end and a downstream end, each end having a perimeter, each perimeter having a length, and the upstream support portion is configured such that, when the upstream support portion moves from the compressed configuration toward the uncompressed configuration thereof:

the perimeter of the downstream end of the upstream support portion in the compressed configuration thereof becomes the inner perimeter of the upstream support portion in the uncompressed configuration thereof, and the perimeter of the upstream end of the upstream support portion in the compressed configuration thereof becomes an outer perimeter of the upstream support portion in the uncompressed configuration thereof.

16. The apparatus according to claim 14, wherein the prosthetic valve is intracorporeally couplable to the upstream support portion by being expanded within the opening defined by the inner perimeter of the upstream support portion.

17. The apparatus according to claim 16, wherein the apparatus is configured such that, when the prosthetic valve is expanded, the expansion of the prosthetic valve is restricted by the inner perimeter of the upstream support portion.

18. The apparatus according to claim 14, wherein the prosthetic valve support further comprises a flexible and annular stabilizing element, shaped to define an aperture.

19. A method for use with a prosthetic valve for implantation at a native valve of a heart of a subject, the method comprising:

delivering an upstream support portion of a prosthetic valve support, in a compressed configuration thereof, to an upstream side of the native valve, the upstream support portion in the compressed configuration thereof, having a generally cylindrical shape, the cylindrical shape having a downstream end and an upstream end, each end having a perimeter that defines a free edge, each perimeter of the cylindrical shape having a length;

coupling the prosthetic valve support to the native valve; and subsequently expanding the upstream support portion toward an uncompressed configuration thereof, such that:

the perimeter of the downstream end of the upstream support portion in the compressed configuration thereof becomes an inner perimeter of the upstream support portion in the uncompressed configuration thereof, the perimeter of the upstream end of the upstream support portion in the compressed configuration thereof becomes an outer perimeter of the upstream support portion in the uncompressed configuration thereof, and the inner perimeter of the upstream support portion defines an opening.

20. The method according to claim 19, wherein coupling the prosthetic valve support to the native valve comprises coupling the downstream end of the upstream support portion in the compressed configuration thereof to the native valve.

21. The method according to claim 19, wherein expanding the upstream support portion toward the uncompressed configuration thereof, comprises increasing the length of the perimeter of the upstream end of the upstream support portion more than the length of the perimeter of the downstream end of the upstream support portion.

22. The method according to claim 19, further comprising subsequently coupling the prosthetic valve to the prosthetic valve support by expanding the prosthetic valve within the opening defined by the upstream support portion.

23. The method according to claim 19, wherein coupling the prosthetic valve support to the native valve comprises coupling the prosthetic valve support to the native valve in a manner that allows the native valve to continue to function, at least in part.

24. The method according to claim 19, wherein expanding the upstream support portion toward the uncompressed configuration thereof, comprises expanding the upstream support portion such that the length of the outer perimeter is at least 10% greater than the length of the inner perimeter.

* * * * *